US012398184B2

(12) United States Patent
Tolia et al.

(10) Patent No.: US 12,398,184 B2
(45) Date of Patent: Aug. 26, 2025

(54) COMPOSITIONS COMPRISING CelTOS IMMUNOGENS AND ANTIBODIES AND METHOD OF USE THEREOF

(71) Applicants: Washington University, St. Louis, MO (US); University of South Florida, Tampa, FL (US)

(72) Inventors: Niraj Tolia, St. Louis, MO (US); John Jimah, St. Louis, MO (US); Nichole Salinas, St. Loius, MO (US); Darya Urusova, St. Louis, MO (US); John Adams, Tampa, FL (US); Shulin Xu, Tampa, FL (US); Allison Roth, Tampa, FL (US); Hirdesh Kumar, St. Louis, MO (US)

(73) Assignees: Washington University, St. Louis, MO (US); University of South Florida, Tampa, FL (US)

( * ) Notice: Subject to any disclaimer, the term of this patent is extended or adjusted under 35 U.S.C. 154(b) by 232 days.

(21) Appl. No.: 16/346,811

(22) PCT Filed: Nov. 1, 2017

(86) PCT No.: PCT/US2017/059589
§ 371 (c)(1),
(2) Date: May 1, 2019

(87) PCT Pub. No.: WO2018/085444
PCT Pub. Date: May 11, 2018

(65) Prior Publication Data
US 2019/0276506 A1    Sep. 12, 2019

Related U.S. Application Data

(60) Provisional application No. 62/415,894, filed on Nov. 1, 2016.

(51) Int. Cl.
| | |
|---|---|
| *C07K 14/445* | (2006.01) |
| *A61K 9/00* | (2006.01) |
| *A61K 39/00* | (2006.01) |
| *A61K 39/015* | (2006.01) |
| *A61K 39/018* | (2006.01) |
| *A61K 39/39* | (2006.01) |
| *A61P 33/06* | (2006.01) |
| *C07K 16/20* | (2006.01) |

(52) U.S. Cl.
CPC .......... *C07K 14/445* (2013.01); *A61K 9/0019* (2013.01); *A61K 39/015* (2013.01); *A61K 39/018* (2013.01); *A61K 39/39* (2013.01); *A61P 33/06* (2018.01); *C07K 16/205* (2013.01); *A61K 2039/505* (2013.01); *A61K 2039/545* (2013.01); *A61K 2039/55* (2013.01); *C07K 2317/34* (2013.01); *C07K 2317/55* (2013.01); *C07K 2317/76* (2013.01); *Y02A 50/30* (2018.01)

(58) Field of Classification Search
CPC ................ C07K 14/445; C07K 16/205; C07K 2317/34; C07K 2317/55; C07K 2317/76; A61P 333/06; A61K 9/0019; A61K 39/015; A61K 39/018; A61K 39/39; A61K 2039/505; A61K 2309/545; A61K 2039/55; Y02A 50/30
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,868,116 A | 9/1989 | Morgan et al. |
| 4,897,355 A | 1/1990 | Eppstein et al. |
| 4,925,661 A | 5/1990 | Huang |
| 4,954,345 A | 9/1990 | Muller |
| 4,957,735 A | 9/1990 | Huang |
| 4,980,286 A | 12/1990 | Morgan et al. |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 6,261,834 B1 | 7/2001 | Srivastava |
| 7,722,889 B2 | 5/2010 | Duffy et al. |
| 8,017,745 B2 | 9/2011 | Sette et al. |
| 2010/0260668 A1 | 10/2010 | Ghayur et al. |
| 2012/0237538 A1 | 9/2012 | Angov et al. |

(Continued)

FOREIGN PATENT DOCUMENTS

| | | |
|---|---|---|
| EP | 2796147 A1 | 10/2014 |
| WO | 1989007136 A2 | 8/1989 |

(Continued)

OTHER PUBLICATIONS

Skolnick et al. (Trends in Biotechnology 18: 34-39, 2000).*

(Continued)

*Primary Examiner* — Robert A Zeman
(74) *Attorney, Agent, or Firm* — Polsinelli PC

(57) ABSTRACT

The present disclosure provides immunogenic compositions and methods for vaccination with a CelTOS immunogen. The immunogenic composition comprises *Babesia*, *Theileria* or *Cytauxzoon* CelTOS. The immunogenic composition may also comprise CelTOS with structural changes that affect immune recognition.

7 Claims, 21 Drawing Sheets
(13 of 21 Drawing Sheet(s) Filed in Color)
Specification includes a Sequence Listing.

(56) References Cited

U.S. PATENT DOCUMENTS

| | | | |
|---|---|---|---|
| 2013/0273112 A1 | 10/2013 | Weiner et al. | |
| 2016/0031953 A1 | 2/2016 | Angov et al. | |
| 2016/0083439 A1 | 3/2016 | Boes et al. | |
| 2016/0291020 A1 | 10/2016 | Ziemann et al. | |

FOREIGN PATENT DOCUMENTS

| | | |
|---|---|---|
| WO | 1990002806 A1 | 3/1990 |
| WO | 2000056365 A1 | 9/2000 |
| WO | 2003009869 A1 | 2/2003 |
| WO | 2018085444 A1 | 5/2018 |

OTHER PUBLICATIONS

Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, pp. 12272-12273).*
Sela-Culang et al. (Frontiers in Immunology, 2013 vol. 4, article 302, pp. 1-13).*
Adams, P. et al., "PHENIX: building new software for automated crystallographic structure determination," Acta Cryst. Section D Biol. Cryst., 2002, pp. 1948-1954, vol. D58, Pt. 11.
Altschul, S. et al., "Basic Local Alignment Search Tool," J. Mo. Biol., 1990, pp. 403-410, vol. 215.
Altschul, S. et al., "Gapped BLAST and PSI-BLAST: a new generation of protein database search programs," Nucl. Acid Res., 1997, pp. 3389-3402, vol. 25, No. 17, Oxford University Press.
Anum, D. et al., "Measuring naturally acquired ex vivo IFN-gamma responses to Plasmodium falciparum cell-traversal protein for ookinetes and sporozoites (CelTOS) in Ghanaian adults," Malar. J., 2015, pp. 1-8, vol. 14, No. 20.
Arnold, L. et al., "Further Improvements of the P. falciparum Humanized Mouse Model," PLoS One, Mar. 2011, pp. 1-12, vol. 6, No. 3, e18045.
Balu, B. et al., "High-efficiency transformation of Plasmodium falciparum by the lepidopteran transposable element piggyBac," PNAS, Nov. 2005, pp. 16391-16396, vol. 102, No. 45.
Balu, B. et al., "Functional genomics of Plasmodium falciparum through transposon-mediated mutagenesis," Cell Microbiol., 2006, pp. 1529-1536., vol. 8, No. 10.
Balu, B. et al., "piggyBac is an effective tool for functional analysis of the Plasmodium falciparum genome," BMC Microbiol., 2009, pp. 1-12, vol. 9, No. 83.
Balu, B. et al., "A Genetic Screen for Attenuated Growth Identifies Genes Crucial for Intraerythrocytic Development of Plasmodium falciparum," PLoS One, Oct. 2010, pp. 1-6, vol. 5, No. 10, e13282.
Bergmann-Leitner, E. et al., "Immunization with Pre-Erythrocytic Antigen CelTOS from Plasmodium falciparum Elicits Cross-Species Protection against Heterologous Challenge with Plasmodium berghei," PLoS One, Aug. 2010, pp. 1-9, vol. 5, No. 8, e12294.
Bergmann-Leitner, E. et al., "Cellular and humoral immune effector mechanisms required for sterile protection against sporozoite challenge induced with the novel malaria vaccine candidate CelTOS," Vaccine, 2011, pp. 5940-5949, vol. 29.
Brigham, K. et al., "Expression of a Prokaryotic Gene in Cultured Lung Endothelial Cells after Lipofection with a Plasmid Vector," Am. J. Resp. Cell. Mol. Biol., 1989, pp. 95-100, vol. 1.
Campbell, J., "In vitro culture of Plasmodium falciparum," J. Parasitol., Dec. 1984, p. 966, vol. 70, No. 6.
Chavalitshewinkoon, P. et al., "A Simple Technique for Large Scale in Vitro Culture of Plasmodium Falciparum," Southeast Asian J. Trop. Med. Public Health, Dec. 1991, pp. 544-547, vol. 22, No. 4.
Chaves, B. et al., "Plasmodium vivax Cell Traversal Protein for Ookinetes and Sporozoites (PvCelTOS) gene sequence and potential epitopes are highly conserved among isolates from different regions of Brazilian Amazon," PLoS Negl Trop Dis., Feb. 2017, pp. 1-19, vol. 11, No. 2, e0005344.
Chen, E. et al., Structural and functional basis for inhibition of erythrocyte invasion by antibodies that target Plasmodium falciparum EBA-175, PLoS Pathog., May 2013, pp. 1-12, vol. 9, No. 5, e1003390.
Chen, E. et al., "Structural analysis of the synthetic Duffy Binding Protein (DBP) antigen DEKnull relevant for Plasmodium vivax malaria vaccine design," PLoS Negl Trop Dis., 2015, pp. 1-6, vol. 9, No. 3, e0003644.
Chen, E. et al., "Broadly neutralizing epitopes in the Plasmodium vivax vaccine candidate Duffy Binding Protein," PNAS, May 2016, pp. 6277-6282, vol. 113, No. 22.
Chothia, C. et al., "Canonical Structures for the Hypervariable Regions of Immunoglobulins," J. Mol. Biol., 1987, pp. 901-917, vol. 196.
Chothia, C. et al., "Conformations of immunoglobulin hypervariable regions," Nature, Dec. 1989, pp. 877-883, vol. 342.
Churcher, T. et al., "Measuring the blockade of malaria transmission—An analysis of the Standard Membrane Feeding Assay," Int. J. Parasitol., 2012, pp. 1037-1044, vol. 42, No. 11.
Co, M. et al., "Humanized antibodies for antiviral therapy," PNAS, Apr. 1991, pp. 2869-2873, vol. 88.
Correia, B. et al., "Proof of principle for epitope-focused vaccine design," Nature, Mar. 2014, pp. 201-206, vol. 507, No. 7491.
Crompton, P. et al., "Advances and challenges in malaria vaccine development," J. Clin. Invest., 2010, pp. 4168-4178, vol. 120, No. 12.
Curtidor, H. et al., "Functional, Immunological and Three-Dimensional Analysis of Chemically Synthesised Sporozoite Peptides as Components of a Fully-Effective Antimalarial Vaccine," Curr. Med. Chem., 2011, pp. 4470-4502, vol. 18, No. 29, Bentham Science Publishers.
Dondorp, A. et al., "The threat of artemisinin-resistant malaria," N. Engl. J. Med., Sep. 2011, pp. 1073-1075, vol. 365, No. 12.
Dormitzer, P. et al., "Structural vaccinology starts to deliver," Nat. Rev. Microbiol., Dec. 2012, pp. 807-813, vol. 10.
Duffier, Y. et al., "A humanized mouse model for sequestration of Plasmodium falciparum sexual stages and in vivo evaluation of gametocytidal drugs," Sci. Rep., 2016, pp. 1-9, vol. 6, No. 35025.
Emsley, P. et al., "Coot: model-building tools for molecular graphics," Acta Cryst. D Biol. Cryst., 2004, pp. 2126-2132, vol. D60.
Espinosa, D. et al., "The Plasmodium falciparum Cell-Traversal Protein for Ookinetes and Sporozoites as a Candidate for Preerythrocytic and Transmission-Blocking Vaccines," Infect. Immun., Feb. 2017, pp. 1-10, vol. 85, No. 2, e00498-16.
Felgner, P. et al., "Lipofection: A highly efficient, lipid-mediated DNA-transfection procedure, " PNAS, Nov. 1987, pp. 7413-7417, vol. 84.
Ferraro, B. et al., "Inducing humoral and cellular responses to multiple sporozoite and liver-stage malaria antigens using exogenous plasmid DNA," Infect. Immun., Oct. 2013, pp. 3709-3720, vol. 81, No. 10.
Hall, B. et al., "Malaria Control, Elimination, and Eradication: The Role of the Evolving Biomedical Research Agenda," J. Infect. Dis., 2009, pp. 1639-1643, vol. 200, No. 11.
Huang, Y-M. et al., "Domestic trends in malaria research and development in China and its global influence," Infect. Dis. Poverty, 2017, pp. 1-9, vol. 6, No. 4.
International Search Report and Written Opinion dated Mar. 9, 2018 from related Patent Application No. PCT/US2017/059589; 15 pgs.
Ito, M et al., "NOD/SCID/gamma(c)(null) mouse: an excellent recipient mouse model for engraftment of human cells," Blood, Nov. 2002, pp. 3175-3182, vol. 100, No. 9.
Jimah, J. et al., "Malaria parasite CelTOS targets the inner leaflet of cell membranes for pore-dependent disruption," eLife, 2016, pp. 1-17, vol. 5, e20621.
Juliano, J. et al., "Pooled Amplicon Deep Sequencing of Candidate Plasmodium falciparum Transmission-Blocking Vaccine Antigens," Am. J. Trop. Med. Hyg., 2016, pp. 143-146, vol. 94, No. 1.
Kabsch, W., "Xds," Acta Cryst. D Biol. Cryst., 2010, pp. 125-132, vol. D66.

(56) References Cited

OTHER PUBLICATIONS

Kariu, T. et al., "CelTOS, a novel malarial protein that mediates transmission to mosquito and vertebrate hosts," Mol. Microbiol., 2006, pp. 1369-1379, vol. 59, No. 5.

Karlin, S. et al., "Methods for assessing the statistical significance of molecular sequence features by using general scoring schemes," PNAS, Mar. 1990, 2264-2268, vol. 87.

Krissinel, E. et al., "Inference of Macromolecular Assemblies from Crystalline State," J. Mol. Biol., 2007, pp. 774-797, vol. 372.

Lee, S-M. et al., "Assessment of Pfs25 expressed from multiple soluble expression platforms for use as transmission-blocking vaccine candidates," Malar. J., 2016, pp. 1-12, vol. 15, No. 405.

Lyke, K. et al., "Attenuated PfSPZ Vaccine induces strain-transcending T cells and durable protection against heterologous controlled human malaria infection," PNAS, Mar. 2017, pp. 2711-2716, vol. 114, No. 10.

Marcatili, P. et al., "PIGS: automatic prediction of antibody structures," Bioinformatics, 2008, pp. 1953-1954, vol. 24, No. 17.

McCoy, A. et al., "Phaser crystallographic software," J. Appl. Cryst., 2007, pp. 658-674., vol. 40.

Miura, K. et al., "Functional Comparison of Plasmodium falciparum Transmission-Blocking Vaccine Candidates by the Standard Membrane-Feeding Assay," Infect. Immun., Dec. 2013, pp. 4377-4382, vol. 81, No. 12.

Miura, K. et al., "Transmission-blocking activity is determined by transmission-reducing activity and number of control pocysts in Plasmodium falciparum standard membrane-feeding assay," Vaccine, 2016, pp. 4145-4151, vol. 34.

Moreno, A. et al., "Plasmodium falciparum-infected mice: more than a tour de force," Trends Parasitol., 2007, pp. 254-259, vol. 23, No. 6.

Mulligan, R., "The Basic Science of Gene Therapy," Sci., May 1993, pp. 926-932, vol. 260, No. 5110.

Livingstone, In vitro and in vivo inhibition of malaria parasite infection by monoclonal antibodies against Plasmodium falciparum circumsporozoite protein (CSP), Nature/Scientific Reports, 2021, 11:5318, 15 pp.

Barry, Functional antibodies against Plasmodium falciparum sporozoites are associated with a longer time to qPCR-detected infection among schoolchildren in Burkina Faso, Wellcome Open Research, May 15, 2019, 3:159, 40 pp.

Campo, RTS,S Vaccination Is Associated With Serologic Evidence of Decreased Exposure to Plasmodium falciparum Liver- and Blood-Stage Parasites, Molecular & Cellular Proteomics, 2015, 14.3, 13 pp, The American Society for Biochemistry and Molecular Biology, Inc.

Bergmann-Leitner, Immunization with Pre-Erythrocytic Antigen CelTOS from Plasmodium falciparum Elicits Cross-Species Protection against Heterologous Challenge with Plasmodium berghei, PLoS One, Aug. 2010, vol. 5, Iss. 8, 9 pp.

Bergmann-Leitner, Immunization with Pre-Erythrocytic Antigen CelTOS from Plasmodium falciparum Elicits Cross-Species Protection against Heterologous Challenge with Plasmodium berghei, PLoS One, Aug. 2010, vol. 5, Issue 8, pp. 1-9.

* cited by examiner

SEQUENCE LISTING

<160> NUMBER OF SEQ ID NOS: 82

<210> SEQ ID NO 1
<211> LENGTH: 184
<212> TYPE: PRT
<213> ORGANISM: Plasmodium falciparum

<400> SEQUENCE: 1

```
Met Asn Ala Leu Arg Arg Leu Pro Val Ile Cys Ser Phe Leu Val Phe
1               5                   10                  15

Phe Leu Val Phe Ser Asn Val Leu Cys Phe Arg Gly Asn Asn Gly His
                20                  25                  30

His Asn Ser Ser Ser Ser Leu Tyr Asn Gly Ser Gln Phe Ile Glu Gln
            35                  40                  45

Leu Asn Asn Ser Phe Thr Ser Ala Phe Leu Glu Ser Gln Ser Met Asn
        50                  55                  60

Lys Ile Gly Asp Asp Leu Ala Glu Thr Ile Ser Asn Glu Leu Val Ser
65                  70                  75                  80
```

```
Val Leu Gln Lys Asn Ser Pro Thr Phe Leu Glu Ser Ser Phe Asp Ile
                85                  90                  95

Lys Ser Glu Val Lys Lys His Ala Lys Ser Met Leu Lys Glu Leu Ile
            100                 105                 110

Lys Val Gly Leu Pro Ser Phe Glu Asn Leu Val Ala Glu Asn Val Lys
        115                 120                 125

Pro Pro Lys Val Asp Pro Ala Thr Tyr Gly Ile Ile Val Pro Val Leu
    130                 135                 140

Thr Ser Leu Phe Asn Lys Val Glu Thr Ala Val Gly Ala Lys Val Ser
145                 150                 155                 160

Asp Glu Ile Trp Asn Tyr Asn Ser Pro Asp Val Ser Glu Ser Glu Glu
                165                 170                 175

Ser Leu Ser Asp Asp Phe Phe Asp
            180

<210> SEQ ID NO 2
<211> LENGTH: 184
<212> TYPE: PRT
<213> ORGANISM: Plasmodium vivax

<400> SEQUENCE: 2

Met Asn Lys Val Asn Arg Ser Ile Ile Cys Ala Phe Leu Ala Leu Phe
1               5                   10                  15

Cys Phe Val Asn Val Leu Ser Leu Arg Gly Lys Ser Gly Ser Thr Ala
            20                  25                  30

Ser Ser Ser Leu Glu Gly Gly Ser Glu Phe Ser Glu Arg Ile Gly Asn
        35                  40                  45

Ser Leu Ser Ser Phe Leu Ser Glu Ser Ala Ser Leu Glu Val Ile Gly
    50                  55                  60

Asn Glu Leu Ala Asp Asn Ile Ala Asn Glu Ile Val Ser Ser Leu Gln
65                  70                  75                  80

Lys Asp Ser Ala Ser Phe Leu Gln Ser Gly Phe Asp Val Lys Thr Gln
                85                  90                  95

Leu Lys Ala Thr Ala Lys Lys Val Leu Val Glu Ala Leu Lys Ala Ala
            100                 105                 110

Leu Glu Pro Thr Glu Lys Ile Val Ala Ser Thr Ile Lys Pro Pro Arg
        115                 120                 125

Val Ser Glu Asp Ala Tyr Phe Leu Leu Gly Pro Val Val Lys Thr Leu
    130                 135                 140

Phe Asn Lys Val Glu Asp Val Leu His Lys Pro Ile Pro Asp Thr Ile
145                 150                 155                 160

Trp Glu Tyr Glu Ser Lys Gly Ser Leu Glu Glu Glu Glu Ala Glu Asp
                165                 170                 175

Glu Phe Ser Asp Glu Leu Leu Asp
            180

<210> SEQ ID NO 3
<211> LENGTH: 185
<212> TYPE: PRT
<213> ORGANISM: Plasmodium knowlesi

<400> SEQUENCE: 3

Met Asn Lys Val Asn Arg Val Ser Ile Ile Cys Ala Phe Leu Ala Leu
1               5                   10                  15

Phe Cys Phe Val Asn Val Leu Ser Leu Arg Gly Lys Ser Gly Leu Thr
            20                  25                  30
```

Ala Ser Ser Ser Leu Glu Gly Gly Ser Glu Phe Ser Glu Arg Ile Gly
            35                  40                  45

Asn Thr Leu Ser Ser Phe Leu Ser Glu Ser Ala Ser Leu Glu Val Ile
 50                  55                  60

Gly Asn Glu Leu Ala Asp Asn Ile Ala Asn Glu Ile Val Gly Ser Leu
 65                  70                  75                  80

Gln Asn Asp Ser Ala Ser Phe Leu Gln Ser Glu Phe Asp Val Lys Ala
                85                  90                  95

Gln Leu Lys Ala Thr Ala Lys Lys Val Leu Thr Glu Ala Leu Lys Ala
            100                 105                 110

Ala Leu Glu Pro Thr Glu Lys Ile Val Ala Ser Thr Ile Lys Pro Pro
        115                 120                 125

Arg Ile Lys Glu Asp Ile Tyr Phe Leu Leu Ser Pro Val Val Arg Ser
130                 135                 140

Leu Phe Asn Lys Val Glu Asp Val Leu His Lys Pro Val Ser Asp Asp
145                 150                 155                 160

Ile Trp Asn Tyr Glu Ser Arg Gly Ser Ser Glu Glu Glu Asp Glu
                165                 170                 175

Val Asp Ser Asp Glu Asp Phe Leu Asp
            180                 185

<210> SEQ ID NO 4
<211> LENGTH: 173
<212> TYPE: PRT
<213> ORGANISM: Bebesia microti

<400> SEQUENCE: 4

Met Lys Leu Ala Thr Pro Phe Leu Val Leu Thr Ala Leu Asn Ile Val
 1               5                  10                  15

Ile Leu His Ala Arg Arg Val Glu Arg Gly Tyr Pro Ser Asp Val Thr
             20                  25                  30

Lys Ala His Asp Tyr Asn Leu Lys Arg Ala Ile Arg Ser Glu Leu Glu
         35                  40                  45

Thr Ala Ser Asp Gln Ile Val Glu Ile Ala Gln His Val Glu Lys
 50                  55                  60

Ile Leu Gln Glu Gln Ser Pro Asp Glu Thr Ser Phe Ile Gln Asp Gly
 65                  70                  75                  80

Trp Lys Ser Thr Ala Lys Lys Ile Thr Lys Asn Ala Val Val His Ile
                 85                  90                  95

Ala Lys Asn Thr Ile Pro Val Ile Ala Ala Ile Val Ala Asp Ser Val
            100                 105                 110

Lys Pro Pro Asn Thr Asp Val Ile Val Tyr Asn Ser Leu Phe Lys Pro
        115                 120                 125

Val Cys Lys Asp Ile Phe Asp His Val Ser Ala Lys Leu Asp Ile Lys
130                 135                 140

Pro Asp Asp Ser Ile Trp Glu Tyr Ser Gly Asp Asp Gly Tyr Glu Asp
145                 150                 155                 160

Glu Asp Glu Asn Glu Asn Glu Glu Asp Asp Glu Phe Ile
                165                 170

<210> SEQ ID NO 5
<211> LENGTH: 192
<212> TYPE: PRT
<213> ORGANISM: Theileria parva

<400> SEQUENCE: 5

```
Met Val Leu Lys Met Asn Ser Ala Leu Ile Phe Phe Phe Leu Phe Phe
1               5                   10                  15

Lys Ala Ala Glu Ser His Lys Tyr Arg Val Asn Phe Leu Gly Pro Ser
            20                  25                  30

Lys Lys Ser Ser Phe Val Glu Lys Ser Asn Val Glu Lys Leu Thr Lys
        35                  40                  45

Val Leu Arg Glu Asp Leu Asn Ser Lys Val Asp Glu Val Val Asp Leu
    50                  55                  60

Ile Ala Thr Asp Leu Glu Arg Glu Leu Leu Lys Asn Gly Leu Thr Asn
65                  70                  75                  80

Leu Ser Leu Met Gln Gln Ser Asp Val Lys Gly Phe Gly Ser Lys Ala
                85                  90                  95

Lys Glu Ile Ile Lys Lys Thr Leu Val Gly Val Met Arg Ser Leu Leu
            100                 105                 110

Pro Val Phe Glu Arg Trp Ile His Asp Ser Val Gln Pro Pro Val Val
        115                 120                 125

Asp Lys His Val Tyr Gly Val Leu Ile His Pro Ile Gly Tyr Arg Ile
    130                 135                 140

Cys Glu Gln Ile His Glu Lys Leu Lys Ile Ser Glu Pro Asn Pro Trp
145                 150                 155                 160

Lys Asp Asp Glu Ile Glu Glu Glu Glu Glu Pro Glu Glu Glu Gln Asp
                165                 170                 175

Glu Gly Asp Ser Val Ser Asp Glu Ala Ile Asp Gln Leu Leu Thr Met
            180                 185                 190
```

<210> SEQ ID NO 6
<211> LENGTH: 325
<212> TYPE: PRT
<213> ORGANISM: Cytauxzoon felis

<400> SEQUENCE: 6

```
Met Lys Ile Tyr Leu Leu Leu Thr Asn Pro Asn Ile Leu Asn Ser Asn
1               5                   10                  15

Thr Ser Ile Ser Leu Leu Gln Lys Pro Ser Val Glu Glu Leu Arg Glu
            20                  25                  30

Val Ile Lys Arg Asp Leu Gly Ala Lys Val Gly Glu Val Val Glu Leu
        35                  40                  45

Leu Ala Thr Asp Leu Glu Lys Ala Leu Thr Asp Asn Asn Leu Leu Ala
    50                  55                  60

Ala Pro Ser Tyr Leu Gln Arg Ser Glu Gln Leu Glu Lys Val Lys Val
65                  70                  75                  80

Leu Val Lys Ser Thr Phe Ile Lys Val Leu Arg His Val Leu Pro Ile
                85                  90                  95

Leu Glu Leu Trp Val His Glu Ser Leu Leu Pro Pro Lys Val Ser Lys
            100                 105                 110

Leu Ile Tyr Asn Ser Ile Val Gln Pro Ile Cys Phe Ser Ile Thr Glu
        115                 120                 125

Glu Leu Asn Asn Lys Leu Lys Ile Thr Ala Gly Asn Pro Trp Lys Lys
    130                 135                 140

Asp Val Glu Glu Glu Asp Asp Gly Leu Gly Asp Leu Asp Leu Gly Gly
145                 150                 155                 160

Gly Gly Glu Asp Leu Asp Val Phe Asp Ile Asp Ile Cys Ser Tyr Cys
                165                 170                 175

Asp Ile Ser Ile Met Met Cys Gly Val Gln Thr Arg Pro Ala Cys Val
```

```
                    180                 185                 190
Phe Glu Asp Arg Phe Leu Val Arg Ser Ile Asp Asn Ser Lys Phe Glu
                195                 200                 205

Arg Val Ser Arg Ile Asn Ala Lys Ser Thr Gly Phe Asp Ala Glu Leu
            210                 215                 220

Leu Leu Asp Val Asn Ser Asp Ile Leu Pro Val Asn Asn Lys Ser Met
225                 230                 235                 240

Leu His Ile Leu Ile Thr Asn Ser Leu Leu Pro Ser Gly Thr Asp Ile
                245                 250                 255

Asn Leu Cys Glu Tyr Asn Asp Ile Pro Ser Leu Leu Gly Asp Tyr Glu
            260                 265                 270

Tyr Ala Met Tyr Gly Lys Ile Phe Lys Phe Glu Glu Val Ser Ser Glu
            275                 280                 285

Asn Arg Thr Ile Tyr Ala Ser Phe Gly Gly Leu Leu Met Ser Leu Thr
            290                 295                 300

Ala Asp Lys Gln Val Val Ala Asp Leu Glu Leu Gly Glu Leu Ile Tyr
305                 310                 315                 320

Phe Ala Leu Tyr Phe
                325

<210> SEQ ID NO 7
<211> LENGTH: 185
<212> TYPE: PRT
<213> ORGANISM: Plasmodium berghei

<400> SEQUENCE: 7

Met Asn Lys Leu Thr Lys Leu Ser Val Ile Ser Ser Val Phe Val Phe
1               5                   10                  15

Phe Cys Phe Phe Asn Val Leu Cys Leu Arg Gly Lys Asn Gly Ser Glu
            20                  25                  30

Met Ser Ser Phe Leu Glu Gly Gly Val Glu Ser Ser Asn Arg Ile Lys
        35                  40                  45

Lys Ser Leu Ala Ser Phe Ile Ser Glu Ser Ser Ser Leu Asp Asp Ile
    50                  55                  60

Gly Asn Gly Leu Ala Glu Thr Ile Thr Asn Glu Ile Phe Ser Ala Phe
65                  70                  75                  80

Gln Gln Asp Ser Ser Ser Phe Leu Gln Thr Lys Phe Asp Ile Lys Lys
                85                  90                  95

His Ile Lys Glu Asn Ala Lys Lys Val Leu Ile Glu Ala Ile Arg Leu
            100                 105                 110

Gly Leu Glu Pro Val Glu Lys Ile Val Ala Gln Ser Ile Gln Pro Pro
        115                 120                 125

Lys Val Asn Arg His Thr Tyr Ser Leu Val Ser Pro Val Val Lys Ala
    130                 135                 140

Leu Phe Asn Lys Ile Glu Glu Ala Val His Lys Pro Val Ser Asp Asn
145                 150                 155                 160

Ile Trp Asp Tyr Ala Gly Gly Asp Glu Tyr Glu Glu Thr Glu Glu
                165                 170                 175

Asp Asn Phe Asp Asn Asp Phe Phe Asn
            180                 185

<210> SEQ ID NO 8
<211> LENGTH: 179
<212> TYPE: PRT
<213> ORGANISM: Plasmodium reichenowi
```

```
<400> SEQUENCE: 8

Met Asn Ala Leu Arg Arg Leu Pro Val Ile Cys Ser Phe Leu Val Phe
1               5                   10                  15

Ser Asn Val Leu Cys Phe Arg Gly Asn Asn Gly His His Ser Ser Ser
            20                  25                  30

Ser Leu Tyr Asn Gly Ser Gln Phe Ile Glu Gln Leu Asn Asn Ser Phe
        35                  40                  45

Thr Ser Ala Phe Leu Glu Ser Gln Ser Met Asn Lys Ile Gly Asp Asp
    50                  55                  60

Leu Ala Glu Thr Ile Ser Asn Glu Leu Val Ser Val Leu Gln Lys Asn
65                  70                  75                  80

Ser Pro Thr Phe Leu Glu Ser Ser Phe Asp Ile Lys Ser Glu Val Lys
                85                  90                  95

Lys His Ala Lys Leu Met Leu Lys Glu Leu Ile Lys Val Gly Leu Pro
            100                 105                 110

Ser Val Glu Lys Leu Val Ala Glu Asn Val Lys Pro Pro Lys Val Asp
        115                 120                 125

Pro Ala Thr Tyr Gly Ile Ile Val Pro Val Leu Ser Ser Leu Phe Asn
    130                 135                 140

Lys Val Glu Thr Ala Val Gly Ala Asn Val Pro Asp Asp Ile Trp Asn
145                 150                 155                 160

Tyr Asn Ser Ser Asp Leu Ser Glu Ser Glu Glu Asn Leu Ser Asp Asp
                165                 170                 175

Phe Phe Asp

<210> SEQ ID NO 9
<211> LENGTH: 184
<212> TYPE: PRT
<213> ORGANISM: Plasmodium chabaudi

<400> SEQUENCE: 9

Met Asn Lys Leu Thr Lys Leu Ser Val Ile Ser Ser Val Leu Val Phe
1               5                   10                  15

Phe Cys Phe Phe Asn Val Leu Cys Leu Arg Gly Lys Asn Gly Ser Glu
            20                  25                  30

Met Ser Ser Ser Leu Glu Gly Gly Val Glu Ser Ala Ile Arg Ile Lys
        35                  40                  45

Asn Ser Leu Glu Ser Phe Ile Ser Glu Ser Ala Ser Leu Asp Asp Ile
    50                  55                  60

Gly Asn Gly Leu Ala Glu Thr Ile Thr Asn Glu Ile Phe Ser Ala Val
65                  70                  75                  80

Gln Gln Asp Ser Ser Ser Phe Leu Gln Thr Gln Phe Asp Ile Lys Lys
                85                  90                  95

His Ile Lys Glu Asn Ala Lys Lys Val Leu Ile Glu Ala Ile Arg Leu
            100                 105                 110

Gly Leu Glu Pro Val Glu Lys Ile Val Ala Lys Ser Ile Gln Pro Pro
        115                 120                 125

Lys Ile Asn Arg His Thr Tyr Ser Leu Val Ser Pro Val Val Lys Ser
    130                 135                 140

Leu Phe Asn Lys Ile Glu Glu Ala Val His Lys Pro Val Ser Asp Ser
145                 150                 155                 160

Ile Trp Glu Tyr Glu Gly Gly Glu Tyr Asp Glu Ser Glu Glu Asp
                165                 170                 175

Asn Tyr Glu Asp Glu Leu Phe Asn
```

<210> SEQ ID NO 10
<211> LENGTH: 185
<212> TYPE: PRT
<213> ORGANISM: Plasmodium yoelii

<400> SEQUENCE: 10

Met Asn Lys Leu Thr Lys Leu Ser Val Ile Ser Ser Val Leu Val Phe
1               5                   10                  15

Phe Cys Phe Phe Asn Val Leu Cys Leu Arg Gly Lys Asn Gly Ser Glu
                20                  25                  30

Met Ser Lys Phe Leu Glu Gly Gly Val Glu Ser Ser Asn Arg Ile Lys
            35                  40                  45

Asn Ser Leu Ser Ser Phe Ile Ser Glu Ser Ala Ser Leu Asp Asp Ile
        50                  55                  60

Gly Asn Gly Leu Ala Glu Thr Ile Thr Asn Glu Ile Phe Ser Ala Phe
65                  70                  75                  80

Gln Gln Asp Ser Ser Ser Phe Leu Gln Thr Gln Phe Asp Ile Lys Lys
                85                  90                  95

His Ile Lys Glu Asn Ala Lys Lys Val Leu Ile Glu Ala Ile Arg Leu
            100                 105                 110

Gly Leu Glu Pro Val Glu Lys Ile Val Ala Lys Ser Ile Gln Pro Pro
        115                 120                 125

Lys Val Asn Arg His Thr Tyr Ser Leu Val Ser Pro Ile Val Lys Ala
130                 135                 140

Leu Phe Asn Lys Ile Glu Asp Ala Val His Lys Pro Val Asn Asp Asn
145                 150                 155                 160

Ile Trp Glu Tyr Glu Gly Gly Asp Glu Glu Tyr Asp Glu Asn Glu Glu
                165                 170                 175

Glu Asn Phe Asp Asn Asp Phe Phe Asn
            180                 185

<210> SEQ ID NO 11
<211> LENGTH: 186
<212> TYPE: PRT
<213> ORGANISM: Plasmodium fragile

<400> SEQUENCE: 11

Met Asn Lys Val Asn Arg Val Ser Ile Ile Cys Ala Phe Leu Ala Leu
1               5                   10                  15

Phe Cys Phe Ala Asn Val Leu Ser Leu Arg Gly Lys Ser Gly Ser Thr
                20                  25                  30

Ala Ser Ser Ser Leu Glu Gly Gly Ser Glu Phe Ala Glu Arg Ile Gly
            35                  40                  45

Asn Ser Leu Ser Ser Phe Leu Ser Glu Ser Ala Ser Met Glu Val Ile
        50                  55                  60

Gly Asn Glu Leu Ala Asp Asn Ile Ala Asn Glu Ile Val Ser Ser Leu
65                  70                  75                  80

Gln Lys Asp Ser Ala Ser Phe Leu Gln Ser Gly Phe Asp Val Lys Ala
                85                  90                  95

Gln Leu Lys Ala Ala Thr Ala Lys Lys Val Leu Thr Glu Ala Leu Arg
            100                 105                 110

Ala Ala Leu Glu Pro Thr Glu Lys Ile Val Ala Ser Thr Ile Lys Pro
        115                 120                 125

Pro Arg Ile Thr Glu Glu Ala Tyr Phe Leu Leu Gly Pro Val Val Lys

```
                130                 135                 140
Thr Leu Phe Asn Lys Val Glu Asp Val Leu His Lys Pro Ile Pro Asp
145                 150                 155                 160

Asn Ile Trp Glu Tyr Glu Ser Ala Gly Ser Glu Glu Glu Glu Glu Ala
                165                 170                 175

Glu Asp Asp Phe Ser Asp Glu Phe Leu Asp
            180                 185

<210> SEQ ID NO 12
<211> LENGTH: 185
<212> TYPE: PRT
<213> ORGANISM: Plasmodium inui

<400> SEQUENCE: 12

Met Asn Lys Val Asn Arg Val Ser Ile Ile Cys Ala Phe Leu Ala Leu
1               5                   10                  15

Glu Cys Phe Val Asn Val Leu Ser Leu Arg Gly Lys Ser Gly Ser Thr
                20                  25                  30

Ala Ser Ser Ser Leu Glu Gly Gly Ser Glu Phe Ser Glu Arg Ile Gly
            35                  40                  45

Asn Ser Leu Ser Ser Phe Leu Ser Glu Ser Thr Ser Leu Glu Val Ile
50                  55                  60

Gly Asn Glu Leu Ala Asp Asn Ile Ala Asn Glu Ile Leu Asn Ser Leu
65                  70                  75                  80

Gln Lys Asp Ser Ala Ser Phe Leu Gln Ser Gly Phe Asp Val Lys Ser
                85                  90                  95

Gln Leu Lys Thr Thr Ala Lys Lys Val Leu Glu Ala Leu Lys Ala
            100                 105                 110

Gly Leu Gly Pro Thr Glu Glu Ile Ile Ala Ser Ser Ile Lys Pro Pro
            115                 120                 125

Arg Met Ser Glu Glu Lys Tyr Ser Phe Leu Gly Pro Val Leu Lys Ser
130                 135                 140

Leu Phe Asn Lys Ile Glu Asp Ala Leu His Lys Pro Val Pro Asp Asp
145                 150                 155                 160

Ile Trp Asp Tyr Lys Ser Glu Tyr Phe Asn Glu Glu Lys Ser Glu
                165                 170                 175

Asp Asp Ile Ser Glu Asp Phe Leu Asp
            180                 185

<210> SEQ ID NO 13
<211> LENGTH: 184
<212> TYPE: PRT
<213> ORGANISM: Plasmodium vinckei

<400> SEQUENCE: 13

Met Asn Lys Leu Thr Lys Leu Ser Val Ile Ser Ser Ile Leu Val Phe
1               5                   10                  15

Phe Cys Phe Phe Asn Val Leu Cys Leu Arg Gly Lys Asn Gly Ser Glu
                20                  25                  30

Met Ser Ser Ser Leu Glu Gly Gly Val Glu Ser Ala Asn Arg Ile Lys
            35                  40                  45

Asn Ser Leu Ser Ser Phe Ile Ser Glu Ser Ala Ser Val Asp Gly Ile
50                  55                  60

Gly Asn Gly Leu Ala Glu Thr Ile Thr Asn Glu Ile Phe Ser Ala Phe
65                  70                  75                  80

Gln Gln Asp Ser Ala Ser Phe Leu Gln Thr Gln Phe Asp Ile Lys Lys
```

```
                85                  90                  95
His Ile Lys Glu Asn Ala Lys Lys Val Leu Ile Glu Ala Ile Arg Leu
            100                 105                 110

Gly Leu Glu Pro Ile Glu Lys Ile Val Ala Gln Ser Ile Gln Pro Pro
            115                 120                 125

Lys Val Asn Arg His Thr Tyr Ser Leu Val Ser Pro Val Val Lys Ala
        130                 135                 140

Leu Phe Asn Lys Ile Glu Glu Ala Val His Lys Pro Val Ser Asp Asn
145                 150                 155                 160

Ile Trp Glu Tyr Glu Gly Gly Asn Glu Glu Tyr Asp Glu Asn Glu Glu
                165                 170                 175

Glu Phe Asp Asn Asp Leu Phe Asn
            180
```

<210> SEQ ID NO 14
<211> LENGTH: 184
<212> TYPE: PRT
<213> ORGANISM: Plasmodium petteri

<400> SEQUENCE: 14

```
Met Asn Lys Leu Thr Lys Leu Ser Val Ile Ser Ser Val Leu Val Phe
1               5                   10                  15

Phe Cys Phe Phe Asn Val Leu Cys Leu Arg Gly Lys Asn Gly Ser Glu
                20                  25                  30

Met Ser Ser Ser Leu Glu Gly Gly Val Glu Ser Ala Asn Arg Ile Lys
            35                  40                  45

Asn Ser Leu Ala Ser Phe Ile Ser Glu Ser Ala Ser Val Asp Gly Ile
        50                  55                  60

Gly Asn Gly Leu Ala Glu Thr Ile Thr Asn Glu Ile Phe Ser Ala Phe
65                  70                  75                  80

Gln Gln Asp Ser Ala Ser Phe Val Gln Thr Gln Phe Asp Ile Lys Lys
                85                  90                  95

His Ile Lys Glu Asn Ala Lys Lys Val Leu Ile Glu Ala Ile Arg Leu
            100                 105                 110

Gly Leu Glu Pro Ile Glu Lys Ile Val Ala Gln Ser Ile Gln Pro Pro
            115                 120                 125

Lys Val Asn Arg His Thr Tyr Ser Leu Val Ser Pro Val Val Lys Ala
        130                 135                 140

Leu Phe Asn Lys Ile Glu Glu Ala Val His Lys Pro Val Ser Asp Asn
145                 150                 155                 160

Ile Trp Asp Tyr Glu Gly Gly Asn Glu Glu Tyr Glu Glu Ser Asp Glu
                165                 170                 175

Asp Ser Asp Asn Asp Leu Phe Asn
            180
```

<210> SEQ ID NO 15
<211> LENGTH: 178
<212> TYPE: PRT
<213> ORGANISM: Babesia bovis

<400> SEQUENCE: 15

```
Met Lys Phe Ile Ala Val Ala Phe Val Leu Phe Ala Lys Phe Ala Ser
1               5                   10                  15

Ala Phe Asn Thr Ser Lys Asn His Leu Ser Gln Arg Ala Ala Gly His
                20                  25                  30

Ser Val Asn Val Thr Thr Ala Gln Val Glu Lys Phe Arg Glu Leu Ile
```

```
        35                  40                  45

Lys Ala Asp Met Ala Gln Lys Val Asp Asp Leu Ile Glu Leu Ile Val
    50                  55                  60

Ser Asp Ile Glu Arg Ala Leu Val Glu Ala Asn Glu Thr His Pro Val
65                  70                  75                  80

Phe Leu Gln Asn Gly Val Asn Glu Asn Ile Lys Lys Ile Val Lys Thr
                85                  90                  95

Ala Val Met Ala Met Leu Lys His Leu Val Pro Ile Phe Glu Asn Trp
            100                 105                 110

Ile Ala Asp Ala Val Lys Pro Pro Val Thr Thr Pro Thr Val Tyr Gly
        115                 120                 125

Met Leu Val Arg Pro Ile Gly Lys Ser Ile Phe Asp Asn Ile Tyr Gly
    130                 135                 140

Lys Leu Lys Met Glu Pro Ser Lys Gln Trp Asp Thr Glu Asp Glu Met
145                 150                 155                 160

Asp Phe Gly Ser Phe Asp Asp Ser Glu Glu Ala Gly Ser Ser Asp Asp
                165                 170                 175

Ala Phe

<210> SEQ ID NO 16
<211> LENGTH: 187
<212> TYPE: PRT
<213> ORGANISM: Babesia bigemina

<400> SEQUENCE: 16

Met Lys Phe Leu Val Leu Leu Ser Ile Val Val Leu Lys Ser Ala Leu
1               5                   10                  15

Ala Leu Asn Thr Asn Phe Arg Asn Arg Lys Arg Asp Leu Pro Ser Arg
            20                  25                  30

Ser Ile Ser Val Asn Asp Thr Asp Val Glu Thr Tyr Leu Gln His Asp
        35                  40                  45

Ile Ser Thr Glu Phe Arg Asp Ile Val Arg Arg Asp Ile Ala Asp Lys
    50                  55                  60

Thr Asp Glu Leu Ile Ser Leu Ile Val Lys Asp Val Glu Lys Leu Ile
65                  70                  75                  80

Glu Gln Asn Asp Met Val Arg Pro Val Phe Leu Glu Asn Ala Leu Lys
                85                  90                  95

Glu Asn Ala Lys Arg Met Ile Lys Ser Gly Val Ile Ser Ile Val Lys
            100                 105                 110

His Met Val Pro Val Phe Glu Arg Trp Ile Val Glu Ala Ile Lys Pro
        115                 120                 125

Pro Val Thr Ser Gly Met Val Tyr Thr Ala Leu Val Lys Pro Ile Gly
    130                 135                 140

Lys Ser Ile Phe Asp Gln Leu Tyr His Lys Phe Asn Leu Pro Thr Ser
145                 150                 155                 160

Lys Ile Trp Asp Lys Tyr Asp Asp Asn Ile Asp Met Ser Phe Asp Glu
                165                 170                 175

Ala Glu Glu Asp Ala Glu Gly Glu Thr Asp Val
            180                 185

<210> SEQ ID NO 17
<211> LENGTH: 184
<212> TYPE: PRT
<213> ORGANISM: Theileria annulata

<400> SEQUENCE: 17
```

Phe Asn Cys Phe Ser Cys Asn Ser Thr Arg Arg Ser Leu Ile Phe Phe
1               5                   10                  15

Ile Phe Phe Lys Ala Ala Gln Ser His Lys Tyr Arg Pro Asn Phe Leu
            20                  25                  30

Gly Pro Ala Lys Lys Ser Ser Phe Val Glu Lys Ser Asn Val Glu Lys
            35                  40                  45

Leu Thr Lys Val Leu Arg Glu Asp Leu Asn Ser Lys Val Asp Glu Val
        50                  55                  60

Val Asp Leu Ile Ala Thr Asp Leu Glu Arg Glu Leu Leu Lys Asn Gly
65                  70                  75                  80

Leu Thr Asn Leu Ser Leu Met Gln Gln Ser Asp Ala Lys Ala Phe Gly
                85                  90                  95

Gly Lys Ala Lys Glu Ile Ile Lys Lys Thr Leu Ile Gly Val Met Arg
            100                 105                 110

Ser Leu Ile Pro Val Phe Glu Arg Trp Ile His Asp Ser Val Gln Pro
        115                 120                 125

Pro Val Val Asp Arg His Val Tyr Thr Val Leu Ile His Pro Ile Gly
        130                 135                 140

Tyr Arg Ile Cys Glu Gln Ile His Glu Lys Leu Lys Ile Asn Glu Pro
145                 150                 155                 160

Pro Trp Lys Asn Asp Glu Phe Ala Glu Glu Met Glu Glu Glu Glu Glu
                165                 170                 175

Glu Gly Asp Ser Ile Ser Asp Glu
            180

<210> SEQ ID NO 18
<211> LENGTH: 178
<212> TYPE: PRT
<213> ORGANISM: Theileria orientalis

<400> SEQUENCE: 18

Met Lys Phe Phe Leu Phe Val Val Thr Leu Leu Phe Ser Val Ala Gln
1               5                   10                  15

Ser His Lys Phe Arg Ala Asn Phe Leu Gly Pro Ser Lys Asn Ser Ser
            20                  25                  30

Phe Val Gln Lys Ala Ser Ile Glu Arg Leu Thr Lys Val Ile Arg Asp
            35                  40                  45

Asp Leu Asn Ser Lys Val Asp Glu Val Val Asp Leu Ile Ala Thr Asp
        50                  55                  60

Leu Glu Arg Glu Leu Leu Lys Gly Gly Leu Thr Asn Leu Ser Leu Leu
65                  70                  75                  80

Gln Gln Gly Asn Val Gly Gly Met Gly Ala Lys Ala Lys Gln Val Ile
                85                  90                  95

Lys Lys Thr Leu Val Gly Val Leu Lys Ser Val Val Pro Met Phe Glu
            100                 105                 110

Thr Trp Ile His Asp Ala Val Gln Pro Val Val Asp Arg Asn Val
        115                 120                 125

Tyr Ser Ala Leu Ile Gln Pro Val Gly Phe Gly Ile Ser Glu Gln Leu
        130                 135                 140

His Glu Lys Leu His Ile Asp Lys Pro Asn Pro Trp Lys Glu Asp Glu
145                 150                 155                 160

Leu Glu Glu Glu Glu Asp Glu Met Asp Glu Asp Gly Leu Leu Asp Asp
                165                 170                 175

Asp Asp

<210> SEQ ID NO 19
<211> LENGTH: 179
<212> TYPE: PRT
<213> ORGANISM: Theileria equi

<400> SEQUENCE: 19

Met Arg Ser Thr Phe Phe Phe Leu Phe Phe Ile Gly Ser Ala Leu Ser
1               5                   10                  15

His Arg Leu Arg Ser Asn Val Leu Ala Pro Ser Leu Tyr Thr Ser Phe
            20                  25                  30

Ser Gln Lys Thr Tyr Val Asp Arg Ile Ser Lys Ile Ile Arg Asn Asp
        35                  40                  45

Leu Asp Ser Lys Val Asp Glu Ile Val Asp Ile Leu Ala Ser Asp Leu
    50                  55                  60

Glu Lys Glu Leu Gly Lys Asn Gly Leu Leu Ala Ala Ser Tyr Leu Glu
65                  70                  75                  80

Thr Val Ser Gly Asn Gly Trp Ala Lys Gln Ala Lys Val Ile Val Lys
                85                  90                  95

Lys Thr Leu Leu Ser Ile Ile Lys Arg Met Ile Pro Leu Phe Asp Met
            100                 105                 110

Trp Ile His Asp Ala Val Gln Pro Pro Val Val Asp Arg Leu Val Tyr
        115                 120                 125

Lys Leu Leu Val His Pro Leu Gly Phe Gly Ile Ser Glu Glu Leu Arg
    130                 135                 140

Asn Lys Leu His Ile Thr Thr Glu Asn Pro Trp Lys Glu Asp Ala Ile
145                 150                 155                 160

Asp Asp Asp Asp Asp Phe Asp Thr Leu Gly Ala Asp Glu Asp Glu
                165                 170                 175

Glu Asp Glu

<210> SEQ ID NO 20
<211> LENGTH: 10
<212> TYPE: PRT
<213> ORGANISM: Artificial Sequence
<220> FEATURE:
<223> OTHER INFORMATION: 4H12 falciparum epitope

<400> SEQUENCE: 20

Gln Lys Asn Ser Pro Thr Phe Leu Glu Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: 4H12 vivax epitope

<400> SEQUENCE: 21

Gln Lys Asp Ser Ala Ser Phe Leu Gln Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: 4H12 knowlesi epitope

<400> SEQUENCE: 22

```
Gln Asn Asp Ser Ala Ser Phe Leu Gln Ser
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: 4H12 berghei epitope

<400> SEQUENCE: 23

```
Gln Gln Asp Ser Ser Ser Phe Leu Gln Thr
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: 4H12 yoelii epitope

<400> SEQUENCE: 24

```
Gln Gln Asp Ser Ser Ser Phe Leu Gln Thr
1               5                   10
```

<210> SEQ ID NO 25
<211> LENGTH: 13
<212> TYPE: PRT
<213> ORGANISM: Artificial Sequence
<220> FEATURE:
<223> OTHER INFORMATION: 4H12 microti epitope

<400> SEQUENCE: 25

```
Gln Glu Gln Ser Pro Asp Glu Thr Ser Phe Ile Gln Asp
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: 4H12 bovis epitope

<400> SEQUENCE: 26

```
Val Glu Ala Asn Glu Thr His Pro Val Phe Leu Gln Asn
1               5                   10
```

<210> SEQ ID NO 27
<211> LENGTH: 13
<212> TYPE: PRT
<213> ORGANISM: Artificial Sequence
<220> FEATURE:
<223> OTHER INFORMATION: 4H12 bigemena epitope

<400> SEQUENCE: 27

```
Glu Gln Asn Asp Met Val Arg Pro Val Phe Leu Glu Asn
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: 4H12 parva epitope

<400> SEQUENCE: 28

Leu Lys Asn Gly Leu Thr Asn Leu Ser Leu Met Gln Gln
1               5                   10

<210> SEQ ID NO 29
<211> LENGTH: 13
<212> TYPE: PRT
<213> ORGANISM: Artificial Sequence
<220> FEATURE:
<223> OTHER INFORMATION: 4H12 annulata epitope

<400> SEQUENCE: 29

Leu Lys Asn Gly Leu Thr Asn Leu Ser Leu Met Gln Gln
1               5                   10

<210> SEQ ID NO 30
<211> LENGTH: 13
<212> TYPE: PRT
<213> ORGANISM: Artificial Sequence
<220> FEATURE:
<223> OTHER INFORMATION: 4H12 orientalis epitope

<400> SEQUENCE: 30

Leu Lys Gly Gly Leu Thr Asn Leu Ser Leu Leu Gln Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: 4H12 equi epitope

<400> SEQUENCE: 31

Gly Lys Asn Gly Leu Leu Ala Ala Ser Tyr Leu Glu Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: 4H12  felis epitope

<400> SEQUENCE: 32

Thr Asp Asn Asn Leu Leu Ala Ala Pro Ser Tyr Leu Gln
1               5                   10

<210> SEQ ID NO 33
<211> LENGTH: 10
<212> TYPE: PRT
<213> ORGANISM: Artificial Sequence
<220> FEATURE:
<223> OTHER INFORMATION: 4H12 reichinowi epitope

<400> SEQUENCE: 33

Gln Lys Asn Ser Pro Thr Phe Leu Glu Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: 4H12 chaubadi epitope

<400> SEQUENCE: 34

Gln Gln Asp Ser Ser Ser Phe Leu Gln Thr

<210> SEQ ID NO 35
<211> LENGTH: 10
<212> TYPE: PRT
<213> ORGANISM: Artificial Sequence
<220> FEATURE:
<223> OTHER INFORMATION: 4H12 fragile epitope

<400> SEQUENCE: 35

Gln Lys Asp Ser Ala Ser Phe Leu Gln Ser
1               5                   10

<210> SEQ ID NO 36
<211> LENGTH: 10
<212> TYPE: PRT
<213> ORGANISM: Artificial Sequence
<220> FEATURE:
<223> OTHER INFORMATION: 4H12 inui epitope

<400> SEQUENCE: 36

Gln Lys Asp Ser Ala Ser Phe Leu Gln Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: 4H12 vinkei epitope

<400> SEQUENCE: 37

Gln Gln Asp Ser Ala Ser Phe Leu Gln Thr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: 4H12  petteri epitope

<400> SEQUENCE: 38

Gln Gln Asp Ser Ala Ser Phe Val Gln Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: 7G7  falciparum epitope

<400> SEQUENCE: 39

Ala Phe Leu Glu Ser Gln Ser Met Asn Lys Ile
1               5                   10

<210> SEQ ID NO 40
<211> LENGTH: 11
<212> TYPE: PRT
<213> ORGANISM: Artificial Sequence
<220> FEATURE:
<223> OTHER INFORMATION: 7G7 vivax epitope

<400> SEQUENCE: 40

Phe Leu Ser Glu Ser Ala Ser Leu Glu Val Ile
1               5                   10

```
<210> SEQ ID NO 41
<211> LENGTH: 11
<212> TYPE: PRT
<213> ORGANISM: Artificial Sequence
<220> FEATURE:
<223> OTHER INFORMATION: 7G7 knowlesi epitope

<400> SEQUENCE: 41

Phe Leu Ser Glu Ser Ala Ser Leu Glu Val Ile
1               5                   10

<210> SEQ ID NO 42
<211> LENGTH: 11
<212> TYPE: PRT
<213> ORGANISM: Artificial Sequence
<220> FEATURE:
<223> OTHER INFORMATION: 7G7 berghei epitope

<400> SEQUENCE: 42

Phe Ile Ser Glu Ser Ser Ser Leu Asp Asp Ile
1               5                   10

<210> SEQ ID NO 43
<211> LENGTH: 11
<212> TYPE: PRT
<213> ORGANISM: Artificial Sequence
<220> FEATURE:
<223> OTHER INFORMATION: 7G7 yoelii epitope

<400> SEQUENCE: 43

Phe Ile Ser Glu Ser Ala Ser Leu Asp Asp Ile
1               5                   10

<210> SEQ ID NO 44
<211> LENGTH: 9
<212> TYPE: PRT
<213> ORGANISM: Artificial Sequence
<220> FEATURE:
<223> OTHER INFORMATION: 7G7 microti epitope

<400> SEQUENCE: 44

Ala Ile Arg Ser Glu Leu Glu Thr Ala
1               5

<210> SEQ ID NO 45
<211> LENGTH: 9
<212> TYPE: PRT
<213> ORGANISM: Artificial Sequence
<220> FEATURE:
<223> OTHER INFORMATION: 7G7  bovis epitope

<400> SEQUENCE: 45

Leu Ile Lys Ala Asp Met Ala Gln Lys
1               5

<210> SEQ ID NO 46
<211> LENGTH: 9
<212> TYPE: PRT
<213> ORGANISM: Artificial Sequence
<220> FEATURE:
<223> OTHER INFORMATION: 7G7 bigemena epitope

<400> SEQUENCE: 46

Ile Val Arg Arg Asp Ile Ala Asp Lys
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: 7G7 parva epitope

<400> SEQUENCE: 47

Val Leu Arg Glu Asp Leu Asn Ser Lys
1               5

<210> SEQ ID NO 48
<211> LENGTH: 9
<212> TYPE: PRT
<213> ORGANISM: Artificial Sequence
<220> FEATURE:
<223> OTHER INFORMATION: 7G7 annulata epitope

<400> SEQUENCE: 48

Val Leu Arg Glu Asp Leu Asn Ser Lys
1               5

<210> SEQ ID NO 49
<211> LENGTH: 9
<212> TYPE: PRT
<213> ORGANISM: Artificial Sequence
<220> FEATURE:
<223> OTHER INFORMATION: 7G7 orientalis epitope

<400> SEQUENCE: 49

Val Ile Arg Asp Asp Leu Asn Ser Lys
1               5

<210> SEQ ID NO 50
<211> LENGTH: 9
<212> TYPE: PRT
<213> ORGANISM: Artificial Sequence
<220> FEATURE:
<223> OTHER INFORMATION: 7G7 equi epitope

<400> SEQUENCE: 50

Ile Ile Arg Asn Asp Leu Asp Ser Lys
1               5

<210> SEQ ID NO 51
<211> LENGTH: 9
<212> TYPE: PRT
<213> ORGANISM: Artificial Sequence
<220> FEATURE:
<223> OTHER INFORMATION: 7G7  felis epitope

<400> SEQUENCE: 51

Val Ile Lys Arg Asp Leu Gly Ala Lys
1               5

<210> SEQ ID NO 52
<211> LENGTH: 11
<212> TYPE: PRT
<213> ORGANISM: Artificial Sequence
<220> FEATURE:
<223> OTHER INFORMATION: 7G7 reichinowi epitope

<400> SEQUENCE: 52

Ala Phe Leu Glu Ser Gln Ser Met Asn Lys Ile
1               5                   10
```

```
<210> SEQ ID NO 53
<211> LENGTH: 11
<212> TYPE: PRT
<213> ORGANISM: Artificial Sequence
<220> FEATURE:
<223> OTHER INFORMATION: 7G7 chaubadi epitope

<400> SEQUENCE: 53

Phe Ile Ser Glu Ser Ala Ser Leu Asp Asp Ile
1               5                   10

<210> SEQ ID NO 54
<211> LENGTH: 11
<212> TYPE: PRT
<213> ORGANISM: Artificial Sequence
<220> FEATURE:
<223> OTHER INFORMATION: 7G7 fragile epitope

<400> SEQUENCE: 54

Phe Leu Ser Glu Ser Ala Ser Met Glu Val Ile
1               5                   10

<210> SEQ ID NO 55
<211> LENGTH: 11
<212> TYPE: PRT
<213> ORGANISM: Artificial Sequence
<220> FEATURE:
<223> OTHER INFORMATION: 7G7 inui epitope

<400> SEQUENCE: 55

Phe Leu Ser Glu Ser Thr Ser Leu Glu Val Ile
1               5                   10

<210> SEQ ID NO 56
<211> LENGTH: 11
<212> TYPE: PRT
<213> ORGANISM: Artificial Sequence
<220> FEATURE:
<223> OTHER INFORMATION: 7G7 vinkei epitope

<400> SEQUENCE: 56

Phe Ile Ser Glu Ser Ala Ser Val Asp Asp Ile
1               5                   10

<210> SEQ ID NO 57
<211> LENGTH: 11
<212> TYPE: PRT
<213> ORGANISM: Artificial Sequence
<220> FEATURE:
<223> OTHER INFORMATION: 7G7  petteri epitope

<400> SEQUENCE: 57

Phe Ile Ser Glu Ser Ala Ser Val Asp Asp Ile
1               5                   10

<210> SEQ ID NO 58
<211> LENGTH: 19
<212> TYPE: PRT
<213> ORGANISM: Artificial Sequence
<220> FEATURE:
<223> OTHER INFORMATION: 6C4  falciparum epitope

<400> SEQUENCE: 58

Thr Ser Leu Phe Asn Lys Val Glu Thr Ala Val Gly Ala Lys Val Ser
1               5                   10                  15

Asp Glu Ile
```

```
<210> SEQ ID NO 59
<211> LENGTH: 19
<212> TYPE: PRT
<213> ORGANISM: Artificial Sequence
<220> FEATURE:
<223> OTHER INFORMATION: 6C4 vivax epitope

<400> SEQUENCE: 59

Lys Thr Leu Phe Asn Lys Val Glu Asp Val Leu His Lys Pro Ile Pro
1               5                   10                  15

Asp Thr Ile

<210> SEQ ID NO 60
<211> LENGTH: 19
<212> TYPE: PRT
<213> ORGANISM: Artificial Sequence
<220> FEATURE:
<223> OTHER INFORMATION: 6C4 knowlesi epitope

<400> SEQUENCE: 60

Arg Ser Leu Phe Asn Lys Val Glu Asp Val Leu His Lys Pro Val Ser
1               5                   10                  15

Asp Asp Ile

<210> SEQ ID NO 61
<211> LENGTH: 19
<212> TYPE: PRT
<213> ORGANISM: Artificial Sequence
<220> FEATURE:
<223> OTHER INFORMATION: 6C4 berghei epitope

<400> SEQUENCE: 61

Lys Ala Leu Phe Asn Lys Ile Glu Glu Ala Val His Lys Pro Val Ser
1               5                   10                  15

Asp Asn Ile

<210> SEQ ID NO 62
<211> LENGTH: 19
<212> TYPE: PRT
<213> ORGANISM: Artificial Sequence
<220> FEATURE:
<223> OTHER INFORMATION: 6C4 yoelii epitope

<400> SEQUENCE: 62

Lys Ala Leu Phe Asn Lys Ile Glu Asp Ala Val His Lys Pro Val Asn
1               5                   10                  15

Asp Asn Ile

<210> SEQ ID NO 63
<211> LENGTH: 19
<212> TYPE: PRT
<213> ORGANISM: Artificial Sequence
<220> FEATURE:
<223> OTHER INFORMATION: 6C4 microti epitope

<400> SEQUENCE: 63

Lys Asp Ile Phe Asp His Val Ser Ala Lys Leu Asp Ile Lys Pro Asp
1               5                   10                  15

Asp Ser Ile

<210> SEQ ID NO 64
<211> LENGTH: 18
<212> TYPE: PRT
```

<213> ORGANISM: Artificial Sequence
<220> FEATURE:
<223> OTHER INFORMATION: 6C4 bovis epitope

<400> SEQUENCE: 64

Lys Ser Ile Phe Asp Asn Ile Tyr Gly Lys Leu Lys Met Glu Pro Ser
1 5 10 15

Lys Gln

<210> SEQ ID NO 65
<211> LENGTH: 18
<212> TYPE: PRT
<213> ORGANISM: Artificial Sequence
<220> FEATURE:
<223> OTHER INFORMATION: 6C4 bigemena epitope

<400> SEQUENCE: 65

Lys Ser Ile Phe Asp Gln Leu Tyr His Lys Phe Asn Leu Pro Thr Ser
1 5 10 15

Lys Ile

<210> SEQ ID NO 66
<211> LENGTH: 18
<212> TYPE: PRT
<213> ORGANISM: Artificial Sequence
<220> FEATURE:
<223> OTHER INFORMATION: 6C4 parva epitope

<400> SEQUENCE: 66

Tyr Arg Ile Cys Glu Gln Ile His Glu Lys Leu Lys Ile Ser Glu Pro
1 5 10 15

Asn Pro

<210> SEQ ID NO 67
<211> LENGTH: 18
<212> TYPE: PRT
<213> ORGANISM: Artificial Sequence
<220> FEATURE:
<223> OTHER INFORMATION: 6C4 annulata epitope

<400> SEQUENCE: 67

Tyr Arg Ile Cys Glu Gln Ile His Glu Lys Leu Lys Ile Asn Glu Pro
1 5 10 15

Asn Pro

<210> SEQ ID NO 68
<211> LENGTH: 18
<212> TYPE: PRT
<213> ORGANISM: Artificial Sequence
<220> FEATURE:
<223> OTHER INFORMATION: 7G7 orientalis epitope

<400> SEQUENCE: 68

Phe Gly Ile Ser Glu Gln Leu His Glu Lys Leu His Ile Asp Lys Pro
1 5 10 15

Asn Pro

<210> SEQ ID NO 69
<211> LENGTH: 18
<212> TYPE: PRT
<213> ORGANISM: Artificial Sequence
<220> FEATURE:
<223> OTHER INFORMATION: 6C4 equi epitope

```
<400> SEQUENCE: 69

Phe Gly Ile Ser Glu Glu Leu Arg Asn Lys Leu His Ile Thr Thr Glu
1               5                   10                  15

Asn Pro

<210> SEQ ID NO 70
<211> LENGTH: 19
<212> TYPE: PRT
<213> ORGANISM: Artificial Sequence
<220> FEATURE:
<223> OTHER INFORMATION: 6C4  felis epitope

<400> SEQUENCE: 70

Ser Ser Leu Phe Asn Lys Val Glu Thr Ala Val Gly Ala Asn Val Pro
1               5                   10                  15

Asp Asp Ile

<210> SEQ ID NO 71
<211> LENGTH: 19
<212> TYPE: PRT
<213> ORGANISM: Artificial Sequence
<220> FEATURE:
<223> OTHER INFORMATION: 6C4 reichinowi epitope

<400> SEQUENCE: 71

Lys Ser Leu Phe Asn Lys Ile Glu Glu Ala Val His Lys Pro Val Ser
1               5                   10                  15

Asp Ser Ile

<210> SEQ ID NO 72
<211> LENGTH: 19
<212> TYPE: PRT
<213> ORGANISM: Artificial Sequence
<220> FEATURE:
<223> OTHER INFORMATION: 6C4 chaubadi epitope

<400> SEQUENCE: 72

Lys Ser Leu Phe Asn Lys Ile Glu Glu Ala Val His Lys Pro Val Ser
1               5                   10                  15

Asp Ser Ile

<210> SEQ ID NO 73
<211> LENGTH: 19
<212> TYPE: PRT
<213> ORGANISM: Artificial Sequence
<220> FEATURE:
<223> OTHER INFORMATION: 6C4 fragile epitope

<400> SEQUENCE: 73

Lys Thr Leu Phe Asn Lys Val Glu Asp Val Leu His Lys Pro Ile Pro
1               5                   10                  15

Asp Asn Ile

<210> SEQ ID NO 74
<211> LENGTH: 19
<212> TYPE: PRT
<213> ORGANISM: Artificial Sequence
<220> FEATURE:
<223> OTHER INFORMATION: 6C4 inui epitope

<400> SEQUENCE: 74

Lys Ser Leu Phe Asn Lys Ile Glu Asp Ala Leu His Lys Pro Val Pro
1               5                   10                  15
```

Asp Asp Ile

<210> SEQ ID NO 75
<211> LENGTH: 19
<212> TYPE: PRT
<213> ORGANISM: Artificial Sequence
<220> FEATURE:
<223> OTHER INFORMATION: 6C4 vinkei epitope

<400> SEQUENCE: 75

Lys Ala Leu Phe Asn Lys Ile Glu Glu Ala Val His Lys Pro Val Ser
1               5                   10                  15

Asp Asn Ile

<210> SEQ ID NO 76
<211> LENGTH: 19
<212> TYPE: PRT
<213> ORGANISM: Artificial Sequence
<220> FEATURE:
<223> OTHER INFORMATION: 6C4 petteri epitope

<400> SEQUENCE: 76

Lys Ala Leu Phe Asn Lys Ile Glu Glu Ala Val His Lys Pro Val Ser
1               5                   10                  15

Asp Gly Ile

<210> SEQ ID NO 77
<211> LENGTH: 117
<212> TYPE: PRT
<213> ORGANISM: Artificial Sequence
<220> FEATURE:
<223> OTHER INFORMATION: 4H12 heavy chain variable region

<400> SEQUENCE: 77

Glu Val Gln Leu Gln Glu Ser Gly Pro Glu Leu Val Lys Pro Gly Ala
1               5                   10                  15

Ser Val Lys Ile Ser Cys Lys Ala Ser Gly Tyr Ala Leu Ser Ser Ser
                20                  25                  30

Trp Leu Asn Trp Val Lys Gln Arg Pro Gly Gln Gly Leu Glu Trp Ile
            35                  40                  45

Gly Arg Ile Phe Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Leu Gln Leu Ser Ser Leu Thr Ser Val Asp Ser Ala Val Tyr Phe Cys
                85                  90                  95

Ala Arg Gly Gly Thr Val Val Phe Asp Tyr Trp Gly Gln Gly Thr Thr
            100                 105                 110

Leu Thr Val Ser Ser
        115

<210> SEQ ID NO 78
<211> LENGTH: 105
<212> TYPE: PRT
<213> ORGANISM: Artificial Sequence
<220> FEATURE:
<223> OTHER INFORMATION: 4H12 light chain variable region

<400> SEQUENCE: 78

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Ile Ala
            20                  25                  30

Val Ala Trp Tyr Gln Gln Arg Pro Gly Gln Ser Pro Lys Leu Leu Ile
        35                  40                  45

Tyr Trp Ala Ser Lys Arg His Thr Gly Val His Asp Arg Phe Thr Gly
    50                  55                  60

Thr Gly Phe Gly Thr Asp Phe Thr Leu Thr Ile Ser Thr Val Gln Ser
65                  70                  75                  80

Glu Asp Leu Ala Asp Tyr Phe Cys Gln Gln Tyr Ser Asn Ser Leu Thr
                85                  90                  95

Phe Gly Ala Gly Thr Thr Leu Glu Leu
            100                 105

<210> SEQ ID NO 79
<211> LENGTH: 119
<212> TYPE: PRT
<213> ORGANISM: Artificial Sequence
<220> FEATURE:
<223> OTHER INFORMATION: 7G7 heavy chain variable region

<400> SEQUENCE: 79

Gln Leu Gln Glu Ser Gly Pro Glu Leu Val Lys Pro Gly Ala Ser Val
1               5                   10                  15

Lys Val Ser Cys Lys Ala Ser Gly Tyr Ser Phe Thr Asp Tyr Asn Met
            20                  25                  30

Tyr Trp Val Lys Gln Ser His Gly Lys Ser Leu Glu Trp Ile Gly Tyr
        35                  40                  45

Ile Asp Pro Tyr Asn Gly Gly Thr Arg Tyr Asn Gln Lys Phe Arg Asp
    50                  55                  60

Lys Ala Thr Leu Thr Val Asp Lys Ser Ser Thr Ala Phe Met His
65                  70                  75                  80

Leu Asn Ser Leu Thr Ser Glu Asp Ser Ala Val Tyr Tyr Cys Ala Arg
                85                  90                  95

Gly Tyr Tyr Tyr Gly Asn Pro Leu His Phe Asp Val Trp Gly Ala Gly
            100                 105                 110

Thr Thr Val Thr Val Ser Ser
        115

<210> SEQ ID NO 80
<211> LENGTH: 106
<212> TYPE: PRT
<213> ORGANISM: Artificial Sequence
<220> FEATURE:
<223> OTHER INFORMATION: 7G7 light chain variable region

<400> SEQUENCE: 80

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Ile
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Tyr Pro Ala Thr

```
                        85                  90                  95

Phe Gly Ala Gly Thr Lys Leu Glu Leu Lys
            100                 105

<210> SEQ ID NO 81
<211> LENGTH: 162
<212> TYPE: PRT
<213> ORGANISM: Artificial Sequence
<220> FEATURE:
<223> OTHER INFORMATION: 6C4 heavy chain variable region

<400> SEQUENCE: 81

Ala Ser Val Arg Leu Ser Cys Lys Ala Ser Gly Tyr Thr Phe Thr Asp
1               5                   10                  15

Tyr Tyr Ile Asn Trp Val Lys Gln Arg Thr Gly Gln Gly Leu Glu Trp
            20                  25                  30

Ile Gly Glu Ile Tyr Pro Gly Thr Gly Asn Thr Tyr Tyr Asn Glu Lys
        35                  40                  45

Phe Lys Asp Lys Ala Thr Leu Thr Ala Asp Thr Ser Ser Ser Thr Ala
50                  55                  60

Tyr Met Gln Leu Ser Ser Leu Thr Ser Glu Asp Ser Ala Val Tyr Phe
65                  70                  75                  80

Cys Ala Arg Lys Ile Tyr Tyr Tyr Gly Ile Ser Gly Tyr Ala Met Asp
                85                  90                  95

Tyr Trp Gly Gln Gly Thr Ser Val Thr Val Ser Ser Ala Lys Thr Thr
            100                 105                 110

Pro Pro Ser Val Tyr Pro Leu Ala Pro Gly Ser Ala Ala Gln Thr Asn
        115                 120                 125

Ser Met Val Thr Leu Gly Cys Leu Val Lys Gly Tyr Phe Pro Glu Pro
130                 135                 140

Val Thr Val Thr Trp Asn Ser Gly Ser Leu Ser Ser Gly Val Ala Thr
145                 150                 155                 160

Phe Gln

<210> SEQ ID NO 82
<211> LENGTH: 105
<212> TYPE: PRT
<213> ORGANISM: Artificial Sequence
<220> FEATURE:
<223> OTHER INFORMATION: 6C4 light chain variable region
<220> FEATURE:
<221> NAME/KEY: misc_feature
<222> LOCATION: (50)..(50)
<223> OTHER INFORMATION: Xaa can be any naturally occurring amino acid

<400> SEQUENCE: 82

Leu Ser Gly Val Glu Gly Asp Ile Val Met Thr Gln Ser His Lys Phe
1               5                   10                  15

Met Ser Thr Ser Val Gly Asp Arg Val Ser Ile Ile Cys Lys Ala Arg
            20                  25                  30

Gln Asp Val Gly Thr Ala Val Ala Trp Tyr Gln Gln Lys Pro Gly Gln
        35                  40                  45

Ser Xaa Lys Leu Leu Ile Tyr Trp Ala Ser Thr Arg His Thr Gly Val
50                  55                  60

Pro Asp Arg Phe Thr Gly Ser Gly Ser Gly Thr Asp Phe Thr Leu Thr
65                  70                  75                  80
```

-continued

```
Ile Ser Asn Val Gln Ser Glu Asp Leu Ala Asp Tyr Phe Cys Gln Gln
                85                  90                  95

Tyr Ser Arg Tyr Ala Leu Thr Phe Gly
            100                 105
```

COMPOSITIONS COMPRISING CelTOS IMMUNOGENS AND ANTIBODIES AND METHOD OF USE THEREOF

CROSS REFERENCE TO RELATED APPLICATIONS

This application claims the benefit of and is related to International Patent Application number PCT/US2017/059589, filed Nov. 1, 2017, which claims the benefit of U.S. Provisional Application No. 62/415,894 filed on Nov. 1, 2016, the disclosures of which are hereby incorporated by reference in their entirety.

GOVERNMENTAL RIGHTS

This invention was made with government support under AI080792, AI064478 and HHSN272201400018C awarded by the National Institutes of Health. The government has certain rights in the invention.

FIELD OF THE INVENTION

The present disclosure provides immunogenic compositions and methods for use thereof comprising novel CelTOS epitopes. In particular, the vaccine compositions of the invention comprise Plasmodium, Babesia, Theileria or Cytauxzoon CelTOS immunogens.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Malaria continues to impose a global health and socioeconomic burden on the majority of the world's population. The lack of an effective and commercially available vaccine impedes the prevention and control of this disease which afflicts 200 million people causing half a million deaths annually (3, 8). A new approach to malaria vaccine development is needed to complement ongoing efforts which have produced promising, but less effective or short-lived protection against malaria (8, 9). Structural vaccinology is a new approach to vaccine development and is beginning to be applied towards the development of a malaria vaccine (10-13). This approach relies on identifying epitopes in antigens that are specifically targeted by neutralizing antibodies, uncovering the structural basis of epitope recognition, and applying this information to design immunogens that elicit a protective antibody response (10-14). In addition to applying structural vaccinology to current malaria parasite antigens (11, 13), it is also necessary to identify and pursue new antigens for a malaria vaccine.

Thus, there remains a need in the art for the development and use of novel immunogens in the development of a malaria vaccine.

SUMMARY OF THE INVENTION

The present disclosure relates to novel CelTOS immunogens and antibodies, in particular the CelTOS immunogens and antibodies are suitable as human and/or animal vaccines against a parasite of the phylum Apicomplexa.

In one aspect, embodiments of the disclosure provide immunogenic compositions comprising Plasmodium, Babesia, Theileria or Cytauxzoon CelTOS immunogen and a suitable adjuvant.

In another aspect, embodiments of the invention provide compositions comprising an antibody that specifically binds an epitope within CelTOS.

In another aspect, embodiments of the invention provide methods of administering the above CelTOS immunogenic compositions and/or antibodies to a subject in need thereof.

In yet another aspect, the invention provides methods of detecting an infection caused by a Plasmodium, Babesia, Theileria or Cytauxzoon pathogen.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The application file contains at least one drawing executed in color. Copies of this patent application publication with color drawing(s) will be provided by the Office upon request and payment of the necessary fee.

FIG. 2A shows the backbone piggyBac plasmid pL-BACII-bEDMH. FIG. 2B shows the Luciferase-expressing piggyBac vector pL-bEDMH-Luc driven by P. berghei EF1-α promoter with hDHFR drug selection marker. FIG. 2C shows the transposes-expressing helper plasmid pDCTH with 5'-P. chabaudi DHFR-TS and 5'-P. falciparum calmodulin (PfCAM) dual promoters.

FIG. 3 A shows a column bar graph of gametocytemia percentage in seven pL-BACII-bEDMH-Luc genome-integrated parasite clones when compared to the wild type PfKF7 parasite. The error bars represent standard deviation from the mean of 8 measurements. FIG. 3B shows a scatter plot chart showed clone PfKF7G4 had highest luciferase expression in oocyst developing in mosquito stage. RLU (Relative Luminescence Units) of mosquitoes (n=5) luciferase activity on day 8 post infection by gametocytes cultured in vitro from eight independent experiments each with 18 replicate samples. Statistical differences were determined by Kruskal-Wallis and Dunn's multiple comparison tests. The graph is shown as mean±SD.

FIG. 4A graphically depicts the same where the error bars represent standard deviation from the mean of 8 measurements of human RBC percentages in mouse peripheral blood by anti-human CD235a-APC flow cytometry analysis. FIG. 4 B shows a representative FC scatter plots of huRBC proportion in mouse peripheral blood.

FIG. 9A depicts the experimental procedure. Flowcharts of steps involved in humanized mice preparation, mice infection by mouse-adapted parasite PfKF7G4 and gametocyte culture in vivo, antibody inhibition administration, mosquitoes feeding and mosquito-stage luciferase detection. FIG. 9B shows the luciferase-based antibody-mediated *P. falciparum* oocyst inhibition in vivo. Evaluation of CelTOS antibody transmission blocking activity by mosquito luciferase assay on day 8 post blood feeding with gametocyte cultured in vivo. huRBC-NSG mice with huRBC level >32% were infected with mouse-adapted *P. falciparum* parasite clone PfKF7G4, mature infective stage V gametocytemia were range from 0.07% to 0.18%. Mice were randomly divided into 4 groups, each mouse in the antibody treatment groups received 16 mg/kg antibody in 200 ul RPMI by intravenously injection, the blank control group received of equal volume RPMI in the same way, one hour later, directly feed 100 mosquitoes for each mouse. Compared with control groups by using luciferase assay on day 8 after feeding. The graph represents the results of four separate experiments. Values are means±SD. CelTOS mAb groups demonstrated significantly inhibitory activity for oocyst developing in mosquito.

FIG. 11A shows Pf4H12 inhibits PfCelTOS-mediated liposome disruption. Using the non-parametric Kruskal-Wallis test followed by the Dunn's test, the relative percentage of liposomes disrupted five minutes after treatment with PfCelTOS alone was significantly different from treatments with PfCelTOS:Pf4H12 at molar ratios of 1:0.5 (p value=0.0363), 1:1 (p value=0.0248), and 1:2 (p value=0.0363). FIG. 11B shows Pv7G7 inhibits PvCelTOS-mediated liposome disruption. Using the non-parametric Kruskal-Wallis test followed by the Dunn's test, the relative percentage of liposomes disrupted five minutes after treatment with PvCelTOS alone was significantly different from treatments with PvCelTOS:Pv7G7 at molar ratios of 1:1 (p value=0.0217) and 1:2 (p value=0.0002) but not at 1:0.5 (p value=0.6844).

FIG. 12A shows the structure of PfCelTOS/Pf4H12 Fab complex. Left panel: The heavy chain is in dark slate, the light chain is in light cyan, PfCelTOS is in green with the epitope colored in red. Middle panel: Mapping of the Pf4H12 epitope, with residues contacted by the Fab shown in stick form. Right panel: Alignment of PfCelTOS (green and red), in the PfCelTOS/Pf4H12 Fab complex, to PvCelTOS (PDB accession code 5TSZ, shown in grey) using PyMOL had RMS=2.35. FIG. 12B shows the structure of PvCelTOS/Pv7G7 Fab complex. Left panel: The heavy chain is in gold, the light chain is in wheat, PvCelTOS is in dark green with the epitope colored in red. Middle panel: Mapping of the Pv7G7 epitope, with residues contacted by the Fab shown in stick form. Right panel: Alignment of PvCelTOS (dark green and red), in the PvCelTOS/Pv7G7 Fab complex, to PvCelTOS (PDB accession code 5TSZ, shown in grey) using PyMOL had RMS=6.186. FIG. 12C shows the structure of PvCelTOS/Pv6C4 Fab complex. Left panel: The heavy chain is in olive, light chain is in orange, PvCelTOS is in light green with the epitope colored in red. Middle panel: Mapping of the Pv6C4 epitope, with residues contacted by the Fab shown in stick form. Right panel: Alignment of PvCelTOS (light green and red), in the PvCelTOS/Pv6C4 Fab complex, to PvCelTOS (PDB accession code 5TSZ, shown in grey) using PyMOL had RMS=0.591.

FIG. 13A shows the kinetics of Hydrogen-deuterium exchange for regions of PfCelTOS in the presence of Pf4H12 (shown in red), Pf4D1 (shown in green) and in the absence of antibodies (apo state shown in blue). A region of PfCelTOS showing reduced rates of exchange in the presence of antibodies is the epitope targeted by that antibody. FIG. 13B Top panel: Homology model of PfCelTOS (shown in grey) depicting the epitope targeted by Pf4H12 that was identified by HDX-MS (red), from the crystal structure of the PfCelTOS/Pf4H12 complex (blue), or by both methods (purple). FIG. 13C Bottom panel: Homology model of PfCelTOS (shown in grey) depicting the epitope targeted by Pf4D1 that was identified by HDX-MS (salmon).

FIG. 16A shows exposure of both P. falciparum and P. vivax to anti-CelTOS 4D1 monoclonal results in an increased invasion rate from 90 to 250 pg/mL FIG. 16B depicts staining P. vivax infected wells with pre-exposure to 250 pg/mL reveals a multi-invaded PHH with developing LS schizonts. Green is anti-GAPDH. FIG. 16C and FIG. 16D show P. vivax sporozoites exposed to anti-celTOS 4D1 experience a growth defect with a reduction in size (2 μm) in comparison to non-exposure sporozoite control.

DETAILED DESCRIPTION OF THE INVENTION

Figure 1:
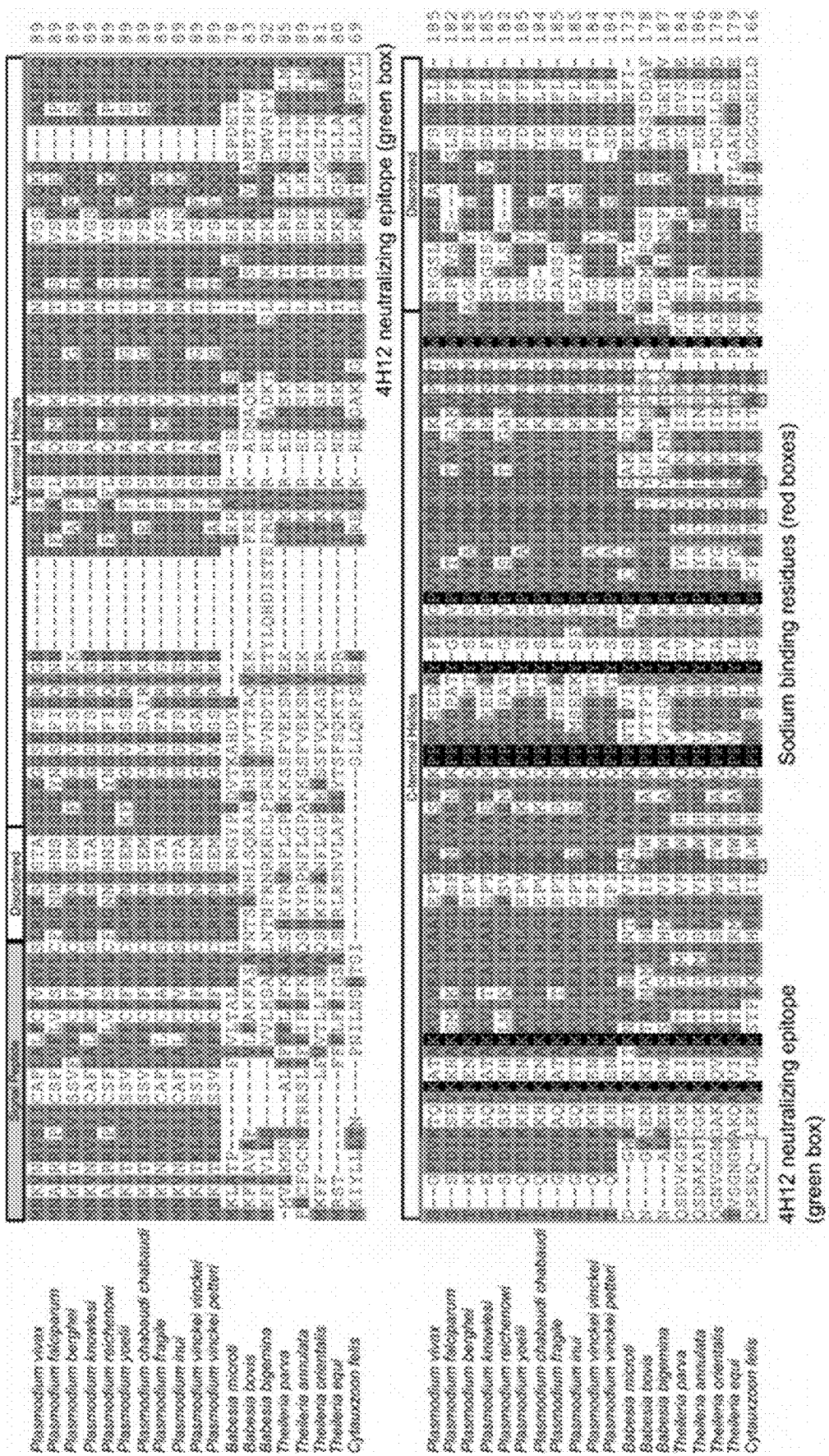
FIG. 1 depicts the sequence alignment of Apicomplexan CelTOS C-terminal helices residues showing the sodium binding residues (red boxes) within the C-terminal helices and the 4H12 neutralizing epitopes (green box) Plasmodium vivax SEQ ID NO:2; Plasmodium vivax SEQ ID NO:1; Plasmodium berghei SEQ ID NO:7; Plasmodium knowlesi SEQ ID NO:3; Plasmodium reichenowi SEQ ID NO:8; Plasmodium yoelii SEQ ID NO:10; Plasmodium chabaudi SEQ ID NO:9; Plasmodium fragile SEQ ID NO:11; Plasmodium inui SEQ ID NO: 12; Plasmodium vinckei SEQ ID NO: 13; Plasmodium petteri SEQ ID NO:14; Babesia microti SEQ ID NO:4; Babesia bovis SEQ ID NO: 15; Babesia bigemina SEQ ID NO: 16; Theileria parva SEQ ID NO:5; Theileria annulata SEQ ID NO: 17; Theileria orientalis SEQ ID NO:18; Theileria equi SEQ ID NO: 19; and Cytauxzoon felis SEQ ID NO:6.

Immunization with a CelTOS vaccine could mimic the development of immunity from natural malaria exposures. The development of an efficacious pre-erythrocytic stage malaria vaccine from CelTOS (cell traversal protein for ookinetes and sporozoites) has the potential to protect subjects susceptible to parasitic infection. Vaccination with a pre-erythrocytic stage vaccine reduces or eliminates the traversal of infective sporozoites through cells required for infection of liver cells and thus protect against infection and/or reduce the severity of the disease. Vaccination with a transmission blocking vaccine reduces or eliminates the transmission of infective parasites by the arthropod vector and thus protect against transmission and/or reduce the incidence of the disease.

The mechanism of protection induced by an infection blocking vaccine (including but not limited to pre-erythrocytic stage malaria vaccines) would be mediated by the development of specific protective antibodies to proteins on the parasite surface and block the traversal of the parasite through cells leading to productive infection. The putative mode of action of these antibodies is to bind the surface of the parasite and block their ability to associate with and invade cells necessary for infection. The effect of blocking this process would be to reduce the potential amplification of parasites in the host and thus reduce parasitic load.

The mechanism of protection induced by a transmission blocking vaccine would be mediated by the development of specific protective antibodies to proteins on the parasite surface and block the transmission of infectious parasites by the arthropod vector to prevent further infection and incidence of disease. The putative mode of action of these antibodies is to bind the surface of the parasite and block their ability to associate with and traverse cells in the arthropod vector necessary for the formation of infectious parasites. The effect of blocking this process would be to reduce the potential amplification of parasites in the arthropod vector and thus reduce transmission.

The present invention provides compositions and methods for vaccination with a CelTOS vaccine. The technology provided herein generally relates to novel CelTOS specific epitopes suitable as human and/or animal vaccines against parasites or pathogens of the phylum Apicomplexa. In particular, the present disclosure relates to novel CelTOS immunogenic compositions as a basis for vaccines against *Plasmodium* parasites, including *P. falciparum*, *P. vivax*, *P. malariae*, *P. ovale* and *P. knowlesi*. Nucleic acid molecules encoding said immunogens, vectors, host cells containing the nucleic acids and methods for preparation and producing such immunogens; antibodies induced or generated by the use of said immunogens or said nucleic acid molecules encoding said immunogens and the use of such antibodies or recombinant derivatives for passive immunotherapy; compositions and methods for using such immunogenic compositions for the prevention and treatment of malaria are also encompassed by the present disclosure.

I. Compositions

Compositions of the disclosure are directed to immunogenic compositions comprising *Plasmodium, Babesia, Theileria* or *Cytauxzoon* CelTOS immunogen. Compositions of the disclosure are also directed to anti-CelTOS antibodies and compositions comprising said antibodies. Various aspects of the disclosure will be described in further detail below.

(a) CelTOS

In an aspect, the present disclosure provides an immunogenic composition, wherein the immunogenic composition comprises Apicomplexan CelTOS immunogen. In another aspect, the present disclosure provides an immunogenic composition, wherein the immunogenic composition comprises a *Plasmodium, Babesia, Theileria* or *Cytauxzoon* CelTOS immunogen. In still another aspect, the present disclosure provides an immunogenic composition, wherein the immunogenic composition comprises a *Plasmodium, Babesia, Theileria* or *Cytauxzoon* CelTOS immunogen and suitable excipient. The term "immunogenic composition" as used herein means a composition comprising an immunogen comprising a CelTOS epitope as described herein that when administered to a subject, typically elicits a protective immune response. An immune response may include induction of antibodies and/or induction of a T-cell response. The immunogenic compositions described herein provide a protective immune response that ameliorates one or more symptoms of the target disorder.

"Immunogen", as used herein, refers to a molecule that contains one or more epitopes (linear, conformational or both) that upon exposure to a subject will induce an immune response that is specific for that antigen (e.g. CelTOS). An epitope is the specific site of the antigen which binds to a T-cell receptor or specific antibody, and typically comprises about 3 amino acid residues to about 20 amino acid residues. As used herein, "CelTOS" refers to cell-traversal protein for ookinetes and sporozoites (CelTOS, PFL0800c). CelTOS is required for parasite traversal of cells within both vector and the host. The inventors have discovered that CelTOS is conserved across various diverse branches of Apicomplexan parasites.

The Apicomplexa (also referred to as Apicomplexia) are a large group of protists, most of which possess a unique organelle called apicoplast and an apical complex structure involved in penetrating a host's cell. They are a diverse group including organisms such as coccidia, gregarines, piroplasms (e.g. *Theileria, Babesia, Cytauxzoon* spp.), haemogregarines, and plasmodia/hemosporidia (e.g. *Plasmodium falciparum, Plasmodium vivax, Plasmodium ovale, Plasmodium malariae, Plasmodium knowlesi*). Specifically, the CelTOS is conserved amongst the hemosporidia (e.g. *Plasmodium* spp.) and piroplasms (e.g. *Theileria, Babesia, Cytauxzoon* spp.).

The *Plasmodium* CelTOS may comprise the sequence of *Plasmodium falciparum* as set forth in SEQ ID NO:1 (MNALRRLPVICSFLVF-FLVFSNVLCFRGNNGHHNSSSS-LYNGSQFIEQLNNSFTSAFL ESQSMNKIGDDLAETIS-NELVSVLQKNSPTFLESSFDIKSEVKKHAKSMLKELI-KVGLPS FENLVAENVKPPKVDPATYGIIVPVLT-SLFNKVETAVGAKVSDEIWNYNSPDVSESEES LSDDFFD). In one aspect, the *Plasmodium* CelTOS may comprise the sequence of *Plasmodium vivax* as set forth in SEQ ID NO:2 (MNKVNRSIICAFLA-LFCFVNVLSLRGKSGSTASSSLEGGSEFSERI-GNSLSSFLSESAS LEVIGNELADNIANEIVSSLQKD-SASFLQSGFDVKTQLKATAKKVLVEALKAALEPTEK-IV ASTIKPPRVSEDAYFLLGPWKTLFNKVEDVLHK-PIPDTIWEYESKGSLEEEEAEDEFSD ELLD). In another aspect, the *Plasmodium* CelTOS may comprise the sequence of *Plasmodium knowlesi* as set forth in SEQ ID NO:3 (MNKVNRSIICAFLALFCFVNVLSLRGKSGSTASSS-LEGGSEFSERIGNSLSSFLSESAS LEVIGNELADNIA-NEIVSSLQKDSASFLQSGFDVKTQLKAT-AKKVLVEALKAALEPTEKIV ASTIKPPRVSEDAYFLLGPWKTLFNKVEDVLHK-PIPDTIWEYESKGSLEEEEAEDEFSD ELLD). The *Bebesia* CelTOS sequence may comprise the sequence of *Bebesia microti* (I7J9D8) set forth in SEQ ID NO:4 (MKLATP-FLVLTALNIVILHARRVERGYPSDVTKAHDYNLKRAI-RSELETASDQIVEIIAQH VEKILQEQSPDETS-FIQDGWKSTAKKITKNAVVHIAKNTIPVIAAIVADSV-KPPNTDVIVY NSLFKPVCKDIFDHVSAKLDIKPDDSI-WEYSGDDGYEDEDENENEEDDEFI). The *Theileria* CelTOS sequence may comprise the sequence of *Theileria parva* (982Q4N) set forth in SEQ ID NO:5 (MVLKMNSA-LIFFFLFFKAAESHKYRVNFLGPSKKSSFVEKSN-VEKLTKVLREDLNSKV DEVVDLI-ATDLERELLKNGLTNLSLMQQSDVKGFGSKAKEIIK-KTLVGVMRSLLPVFER WIHDSVQPPWDKHVYGV-LIHPIGYRICEQIHEKLKISEPNPWKDDEIEEEEPEE-EQDE GDSVSDEAIDQLLTM). The *Cytauxzoon* CelTOS sequence may comprise the sequence of *Cytauxzoon felis* (CF003135) set forth in SEQ ID NO:6 (MKIYLLLTNP-NILNSNTSISLLQKPSVEELREVIKRDLGAKV-GEVVELLATDLEKALTDN NLLAAPSYLQRSE-QLEKVKVLVKSTFIKVLRHVLPILELVVVHESLLPPK-VSKLIYNSIVQPI CFSITEELNNKLKITAGNPWKKD-VEEEDDGLGDLDLGGGGEDLDVFDIDICSYCDISIM MCGVQTRPACVFEDRFLVRSIDNSKFERVSRINAK-STGFDAELLLDVNSDILPVNNKSM LHILIT-NSLLPSGTDINLCEYNDIPSLLGDYEYAMYGKIFK-FEEVSSENRTIYASFGGLLM SLTADKQVVADLELGELIYFALYF). In some embodiments, an immunogenic composition or vaccine composition comprises a *Plasmodium, Babesia, Theileria* or *Cytauxzoon* CelTOS that has at least 80%, at least 81%, at least 82%, at least 83%, at least 84%, at least 85%, at least 86%, at least 87%, at least 88%, or 89% identity to SEQ ID NO:1, SEQ ID NO:2 or SEQ ID NO:3, respectively. In another embodiment, a vaccine composition comprises a *Babesia, Theileria* or *Cytauxzoon* CelTOS that has at least 90%, at least 91%, at least 92%, at least 93%, at least 94%, at least 95%, at least 96%, at least 97%, at least 98%, at least 99%, or at least 100% identity to SEQ ID NO:1, SEQ ID NO:2, SEQ ID NO:3, SEQ ID NO:4, SEQ ID NO:5, or SEQ ID NO:6, respectively.

In yet another embodiment, a immunogenic or vaccine composition comprises a *Babesia, Theileria* or *Cytauxzoon* CelTOS that may be a fragment, truncation or variant of SEQ ID NO:1, SEQ ID NO:2, SEQ ID NO:3, SEQ ID NO:4, SEQ ID NO:5, or SEQ ID NO:6 that has the same activity as the full length CelTOS. In some aspects the CelTOS fragment comprises one or more of the regions between amino acids 51-76, 76-137, 137-169, 36-51, 169-177, 51-177, 136-177, 169-177, or 137-177. In some embodiments, an immunogenic or vaccine composition comprises an immunogen with a CelTOS epitope as described above. In one aspect, the immunogenic or vaccine composition comprises an immunogen with a CelTOS epitope comprising one or more of SEQ ID NO:20 (QKNSPTFLES), SEQ ID NO:21 (QKDSASFLQS), SEQ ID NO:22 (QND-SASFLQS), SEQ ID NO:23 (QQDSSSFLQT), SEQ ID NO:24 (QQDSSSFLQT), SEQ ID NO:25 (QEQSPDETS-FIQD), SEQ ID NO:26 (VEANETHPVFLQN), SEQ ID NO:27 (EQNDMVRPVFLEN), SEQ ID NO:28 (LKNGLTNLSLMQQ), SEQ ID NO:29 (LKNGLTNLSLMQQ), SEQ ID NO:30 (LKG-GLTNLSLLQQ), SEQ ID NO:31 (GKNGLLAASYLET), SEQ ID NO:32 (TDNNLLAAPSYLQ), SEQ ID NO:33 (QKNSPTFLES), SEQ ID NO:34 (QQDSSSFLQT), SEQ ID NO:35 (QKDSASFLQS), SEQ ID NO:36 (QKD-SASFLQS), SEQ ID NO:37 (QQDSASFLQT), SEQ ID NO:38 (QQDSASFVQT), SEQ ID NO:39 (AFLESQSMNKI), SEQ ID NO:40 (FLSESASLEVI), SEQ ID NO:41 (FLSESASLEVI), SEQ ID NO:42 (FISESSSLDDI), SEQ ID NO:43 (FISESASLDDI), SEQ ID NO:44 (AIRSELETA), SEQ ID NO:45 (LIKADMAQK), SEQ ID NO:46 (IVRRDIADK), SEQ ID NO:47 (VL-REDLNSK), SEQ ID NO:48 (VLREDLNSK), SEQ ID NO:49 (VIRDDLNSK), SEQ ID NO:50 (IIRNDLDSK), SEQ ID NO:51 (VIKRDLGAK), SEQ ID NO:52 (AFLESQSMNKI), SEQ ID NO:53 (FISESASLDDI), SEQ ID NO:54 (FLSESASMEVI), SEQ ID NO:55 (FLS-ESTSLEVI), SEQ ID NO:56 (FISESASVDDI), SEQ ID NO:57 (FISESASVDDI), SEQ ID NO:58

(TSLFNKVETAVGAKVSDEI), SEQ ID NO:59 (KTLFNKVEDVLHKPIPDTI), SEQ ID NO:60 (RSLFNKVEDVLHKPVSDDI), SEQ ID NO:61 (KALFNKIEEAVHKPVSDNI), SEQ ID NO:62 (KALFNKIEDAVHKPVNDNI), SEQ ID NO:63 (KDIFDHVSAKLDIKPDDSI), SEQ ID NO:64 (KSIFDNIYGKLKMEPSKQ), SEQ ID NO:65 (KSIFDQLYHKFNLPTSKI), SEQ ID NO:66 (YRICEQIHEKLKISEPNP), SEQ ID NO:67 (YRICEQIHEKLKINEPNP), SEQ ID NO:68 (FGISEQLHEKLHIDKPNP), SEQ ID NO:69 (FGISEELRNKLHITTENP), SEQ ID NO:70 (SSLFNKVETAVGANVPDDI), SEQ ID NO:71 (KSLFNKIEEAVHKPVSDSI), SEQ ID NO:72 (KSLFNKIEEAVHKPVSDSI), SEQ ID NO:73 (KTLFNKVEDVLHKPIPDNI), SEQ ID NO:74 (KSLFNKIEDALHKPVPDDI), SEQ ID NO:75 (KALFNKIEEAVHKPVSDNI), or SEQ ID NO: 76 (KALFNKIEEAVHKPVSDGI). In another embodiment, immunogenic or vaccine composition comprises an immunogen with a CelTOS epitope that has at least 90%, at least 91%, at least 92%, at least 93%, at least 94%, at least 95%, at least 96%, at least 97%, at least 98%, at least 99%, or at least 100% identity to SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75 or SEQ ID NO:76, respectively.

In an aspect, the present disclosure provides an immunogenic composition, wherein the immunogenic composition comprises a homolog of Apicomplexan CelTOS. In another aspect, the present disclosure provides an immunogenic composition, wherein the immunogenic composition comprises a homolog of *Plasmodium, Babesia, Theileria* or *Cytauxzoon* CelTOS. In still another aspect, the present disclosure provides an immunogenic composition, wherein the vaccine composition comprises a homolog of *Babesia, Theileria* or *Cytauxzoon* CelTOS. Homologs can be found in other parasites and/or species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the disclosure. Equally, BLAST protein searches may be performed with the BLASTX program to obtain amino acid sequences that are homologous to a polypeptide of the disclosure. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. In some embodiments, a homolog has at least 80%, at least 81%, at least 82%, at least 83%, at least 84%, at least 85%, at least 86%, at least 87%, at least 88%, or 89% identity to SEQ ID NO:1, SEQ ID NO:2 or SEQ ID NO:3. In another embodiment, a homolog has at least 90%, at least 91%, at least 92%, at least 93%, at least 94%, at least 95%, at least 96%, at least 97%, at least 98%, at least 99%, or at least 100% identity to SEQ ID NO:1, SEQ ID NO:2, SEQ ID NO:3, SEQ ID NO:4, SEQ ID NO:5, or SEQ ID NO:6. In yet another embodiment, CelTOS may be a fragment, truncation or variant of SEQ ID NO:1, SEQ ID NO:2, SEQ ID NO:3, SEQ ID NO:4, SEQ ID NO:5, or SEQ ID NO:6 that has the same activity as the full length CelTOS.

In an aspect, the present disclosure provides an immunogenic composition, wherein the immunogenic composition comprises Apicomplexan CelTOS, and wherein the CelTOS comprises structural changes that affect immune recognition. In another aspect, the present disclosure provides an immunogenic composition, wherein the immunogenic composition comprises *Plasmodium, Babesia, Theileria* or *Cytauxzoon* CelTOS, and wherein the CelTOS comprises structural changes that affect immune recognition. In still another aspect, the present disclosure provides an immunogenic composition, wherein the immunogenic composition comprises *Plasmodium, Babesia, Theileria* or *Cytauxzoon* CelTOS, and wherein the CelTOS comprises structural changes that affect immune recognition. The inventors have discovered that a sodium ion stabilizes CelTOS in a closed conformation and membrane embedded and cytosolic environments affect CelTOS conformation. The inventors also found that CelTOS undergoes large conformational changes resulting in compact and elongated structures. Specifically, wild-type CelTOS that is competent for sodium binding results in a compact structure, while mutating the sodium binding residues results in an elongated structure. These changes exposed regions of CelTOS that facilitate membrane disruption and alter available epitopes. Accordingly, the CelTOS may comprise structural changes in the C-terminal helices that affect sodium binding thereby affecting immune recognition. The structural changes may be induced via mutation of the C-terminal helices of CelTOS. Accordingly, in an aspect, the present disclosure also provides a vaccine composition, wherein the vaccine composition comprises Apicomplexan CelTOS, and wherein the CelTOS comprises one or mutations in the C-terminal helices that affect sodium binding thereby affecting immune recognition. In another aspect, the present disclosure also provides a vaccine composition, wherein the vaccine composition comprises *Plasmodium, Babesia, Theileria* or *Cytauxzoon* CelTOS, and wherein the CelTOS comprises one or mutations in the C-terminal helices that affect sodium binding thereby affecting immune recognition. In still another, the present disclosure also provides a vaccine composition, wherein the vaccine composition comprises *Plasmodium, Babesia, Theileria* or *Cytauxzoon* CelTOS, and wherein the CelTOS comprises one or mutations in the C-terminal helices that affect sodium binding thereby affecting immune recognition. Specifically, the vaccine composition may comprise an Apicomplexan CelTOS with one or more mutations in the C-terminal helices residues depicted in FIG. 1. More specifically, the vaccine composition may comprise an Apicomplexan CelTOS with one or more mutations in the sodium binding residues (red boxes) within the C-terminal helices depicted in the FIG. 1.

In an aspect, an immunogenic composition of the disclosure may comprise more than one CelTOS eptiopes. For example, the composition may comprise 2, 3, 4, 5, 6, 7, 8, 9 or 10 CelTOS epitopes. Additionally, the composition may comprise more than 10 CelTOS epitopes. The CelTOS may be the same or different. The CelTOS epitopes may be linked together by various methods known in the art. Suitable linkers include amino acid chains and alkyl chains functionalized with reactive groups for coupling to 2 or more CelTOS epitopes. In an embodiment, the linker may include amino acid side chains, referred to as a peptide linker. Accordingly, additional amino acid residues may be added at the amino terminus of a CelTOS of the disclosure for the purpose of providing a linker by which the CelTOS of the present disclosure can be conveniently affixed to a label or solid matrix, or carrier. Amino acid residue linkers are usually at least one residue and can be 40 or more residues, more often 1 to 10 residues, but do not comprise the CelTOS. Typical amino acid residues used for linking are tyrosine, cysteine, lysine, glutamic and aspartic acid, or the like.

In another embodiment, an alkyl chain linking group may be coupled to the CelTOS by reacting the amino group of the N-terminal residue of the CelTOS of the disclosure with a first functional group on the alkyl chain, such as a carboxyl group or an activated ester. Subsequently the second CelTOS is attached to the alkyl chain to complete the formation of the complex by reacting a second functional group on the alkyl chain with an appropriate group on the second CelTOS. The second functional group on the alkyl chain is selected from substituents that are reactive with a functional group on the CelTOS while not being reactive with the N-terminal residue of the first CelTOS. The process may be repeated for the addition of subsequent CelTOS proteins.

An alternative chemical linking group to an alkyl chain is polyethylene glycol (PEG), which is functionalized in the same manner as the alkyl chain described above. The CelTOS of the disclosure may be PEGylated for improved systemic half-life and reduced dosage frequency. In an embodiment, PEG may be added to a linker. As such, a CelTOS of the disclosure may comprise a linker and PEG.

In another aspect, the present disclosure pertains to isolated nucleic acid molecules, selected from the group consisting of a) nucleic acid molecules encoding a CelTOS comprising immunogen according to the present disclosure; b) nucleic acid molecules encoding for a modified form of a CelTOS comprising immunogen according to the present disclosure, preferably in which one or more amino acid residues are conservatively substituted; c) nucleic acid molecules that are capable of hybridizing to any of the nucleic acid molecules of a)-b) under stringent conditions; d) nucleic acid molecules that are capable of hybridizing to the complement of any of the nucleic acid molecules of a)-c) under stringent conditions; e) a nucleic acid molecule having a sequence identity of at least 85% with any of the nucleic acid molecules of a)-d) and encoding a CelTOS comprising immunogen as described above and suitable as a human and/or animal vaccine against one or more parasites of the phylum Apicomplexa; f) or complements of any of the nucleic acid molecules of a)-e).

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin. The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram. Conservative substitutions may be made, for example, according to Table 4 below which describes a generally accepted Venn diagram grouping of amino acids.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes.

The present disclosure is also directed to vectors comprising a nucleotide molecule of the present disclosure. As used herein, plasmid or viral vectors are agents that transport the disclosed nucleic acids, such as a nucleic acid sequence capable of encoding one or more of the disclosed peptides or recombinant antibodies into the cell without degradation and include a promoter yielding expression of the gene in the cells into which it is delivered. In some embodiments the nucleic acid sequences disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. The viral vectors may be formulated in pharmaceutical compositions as those described above. The viral vector may be in the form of an isolated viral particle.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

In some embodiments, the viral vector that can be used to introduce the polynucleotides of the invention into a cell is based on an adeno-associated virus (AAV) serotypes. This defective parvovirus is a preferred vector of the invention because it can infect many cell types and is nonpathogenic to humans. Gene transfer using adeno-associated virus (AAV) is well known for its safety and ability to express exogenous genes for prolonged periods. AAV type vectors can transport about 4 to 5 kb and wild type AAV is known to stably insert into chromosome 19. In a particular embodiment, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

As used herein, the term "AAV vector" means a vector derived from an adeno-associated virus serotype. In non-limitation examples AAV vectors include, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Despite the high degree of homology, the different serotypes have tropisms for different tissues.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the invention, may also be referred to as a "recombinant host cell".

The term "host cell(s)" refers to cell(s), which may be used in a process for purifying an immunogenic protein or recombinant antibody in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archeobacteria, bacterial cells, insect cells, yeast, mammal cells, and/or plant cells. Bacteria envisioned as host cells can be either gram-negative or gram-positive, e.g. *Escherichia coli*, *Erwinia* sp., *Klebsellia* sp., *Lactobacillus* sp. or *Bacillus subtilis*. Typical yeast host cells are selected from the group consisting of *Saccharomyces cerevisiae, Hansenula polymorpha* and *Pichia pastoris*.

To express an immunogenic protein or recombinant antibody according to the present disclosure, a DNA encoding an immunogenic protein or recombinant antibody or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

The immunogenic compositions of the disclosure may include a pharmaceutically acceptable excipient such as a suitable adjuvant. Suitable adjuvants include an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quit A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants. In an exemplary embodiment, the adjuvant is selected from the group consisting of Freund's complete adjuvant and Freund's incomplete adjuvant.

Immunogenic compositions and vaccines of the disclosure will typically, in addition to the antigenic and adjuvant components mentioned above, comprise one or more "pharmaceutically acceptable carriers or excipients", which include any excipient that does not itself induce the production of antibodies harmful to the individual receiving the composition. Suitable excipients are typically large, slowly metabolised macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, $20^{th}$ edition, ISBN: 0683306472.

Compositions of the disclosure may be lyophilised or in aqueous form, i.e. solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses).

Liquid compositions of the disclosure are also suitable for reconstituting other compositions of the disclosure from a lyophilized form. Where a vaccine is to be used for such extemporaneous reconstitution, the disclosure provides a kit, which may comprise two vials, or may comprise one ready-filled syringe and one vial, with the contents of the syringe being used to reconstitute the contents of the vial prior to injection.

Immunogenic compositions and vaccines of the disclosure may be packaged in unit dose form or in multiple dose form (e.g. 2 doses). For multiple dose forms, vials are preferred to pre-filled syringes. Effective dosage volumes can be routinely established, but a typical human dose of the composition for injection has a volume of 0.5 mL.

In one embodiment, the compositions of the disclosure have a pH of between 6.0 and 8.0, in another embodiment, the compositions of the disclosure have a pH of between 6.3 and 6.9, e.g. 6.6±0.2. The compositions may be buffered at this pH. Stable pH may be maintained by the use of a buffer. If a composition comprises an aluminium hydroxide salt, a histidine buffer may be used (WO03/009869). The composition should be sterile and/or pyrogen free.

Compositions of the disclosure may be isotonic with respect to humans.

Compositions of the disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

Compositions of the disclosure may comprise a detergent e.g. a Tween (polysorbate), such as Tween 80. Detergents are generally present at low levels e.g. <0.01%.

Compositions of the disclosure may include sodium salts (e.g. sodium chloride) to give tonicity. The composition may comprise sodium chloride. In one embodiment, the concentration of sodium chloride in the composition of the disclosure is in the range of 0.1 to 100 mg/mL (e.g. 1-50 mg/mL, 2-20 mg/mL, 5-15 mg/mL) and in a further embodiment the concentration of sodium chloride is 10±2 mg/mL NaCl e.g. about 9 mg/m L.

Compositions of the disclosure will generally include a buffer. A phosphate or histidine buffer is typical.

Compositions of the disclosure may include free phosphate ions in solution (e.g. by the use of a phosphate buffer) in order to favor non-adsorption of antigens. The concentration of free phosphate ions in the composition of the disclosure is in one embodiment between 0.1 and 10.0 mM, or in another embodiment between 1 and 5 mM, or in a further embodiment about 2.5 mM.

(b) Antibodies

In another aspect, the present disclosure provides an antibody, wherein the antibody is generated from a CelTOS of the disclosure. Methods of generating an antibody to a protein are well known in the art. For example, monoclonal antibodies may be generated using a suitable hybridoma as would be readily understood by those of ordinary skill in the art. In the preferred process, a protein in accordance with the disclosure is first identified and isolated. Next, the protein is isolated and/or purified in any of a number of suitable ways commonly known in the art, or after the protein is sequenced, the protein used in the monoclonal process may be produced by recombinant means as would be commonly used in the art and then purified for use. In one suitable process, monoclonal antibodies may be generated from proteins isolated and purified as described above by mixing the protein with an adjuvant, and injecting the mixture into a laboratory animal. Immunization protocols may consist of a first injection (using complete Freund's adjuvant), two subsequent booster injections (with incomplete Freund's adjuvant) at three-week intervals, and one final booster injection without adjuvant three days prior to fusion. For hybridoma production, the laboratory animal may be sacrificed and their spleen removed aseptically. Antibody secreting cells may be isolated and mixed with myeloma cells (NS1) using drop-wise addition of polyethylene glycol. After the fusion, cells may be diluted in selective medium (vitamin-supplemented DMEM/HAT) and plated at low densities in multiwell tissue culture dishes. Tissue supernatants from the resulting fusion may be screened by both ELISA and immunoblot techniques. Cells from these positive wells may be grown and single cell cloned by limiting dilution, and supernatants subjected to one more round of screening by both ELISA and immunoblot. Positive clones may be identified, and monoclonal antibodies collected as hybridoma supernatants.

Anti-CelTOS antibodies useful herein include all antibodies that specifically bind an epitope within CelTOS. CelTOS epitopes may be as described in Section I(a). Specifically, the anti-CelTOS antibodies may specifically bind an epitope of an Apicomplexan CelTOS within the sequences highlighted in the green block in FIG. 1. More specifically, anti-CelTOS antibodies useful herein include antibodies that bind one or more of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO: 75 or SEQ ID NO:76.

The term "antibody' includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv, regions, of antibodies with this specificity.

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are typically properly cross-linked via disulfide bonds, as is known.

The basic antibody structural unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-CelTOS antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the CelTOS protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-CelTOS antibody that is composed partially or fully of amino acid sequence sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for CelTOS is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-CelTOS antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, et al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the disclosure specifically binds CelTOS. The phrase "specifically binds" herein means antibodies bind to the protein with an affinity constant or Affinity of interaction ($K_D$) in the range of at least 0.1 mM to 1 pM, or in the range of at least 0.1 pM to 10 nM, with a preferred range being 0.1 pM to 1 nM. Methods of determining whether an antibody binds to CelTOS are known in the art.

The antibodies of the present disclosure may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present disclosure are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

An isolated antibody of the present disclosure that binds to CelTOS preferably recognizes one of several epitopes. For example, an antibody of the disclosure that binds to CelTOS may be an antibody depicted in Table 1.

TABLE 1

Exemplary Antibodies

| mAb | Antigen | Isotype | Cross Reactive | Partial Epitope Mapping (as range) |
|---|---|---|---|---|
| 7G7 | Pv | IgG1 | + | 51-76 |
| 6F11 | Pv | IgG1 | − | 76-137 |
| 6D2 | Pv | IgG1 | + | 137-169 |
| 6C4 | Pv | IgG1 | − | 76-137 |
| 6E11 | Pv | IgG1 | − | 36-51, 169-177 |
| 6C2 | Pv | IgG1 | + | 137-177 |
| 2F12 | Pf | IgG1 | + | 76-137 |
| 4H12 | Pf | IgG1 | − | 51-177 |
| 4D1 | Pf | IgG1 | + | 136-177 |

In one embodiment, the isolated antibody of the present disclosure that binds to CelTOS recognizes an epitope within the C-terminal helices. In another embodiment, the isolated antibody of the present disclosure that binds to CelTOS recognizes an epitope within the sequences highlighted in the green block in the figure depicted above. In still another embodiment, the isolated antibody of the present disclosure that binds to CelTOS recognizes an epitope comprising SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO: 75 or SEQ ID NO:76. In all instances, an antibody of the disclosure blocks CelTOS function in vitro and blocks mosquito parasite transmission in the mosquito vector.

In one embodiment, an antibody of the disclosure may be derived from the hybridoma 4H12, and may comprise an amino acid sequence with 90%, 91%, 92%, 93%, 94%, 95%, 96% 97%, 98%, or 99% identity to the heavy chain variable region of SEQ ID NO:77 (EVQLQESGPELVKP-GASVKISCKASGYALSSSWLNWVKQRPGQGLEWIG-RIFPGDG DTNYNGKFKGKATLTADKSSSTAY-LQLSSLTSVDSAVYFCARGGTWFDYWGQGTTL TVSS), and/or may comprise an amino acid sequence with 90%, 91%, 92%, 93%, 94%, 95%, 96%, 97%, 98%, or 99% identity to the light chain variable region of SEQ ID NO:78 (DIVMTQSHKFMSTSVGDRVNITCKASQDVGIA-VAWYQQRPGQSPKLLIYWASKRHTG VHDRFTGTGFGTDFTLTISTVQSEDLA-DYFCQQYSNSLTFGAGTTLEL). In one embodiment, an antibody comprises one or more CDRs from the heavy chain variable region comprising SEQ ID NO:77 and one or more CDRs from the light chain variable region comprising SEQ ID NO:78. In an exemplary embodiment, an antibody of the disclosure that binds to CelTOS comprises the heavy chain amino acid sequence of SEQ ID NO:77 and the light chain amino acid sequence of SEQ ID NO:78 [i.e. the monoclonal antibody referred to as 4H12].

In one embodiment, an antibody of the disclosure may be derived from the hybridoma 7G7, and may comprise an amino acid sequence with 90%, 91%, 92%, 93%, 94%, 95%, 96% 97%, 98%, or 99% identity to the heavy chain variable region of SEQ ID NO:79 (QLQESGPELVKP-GASVKVSCKASGYSFTDYNMYWVKQSHGKSLEWI-GYIDPYNGGT RYNQKFRDKATLTVDKSSSTAFMHLNSLTSED-SAVYYCARGYYYGNPLHFDVWGAGT TVTVSS), and/or may comprise an amino acid sequence with 90%, 91%, 92%, 93%, 94%, 95%, 96%, 97%, 98%, or 99% identity to the light chain variable region of SEQ ID NO:80 (QIVLTQ-SPAIMSASPGEKVTMTCSASSSVSYIHVVYQQKSGT-SPKRWIYDTSKLASGVP ARFSGSGSGTSYSLTISSME-AEDAATYYCQQWISYPATFGAGTKLELK). In one embodiment, an antibody comprises one or more CDRs from the heavy chain variable region comprising SEQ ID NO:79 and one or more CDRs from the light chain variable region comprising SEQ ID NO:80. In an exemplary embodiment, an antibody of the disclosure that binds to CelTOS comprises the heavy chain amino acid sequence of SEQ ID NO:79 and the light chain amino acid sequence of SEQ ID NO:80 [i.e. the monoclonal antibody referred to as 7G7].

In one embodiment, an antibody of the disclosure may be derived from the hybridoma 6C4, and may comprise an amino acid sequence with 90%, 91%, 92%, 93%, 94%, 95%, 96% 97%, 98%, or 99% identity to the heavy chain variable region of SEQ ID NO:81 (ASVRLSCKASGYTFTDYY-INWVKQRTGQGLEWIGEIYPGTGN-TYYNEKFKDKATLTAD TSSSTAYMQLSSLTSED-SAVYFCARKIYYYGISGYAMDYWGQGTSVTVSSAK-TTPPSV YPLAPGSAAQTNSMVTLGCLVKGYF-PEPVTVTWNSGSLSSGVATFQ), and/or may comprise an amino acid sequence with 90%, 91%, 92%, 93%, 94%, 95%, 96%, 97%, 98%, or 99% identity to the light chain variable region of SEQ ID NO:82 (LSGVEGDI-VMTQSHKFMSTSVGDRVSIICKARQDVGTAVAV-VYQQKPGQSXKLLIYVVA STRHTGVPDRFTGSGSGTDFTLTISNVQSEDLA-DYFCQQYSRYALTFG). In one embodiment, an antibody comprises one or more CDRs from the heavy chain variable region comprising SEQ ID NO:81 and one or more CDRs from the light chain variable region comprising SEQ ID NO:82. In an exemplary embodiment, an antibody of the disclosure that binds to CelTOS comprises the heavy chain amino acid sequence of SEQ ID NO:81 and the light chain amino acid sequence of SEQ ID NO:82 [i.e. the monoclonal antibody referred to as 6C4]. In each of the above embodiments, the antibody may be humanized.

(c) Duffy Binding Protein (DBP)

The present invention also provides immunogenic compositions and antibodies comprising and/or targeting DBP epitopes such as those described in application Ser. No. 15/160,784 filed on May 20, 2016, entitled "SYNTHETIC PLASMODIUM ANTIGENS, COMPOSITIONS, AND USES THEREOF", which is hereby incorporated by reference in its entirety. It should be understood that the compositions and methods as described herein relating to Cel-TOS can be used to make and use similar compositions utilizing DBP epitopes, immunogens and antibodies.

(d) Pharmaceutical Compositions

The immunogenic composition or antibody disclosed herein can be formulated into various dosage forms and administered by a number of different means that will deliver a therapeutically effective amount of the antigen or antibody. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be an intramuscular formulation.

Solid dosage forms for oral administration include capsules, tablets, caplets, pills, powders, pellets, and granules. In such solid dosage forms, the active ingredient is ordinarily combined with one or more pharmaceutically acceptable excipients. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, an antigen or antibody of the disclosure is encapsulated in a suitable vehicle to either aid in the delivery of the antigen or antibody to target cells, to increase the stability of the composition, or to minimize potential toxicity of the composition. As will be appreciated by a skilled artisan, a variety of vehicles are suitable for delivering a composition of the present disclosure. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of antigen or antibody in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, antigen may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), phosphatidylethanolamine (PE), and linear polyethylenimine (I-PEI). In a specific embodiment, the liposome may be comprised of linear polyethylenimine (I-PEI). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying antigen or antibody may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the disclosure may be delivered as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the disclosure generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The antigen or antibody may be encapsulated in a microemulsion by any method generally known in the art.

In yet another embodiment, antigen or antibody may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the disclosure. Generally, the size of dendrimers may range from about 1 nm to about 100 nm.

II. Methods

In an aspect, the present disclosure provides a method of treating a CelTOS-associated infection in a subject. The method comprises administering to the subject an effective amount of an immunogenic composition comprising Apicoplexan CelTOS of the disclosure. Alternatively, the method comprises administering to the subject an effective amount of an immunogenic composition comprising *Plasmodium, Babesia, Theileria* or *Cytauxzoon* CelTOS of the disclosure. Further, the method comprises administering to the subject an effective amount of an immunogenic composition comprising *Babesia, Theileria* or *Cytauxzoon* CelTOS of the disclosure. Alternatively, the method comprises administering to the subject an effective amount of a composition comprising an anti-CelTOS antibody of the disclosure. The term "infection" as used herein includes presence of parasites, in or on a subject, which, if its growth were inhibited, would result in a benefit to the subject. A "CelTOS-associated infection" may be an apicomplexan parasite infection. In an embodiment, the CelTOS-associated infection may be an infection caused by an apicomplexan parasite selected from the group consisting of *Plasmodium, Babesia, Theileria* or *Cytauxzoon* species. In another embodiment, the CelTOS-associated infection may be an infection caused by an apicomplexan parasite selected from the group consisting of *Babesia, Theileria* or *Cytauxzoon* species. A CelTOS-associated infection may be a pre-erythrocyte parasitic infection. Accordingly, CelTOS may be a target antigen for a pre-erythrocytic vaccine. Vaccination with a pre-erythrocytic stage vaccine reduces or eliminates the traversal of infective sporozoites through cells required for infection of liver cells and thus protect against infection and/or reduce the severity of the disease. A pre-erythrocytic vaccine would protect against the infectious form (sporozoite) injected by a mosquito and/or inhibit parasite development in the liver. In a previously unexposed individual, if a few parasites were to escape the immune defences induced by a pre-erythrocytic vaccine, they would eventually enter the blood-stage, multiply within the erythrocytes and establish a full-blown disease. In an aspect, a vaccine composition comprising a CelTOS immunogen of the disclosure or a composition comprising an anti-CelTOS antibody may treat an infection caused by Apicomplexan parasites. In another aspect, a vaccine composition comprising a CelTOS immunogen of the disclosure or a composition comprising an anti-CelTOS antibody may treat an infection caused by *Plasmodium, Babesia, Theileria* or *Cytauxzoon*. In another aspect, a vaccine composition comprising a CelTOS immunogen of the disclosure or a composition comprising an anti-CelTOS antibody may treat an infection caused by *Babesia, Theileria* or *Cytauxzoon*. Routine experimentation would allow a skilled artisan to determine if the parasitic infection is mediated by CelTOS. Non-limiting examples of infections that may be prevented or treated using the compositions and/or methods of the disclosure include: babesiosis (*Babesia*), malaria (*Plasmodium*), theileriosis (*Theileria annulata*), East Coast fever (*Theileria parva*), cytauxzoonosis (*Cytauxzoon felis*), coccidian diseases including Cryptosporidiosis (*Cryptosporidium parvum*), Cyclosporiasis (*Cyclospora cayetanensis*), isosporiasis (*Isospora belli*) and toxoplasmosis (*Toxoplasma gondii*).

The term "treat", "treating" or "treatment" as used herein refers to administering a pharmaceutical composition of the invention for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering a pharmaceutical composition of the invention in order to: (i) reduce or eliminate either a CelTOS-associated infection or one or more symptoms of the CelTOS-associated infection, or (ii) retard the progression of a CelTOS-associated infection or of one or more symptoms of the CelTOS-associated infection, or (iii) reduce the severity of a CelTOS-associated infection or of one or more symptoms of the CelTOS-associated infection, or (iv) suppress the clinical manifestation of a CelTOS-associated infection, or (v) suppress the manifestation of adverse symptoms of the CelTOS-associated infection.

The term "control" or "controlling" as used herein generally refers to preventing, reducing, or eradicating a CelTOS-associated infection or inhibiting the rate and extent of such an infection, or reducing the parasitic population, such as a parasitic population present in or on a subject, wherein such prevention or reduction in the CelTOS-associated infection or microbial population is statistically significant with respect to untreated infection or population. In general, such control may be achieved by increased mortality amongst the parasitic population.

The compositions of the present disclosure may be used to protect or treat a subject susceptible to infection by a CelTOS-expressing parasite, or more preferably, by *Plasmodium, Babesia, Theileria* or *Cytauxzoo* spp., by means of administering said composition directly to a subject. The term "administration" or "administering" includes delivery of a composition or one or more pharmaceutically active ingredients to a subject, including for example, by any appropriate methods, which serves to deliver the composition or it's active ingredients or other pharmaceutically active ingredients to the site of the infection. The method of administration can vary depending on various factors, such as for example, the components of the pharmaceutical composition or the type/nature of the pharmaceutically active or inert ingredients, the site of the potential or actual infection, the microorganism involved, severity of the infection, age and physical condition of the subject. Direct delivery may be accomplished by parenteral injection (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In one embodiment, administration is by intramuscular injection to the thigh or the upper arm. Injection may be via a needle (e.g. a hypodermic needle, electroporation device), but needle free injection may alternatively be used. A typical intramuscular dose is 0.5 mL. The composition can be administered prophylactically (i.e. to prevent infection) or therapeutically (i.e. to treat infection). An immune response is preferably protective. The method may raise a booster response.

The invention provides a method for treating a CelTOS-associated infection in a subject, comprising the step of administering an effective amount of a composition of the disclosure. The term "effective amount" as used herein refers to an amount, which has a therapeutic effect or is the amount required to produce a therapeutic effect in a subject. For example, a therapeutically or pharmaceutically effective amount of a composition is the amount of the antigen required to produce a desired therapeutic effect as may be judged by clinical trial results and/or model animal infection studies. The effective or pharmaceutically effective amount depends on several factors, including but not limited to, the route of administration, the parasite involved, characteristics of the subject (for example height, weight, sex, age and medical history), severity of infection, location of infection, the particular type of antigen used and/or the particular antibody used. For prophylactic treatments, a therapeutically or prophylactically effective amount is that amount which would be effective to prevent a parasite infection.

The effective amount of antigen in each vaccine dose is selected as an amount which induces an immunoprotective response without significant adverse side effects in typical vaccines. Accordingly, the exact amount of the antigen that is required to elicit such a response will vary from subject to subject, depending on the species, age, and general condition of the subject, the severity of the condition being treated, the particular carrier or adjuvant being used and its mode of administration, and the like. Generally it is expected that each dose will comprise 1-1000 pg of total antigen, or 1-100 pg, or 1-40 pg, or 1-5 pg, or less than 1 pg. An optimal amount for a particular vaccine can be ascertained by studies involving observation of antibody titres and other responses in subjects. In certain embodiments, the vaccine composition is administered at a dose ranging from about 50 to 150 pg. In another embodiment, the vaccine composition is administered at a dose of about 100 pg. In still another embodiment, the vaccine composition is administered at a dose ranging from 0.3 to 100 pg.

The concentration of anti-CelTOS antibody in compositions to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition comprising an anti-CelTOS antibody for injection to a living subject could be made up to contain from 1-5 mL sterile buffered water of phosphate buffered saline and about 1-5000 mg of anti-CelTOS antibody. A typical composition for intravenous infusion could have volumes between 1-250 mL of fluid, such as sterile Ringer's solution, and 1-100 mg per ml, or more in anti-CelTOS antibody concentration. Doses will vary from subject to subject based on size, weight, and other physiobiological characteristics of the subject receiving the successful administration. In an aspect, a typical dose contains from about 0.01 mg/kg to about 100 mg/kg of an anti-CelTOS antibody described herein. Doses can range from about 0.05 mg/kg to about 100 mg/kg, more preferably from about 0.1 mg/kg to about 50 mg/kg, or from 0.5 mg/kg to about 50 mg/kg, or from about 10 mg/kg to about 50 mg/kg. In a specific embodiment, the dose of anti-CelTOS antibody may range from about 10 mg/kg to about 50 mg/kg.

Following initial administration of a composition of the disclosure, subjects may receive one or several additional administrations of the composition adequately spaced. Dosing treatment can be a single dose schedule or a multiple dose schedule. Suitable timing between doses (e.g. between 4-16 weeks) can be routinely determined.

In the prevention of an infection, a composition of the disclosure may be administered as multiple doses prior to infection or prior to insertion of the medical device or implanted material. In the treatment of an infection, a composition of the disclosure may be administered as multiple doses following infection or following insertion of the medical device or implanted material. Administration may be daily, twice daily, weekly, twice weekly, monthly, twice monthly, every 6 weeks, every 3 months, every 6 months or yearly. For example, administration may be every 2 weeks, every 3 weeks every 4 weeks, every 5 weeks, every 6 weeks, every 7 weeks, every 8 weeks, every 9 weeks, every 10 weeks, every 11 weeks or every 12 weeks. Alternatively, administration may be every 1 month, every 2 months, every 3 months, every 4 months, every 5 months, every 6 months, every 7 months, every 8 months, every 9 months, every 10 months, every 11 months or every 12 months. Still further, administration may be every 1 year, every 2 years, every 3 years, every 4 years, every 5 years, every 6 years, every 7 years, every 8 years, every 9 years, every 10 years, every 15 years or every 20 years. The duration of treatment can and will vary depending on the subject and the infection to be prevented or treated. For example, the duration of treatment may be for 1 week, 2 weeks, 3 weeks, 4 weeks, 5 weeks, 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, administration may be every 4 weeks for 6 months to a year and then administration may be every year thereafter. The duration of treatment may also depend on the length of time the medical device or implanted material is to remain in the subject. For example, when the medical device or implanted material is to remain in the subject for a long period of time, the duration of treatment may be extended. In contrast, when the medical device or implanted material is to remain in the subject for a shorter period of time, the duration of treatment may be shortened. In a specific embodiment, the duration of treatment may be once a day for the duration of time the medical device or implanted material remains in a subject. A skilled artisan would be able to determine the effective dosing regimen based on the medical history and duration of indwelling device in the subject.

A method of the disclosure may further comprise administering an antiparasitic agent. As used herein, an "antiparasitic agent" is an agent that kills parasites or inhibits their growth. Non-limiting examples of antiparasitic agents include broad-spectrum agents such as nitazoxanide and antiprotozoals such as melarsoprol, eflornithine, metronidazole, tinidazole, miltefosine.

As used herein, "subject" or "patient" is used interchangeably. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In certain embodiments, the subject is a human, a livestock animal, or a companion animal. In other embodiments, the subject is a cow. In still other embodiments, the subject is a cat.

(a) Methods of Using Anti-CelTOS Antibodies

In another aspect, the present invention encompasses methods for detecting a CelTOS-associated infection. The method comprises (a) contacting a biological sample obtained from a subject with an anti-CelTOS antibody of the disclosure, and (b) identifying or diagnosing a subject as having a CelTOS-associated infection when the antibody recognizes CelTOS present in the biological sample. Alternatively, the method generally comprises (a) measuring the amount of CelTOS in a biological sample obtained from a subject using an anti-CelTOSs antibody of the disclosure, (b) comparing the amount of CelTOS in the sample to a reference value, and (c) classifying the subject as having a high or low amount of CelTOS relative to the reference value based on the amount of CelTOS measured in the sample.

As used herein, the term "biological sample" refers to a sample obtained from a subject. Any biological sample containing CelTOS is suitable. Numerous types of biological samples are known in the art. Suitable biological sample may include, but are not limited to, tissue samples or bodily fluids. In some embodiments, the biological sample is a tissue sample such as a tissue biopsy of tissues, bone, muscle, cartilage, or skin. The tissue biopsy may be a biopsy of a known or suspected infection. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. In other embodiments, the sample may be a bodily fluid. Non-limiting examples of suitable bodily fluids include blood, plasma, serum, urine, saliva, sputum, ascites, pleural effusion, or cerebrospinal fluid. The fluid may be used "as is", the cellular components may be isolated from the fluid, or a protein fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that CelTOS can be accurately detected and the amount measured according to the disclosure.

Once a sample is obtained, it is processed in vitro to detect and measure the amount of CelTOS using an anti-CelTOS antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of CelTOS comprises contacting some of the sample, or all of the sample, comprising CelTOS with an anti-CelTOS antibody under conditions effective to allow for formation of a complex between the antibody and the CelTOS. Typically, the entire sample is not needed, allowing one skilled in the art to repeatedly detect and measure the amount of CelTOS in the sample. The method may occur in solution, or the antibody or CelTOS comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-CelTOS antibody may also be attached to the substrate non-covalently. For example, a biotinylated anti-CelTOS antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-CelTOS antibody composition to the sample and incubating the mixture for a period of time long enough for the anti-CelTOS antibody to bind to any antigen present. After this time, the complex will be washed and the complex may be detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-CelTOS antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-CelTOS antibody attached to the substrate is located at one or more spatially defined addresses of the array. For example, an array may comprise at least one, at least two, at least three, at least four, or at least five anti-CelTOS antibodies, each antibody recognizing the same or different CelTOS epitope, and each antibody may be at one, two, three, four, five, six, seven, eight, nine, ten or more spatially defined addresses.

Any suitable reference value known in the art may be used. For example, a suitable reference value may be the amount of CelTOS in a biological sample obtained from a subject or group of subjects of the same species that has no detectable CelTOS-associated infection. In another example, a suitable reference value may be the amount of CelTOS in biological sample obtained from a subject or group of subjects of the same species that has detectable CelTOS-associated infection as measured via standard methods such as culture. In another example, a suitable reference value may be a measurement of the amount of CelTOS in a reference sample obtained from the same subject. The reference sample comprises the same type of biological fluid as the test sample, and may or may not be obtained from the subject when CelTOS-associated infection was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began.

According to the disclosure, a subject may be classified based on the amount of CelTOS measured in the sample. Classifying a subject based on the amount of CelTOS measured in a sample of biological fluid obtained from the subject may be used to identify subjects with a CelTOS-associated infection. Generally speaking, a subject may be classified as having a high or low amount of CelTOS compared to a reference value, wherein a high amount of CelTOS is an amount above the reference value and a low amount is an amount equal to or below the reference value. In preferred embodiments, to classify a subject as having a high amount of CelTOS, the amount of CelTOS in the sample compared to the reference value may be at least 5% greater. For example, the amount of CelTOS in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of CelTOS in the sample of biological fluid obtained from the subject compared to the reference value may be increased at least 2-fold. For example, the amount of CelTOS in the sample compared to the reference value may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold.

In another aspect, the invention provides means to detect a CelTOS-associated infection in a subject. A CelTOS-associated infection is as described above in Section II.

Upon detection of a CelTOS-associated infection, the subject may be treated via methods standard in the art for treating infection or the subject may be treated with compositions disclosed herein or a combination thereof. Such treatment methods may depend on the type and severity of the CelTOS-associated infection, as well as the general condition of the patient. Standard treatment of infection consists primarily of antiparasitic therapy. Antiparasitic agents utilized for antiparasitic therapy may be as described herein.

In an embodiment, a method for monitoring CelTOS-associated infection in a subject may be used to determine infection progression. In such an embodiment, a method of detecting CelTOS may be used to assess the risk of a subject at one point in time, then at a later time, the method of detecting CelTOS may be used to determine the change in risk of the subject over time. For example, the method of detecting CelTOS may be used on the same subject days, weeks, months or years following the initial determination of the amount of CelTOS. Accordingly, the method of detecting CelTOS may be used to follow a subject to determine when the risk of progressing to more severe infection is high thereby requiring treatment. Additionally, the method of detecting CelTOS may be used to measure the rate of infection progression. For example, a depressed amount of CelTOS may indicate an abatement of infection. Alternatively, an elevated amount of CelTOS may indicate infection progression. Levels may be monitored hourly, daily, weekly, monthly, etc. so as to track the progression/remission of a CelTOS-associated infection such as during the period of hospitalization, the duration of treatment, and/or the duration of indwelling device.

In another embodiment, a method for monitoring CelTOS-associated infection in a subject may also be used to determine the response to treatment. As used herein, subjects who respond to treatment are said to have benefited from treatment. For example, a method to detect CelTOS may be performed on the biological sample of the subject prior to initiation of treatment, then at a later time, a method to detect CelTOS may be used to determine the response to treatment over time. For example, a method to detect CelTOS may be performed on the biological sample of the same subject days, weeks, months or years following initiation of treatment. Accordingly, a method to detect CelTOS may be used to follow a subject receiving treatment to determine if the subject is responding to treatment. If the amount of CelTOS remains the same or decreases, then the subject may be responding to treatment. If the amount of CelTOS increases, then the subject may not be responding to treatment. These steps may be repeated to determine the response to therapy over time.

For each aspect, the method generally comprises (a) measuring the amount of CelTOS in a biological sample obtained from a subject using an anti-CelTOS antibody, and (b) comparing the amount of CelTOS in the sample to a reference value. A greater amount of CelTOS in the sample compared to the reference value indicates the presence of a CelTOS-associated infection. The amount of CelTOS may be a qualitative, a semi-quantitative or quantitative measurement. Suitable anti-CelTOS antibodies are described above, as are methods for measuring the amount of CelTOS in a biological sample. In a preferred embodiment, the biological sample is biological fluid selected from the group consisting of urine, sputum, blood, plasma, and serum.

III. Kits

In an embodiment, an antibody of the disclosure may be used in a kit to diagnose a CelTOS-associated infection. The CelTOS-associated infection may be an apicomplexan parasite infection. In an embodiment, the CelTOS-associated infection may be an infection caused by an apicomplexan parasite selected from the group consisting of *Plasmodium, Babesia, Theileria* or *Cytauxzoon* species. In another embodiment, the CelTOS-associated infection may be an infection caused by an apicomplexan parasite selected from the group consisting of *Babesia, Theileria* or *Cytauxzoon* species. Such kits are generally known in the art and commonly used to detect an antigen or parasite of interest. These diagnostic kits will generally include the antibodies of the disclosure along with suitable means for detecting binding by that antibody such as would be readily understood by one skilled in this art. For example, the means for detecting binding of the antibody may comprise a detectable label that is linked to said antibody. Non-limiting examples of suitable labels include enzymes, radioactive isotopes, fluorescent compounds, chemical compounds, and bioluminescent proteins. These kits can then be used in diagnostic methods to detect the presence of a CelTOS-associated infection wherein a sample is collected from a subject suspected of being infected by one or more Apicomplexan parasites.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

These examples provide for the generation of monoclonal antibodies (mAbs) to *P. falciparum* and *P. vivax* CelTOS and evaluate the ability of mAbs to neutralize malaria parasites using a novel model system for malaria transmission. Briefly, in this system a luciferase-expressing cassette was integrated into the genome of *P. falciparum* KF7 by the piggyBac transposon system and used to infect the established humanized NSG (NOD.Cg-Prkdcscid Il2rgtm1Sug/JicTac) mouse model. Malaria transmission was quantified by monitoring the luciferase signal from oocysts developing in mosquitoes that had taken up a blood meal from infected mice. CelTOS mAbs are identified that neutralize malaria parasites. Furthermore the mAbs inhibited parasite propagation in host liver cells suggesting that they also block malaria infection in the host. Subsequent biophysical studies reveal that the mAbs inhibit the membrane disruption activity of CelTOS in vitro suggesting that the mechanism by which mAbs neutralize malaria parasites is by impairing CelTOS-mediated membrane disruption. Crystal structures of the mAbs in complex with PfCelTOS and PvCelTOS reveal neutralizing and non-neutralizing epitopes in *Plasmodium* CelTOS. Hydrogen-deuterium exchange mass spectrometry (HDX-MS) confirmed the epitopes identified from the crystal structures. The affinity and stoichiometry of antibody interaction with CelTOS was also determined to further inform the mechanism of these antibodies. In summary, this is the first study to identify the linear and three-dimensional structures of neutralizing and non-neutralizing epitopes in CelTOS, and these findings will inform the design of immunogens to be used in a CelTOS-based transmission- and infection-blocking malaria vaccine.

Example 1—Generation of Mouse Monoclonal Antibodies Against *P. falciparum* and *P. vivax* CelTOS and piggyBac Plasmid pL-BACII-bEDMH-Luc Construction and Helper Plasmid Mouse monoclonal antibodies (mAbs) against the secreted form of *P. falciparum* and *P. vivax* CelTOS were generated. The mAbs Pf4H12 and Pf4D1 were obtained from mice immunized with *P. falciparum* CelTOS, while Pv7G7 and Pv6C4 were obtained after immunization with *P. vivax* CelTOS. All the mAbs obtained were of the IgG isotype and subclass IgG1. Additionally, some mAbs were found to be species cross reactive by ELISA. Pf4D1 also binds *P. vivax* CelTOS, and Pv7G7 also binds *P. falciparum* CelTOS as shown in Table 2.

TABLE 2

Monoclonal antibodies against Plasmodium CelTOS showing the antigen used for immunization, immunoglobulin isotype, subclass and species reactivity.

| Monoclonal Antibody | Antigen | Isotype | Species Reactivity |
|---|---|---|---|
| Pf4H12 | PfCelTOS | IgG1 | PfCelTOS |
| Pf4D1 | PfCelTOS | IgG1 | PfCelTOS and PvCelTOS |

TABLE 2-continued

Monoclonal antibodies against Plasmodium CeITOS showing the antigen used for immunization, immunoglobulin isotype, subclass and species reactivity.

| Monoclonal Antibody | Antigen | Isotype | Species Reactivity |
|---|---|---|---|
| Pv7G7 | PvCeITOS | IgG1 | PvCeITOS and PfCeITOS |
| Pv6C4 | PvCeITOS | IgG1 | PvCeITOS |

Figure 2A:
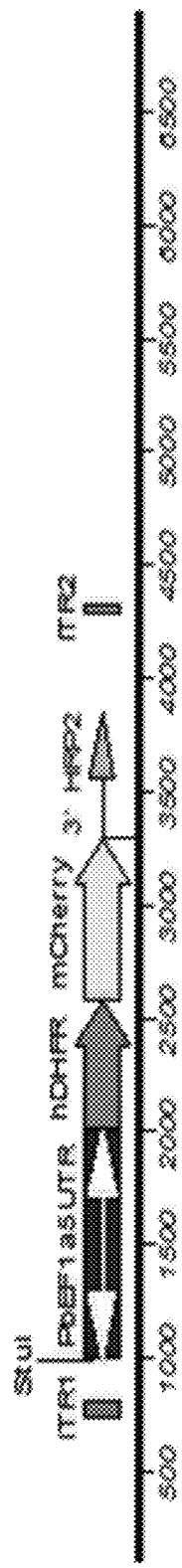
FIG. 2A, FIG. 2B, and FIG. 2C depict the pL-BACII-bEDMH-Luc vector construction and transposase-expressing helper plasmid pDCTH. Luciferase and PbDHFR3' UTR genes were amplified from existing expression cassette and inserted them into a mCherry-hDHFR piggyBac vector pL-BacII-bEDMH to obtain pL-BACII bEDMH-Luc plasmid vector.
Figure 2B:
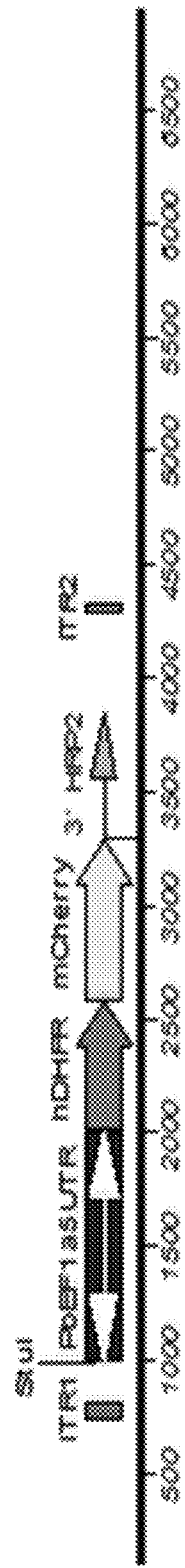
Figure 2C:
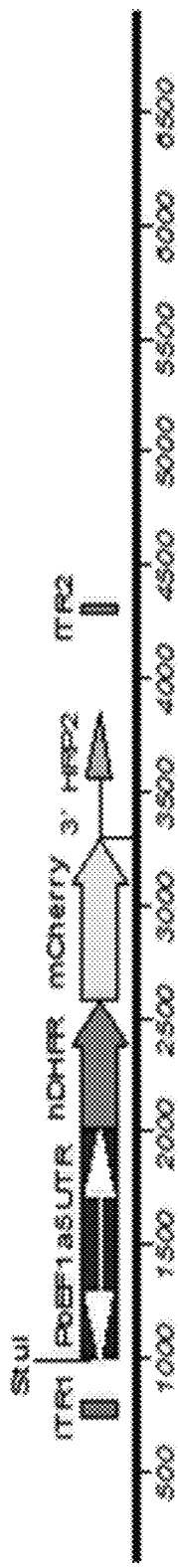

Luciferase and PbDHFR3' UTR genes were amplified from existing expression cassette and inserted them into a mCherry-hDHFR piggyBac vector pL-BACII-bEDMH to obtain pL-BACII-bEDMH-Luc plasmid vector. The vector is designed to express both mCherry and luciferase driven by P. berghei EF1-α that is a constitutive promoter active in all developmental stages of parasite. As described above, luciferase-expressing piggyBac vector pL-bEDMH-Luc driven by P. berghei EF1-α promoter with hDHFR drug selection marker has been constructed (FIG. 2B) based on backbone plasmid pL-BACII-bEDMH (FIG. 2A). The vector was employed to transfect P. falciparum KF7 parasite line by using the erythrocyte loading method with the transposase-expressing helper plasmid pDCTH (FIG. 2C).

Figure 3A:
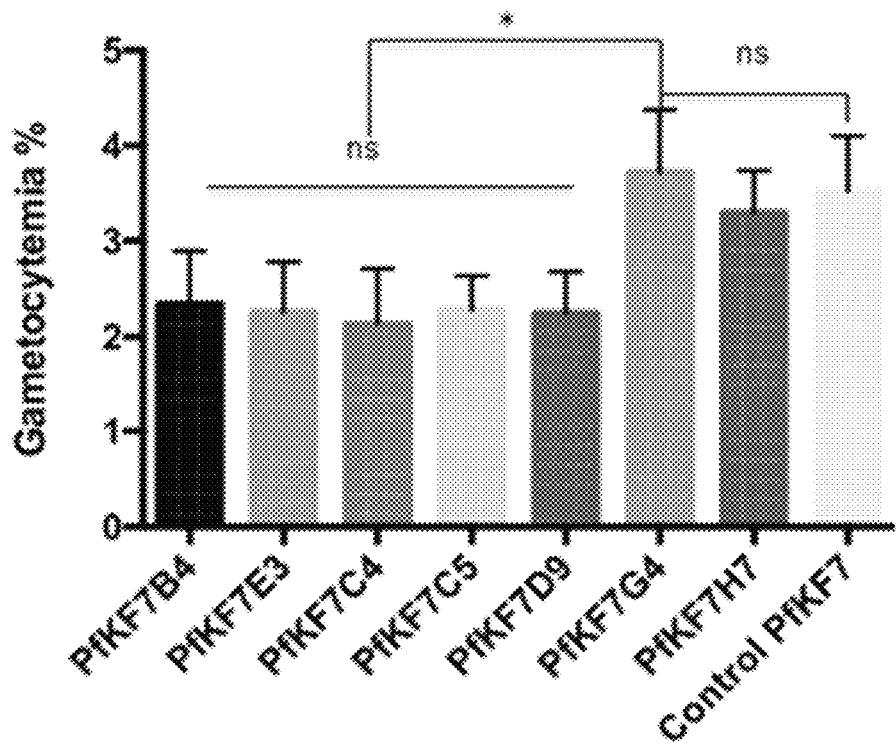
FIG. 3A and FIG. 3B depicts pL-BACII-bEDMH-Luc KF7 clones gametocyte culture in vitro and mosquito luciferase assay.

Transfectants were selected by using 5 nM WR drug depressor in culture medium, cloned by limiting dilution. Seven clones that piggyBac transposon were integrated in genome were confirmed by TAIL-PCR and Sanger sequencing. Integrations occurred at TTAA target sites of either UTR or CDS region in different the genome of the parasite (Table 3). Theses integrated parasite clones express high level of luciferase signals through all stages of parasite blood cycle. In order to develop a luciferase-expressing parasite clone with high rate of gametocyte conversion and detectable by luciferase assay in mosquito-stage when oocyst developing, one time duplicated and two times repeated triplicated gametocyte cultures (n=8) were performed parallel for 7 clones and PfKF7 parasite line as control. On day 17 post starting gametocyte culture, Giemsa-stained blood slides were examined for gametocytemia by counting 20 fields with 500 red blood cells each field (totally counting about 10000 red blood cells). Of these clones, clone PfKF7G4 showed that this luciferase transgenic parasite clone has highest gametocyte conversion rate (FIG. 3A). Gametocytemia of day-17 culture could reach to as high as 4.5%. Kruskal-Wallis test analysis demonstrated clone PfKF7G4 gametocyte conversion rate was significant high comparing to other clones except for clone PfKF7H7 (P<0.05).

Figure 3B:
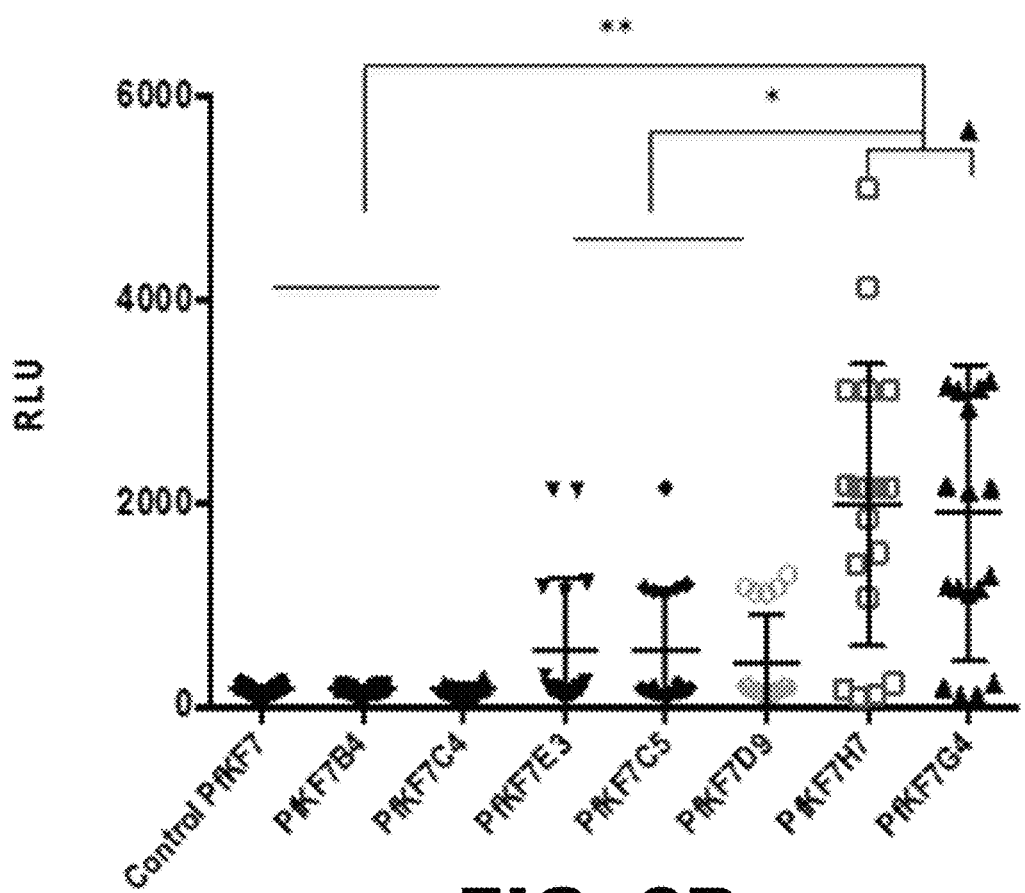

To compare levels of luciferase signal expression among these 7 integrated clones in mosquito stage, the duplicated infected the mosquito sets (100 mosquitoes for each 75-flask gametocytes culture set) of these clone gametocytes culture on day 8 post blood meal were investigated using 96-well plate mosquito luciferase assay described as above in the methods with PfKF7 as luciferase negative control. As shown in FIG. 3B, two clones PfKF7G4 and PfKF7H7 demonstrated the best luciferase activity (P<0.01) after parasite developing 8 days when oocysts had developed. The results matched to those of rate of gametocyte conversion. Though these two clones don't have significant difference in both gametocyte conversion and mosquito infection, PfKF7G4 shown more advantage than PfKF7H7 in liver stage infection experiments (results not showing this paper), which is the reason that we use the PfKF7G4 to do adaption study of humanized mouse model and antibody mediated P. falciparum oocyst inhibition assay as followed.

Figure 4A:
FIG. 4A and FIG. 4B depict huRBC-NSG mice blood flow cytometry (FC) analysis by single staining with anti-human CD235a-APC.
Figure 4B:
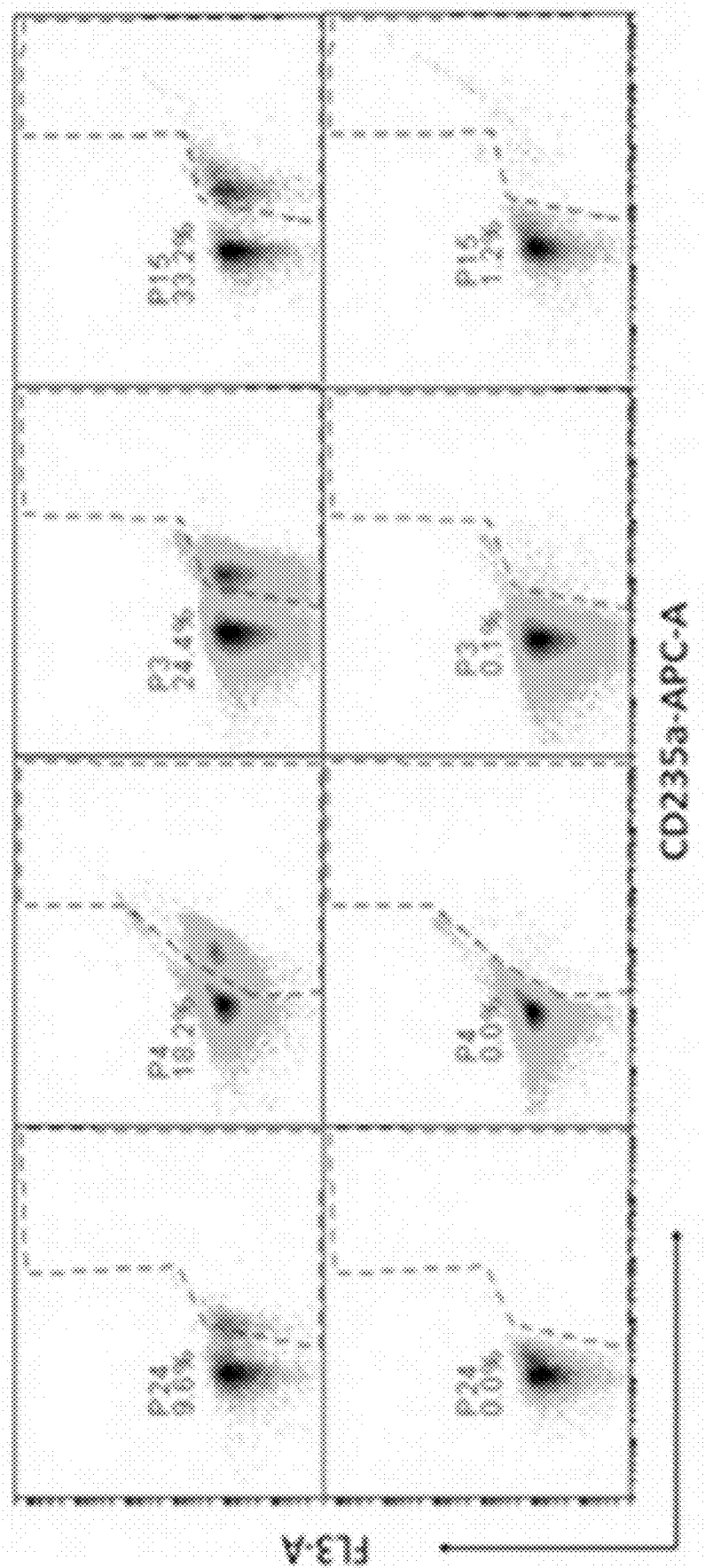

Example 2—Humanized Mouse Models of P. falciparum Infection in Blood Stage and P. falciparum Gametocyte Culture In Vivo with Mouse Adapted PfKF7G4 Parasite To develop blood stage P. falciparum infection mouse model, experiments were performed in NSG mice by macrophage depletion with clodronate liposomes and administration of engrafting of huRBC. Blood samples were collected from mouse lateral tail vein at 12th hour post engraftment of huRBC. 2.5 µl of blood was analyzed for the presence of huRBC using APC-conjugated anti-human CD235a immunofluorescent staining on BD Accuri C6 flow cytometer (FC). Analysis results showed that proportion of huRBC in mouse peripheral blood reached to 25.3% (SD=1.88, n=3) after third huRBC injection, reached to 34.5% (SD=3.590728, n=3) after fourth huRBC injection (FIG. 4A). FIG. 4B depicts representative flow cytometry scatter plots of huRBC proportion in mouse peripheral blood.

Independent series of parasite PfKF7G4 sequential blood to blood in vivo/vitro passages were carried out. huRBC-NSG mice with peripheral huRBC levels greater than 25% were randomized for parasite adaption experiment. Three mice per group were assigned for each parasite adaption selection. First adaption experimental mice were inoculated intravenously PfKF7G4 culture in vitro with 30 million mixed stage parasites each mouse. Infections were monitored using single tube luciferase assay with 2.5 µl of

TABLE 3 pL-BACII-bEDMH-LucKF7 clones TAIL-PCR sequences BLAST

Figure 5:
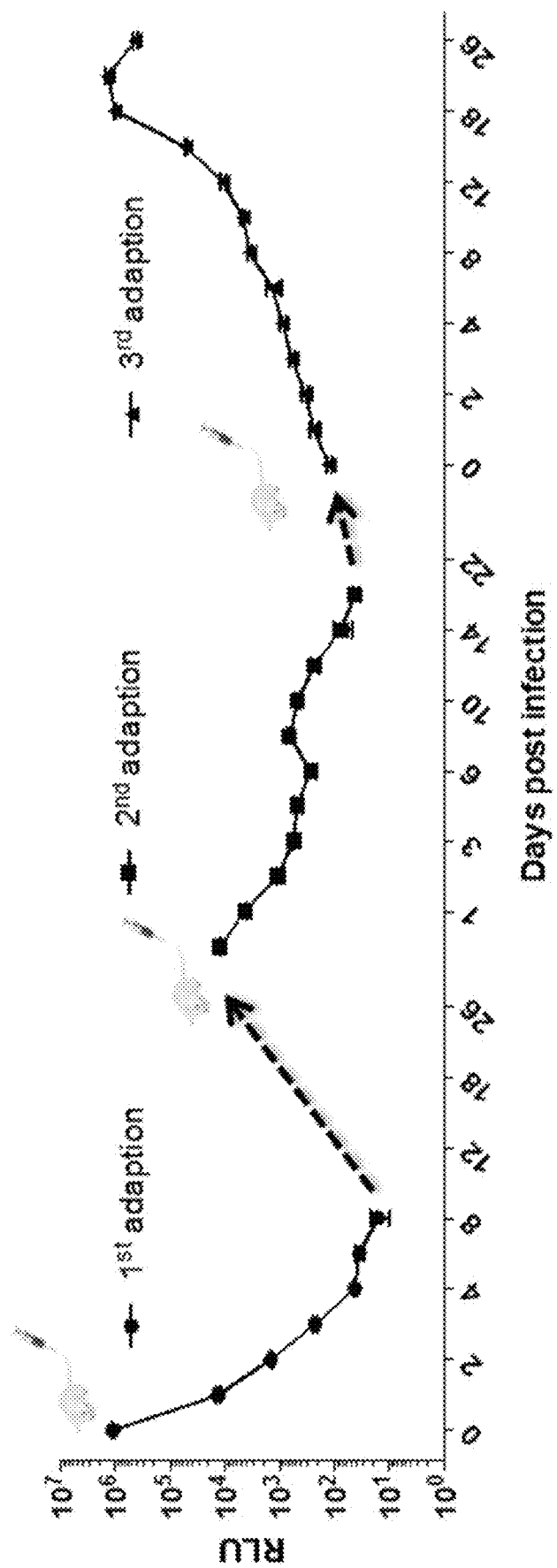
FIG. 5 shows PfKF7G4 parasites were adapted in huRBC-NSG mice. Three huRBC-NSG mice with more than 25% huRBC proportion in mouse blood circulation were selected for each PfKF7G4 mouse-adaption infection. Parasites survived and adapted in mouse were monitored by luciferase assay. The graph shows the mean of 3 measurements of longest luciferase activity lasting mouse blood luciferase activities by RLU on days post infection showed on the X-Axis. Error bars represent standard deviation from 3 measurements. 1st adaption RLU mean±SD=16±6.08 on day 8 post infection, 2nd adaption RLU mean±SD=42±7.00 on day 18 post infection and 3rd adaption RLU mean±SD=1399437±173885 on day 22 post infection when the mean of mouse blood thin parasitemia is 10.58%±0.59 (n=3).

| Clones | Chromosome | Relative gene | Function |
|---|---|---|---|
| B4 | 6 | PF3D7_0602000 CDS | conserved Plasmodium protein, unknown function |
| E3 | 14 | PF3D7_1414500 CDS | atypical protein kinase, ABC-1 family |
| H7 | 10 | PF3D7_1041300 5'UTR | erythrocyte membrane protein 1, PfEMP1 |
| H7 | 3 | PF3D7_0324900 5'UTR | var (3D7-varT3-2) |
| C5 | 12 | PF3D7_1209900 CDS | ABC transporter, (TAP family), putative conserved Plasmodium membrane protein, |
| G4 | 13 | PF3D7_1326900 CDS | unknown function |
| C4 | 12 | PF3D7_1231800 3'UTR | asparagine-rich protein, putative |
| C4 | 12 | PF3D7_1231700 5'UTR | conserved Plasmodium protein |
| D9 | 8 | PF3D7_08163000 CDS | Conserved Plasmodium protein, unknown function | infected mouse tail vein blood until the luciferase activity went down to negative (RLU less than 20). Collected blood from longest luciferase activity lasting mouse by cardiac puncture. Few parasites adapted in mouse from collected blood were recovered and cultured in vitro. Recovered the parasite took 4 weeks to reached to 3% parasitemia. Second adaption experimental mice were inoculated intravenously recovered PfKF7G4 culture in vitro from first adaption experiment with 3 million mixed stage parasites each mouse and same protocol for third adaption experimental mice with 0.3 million parasites each mouse. Luciferase transgenic PfKF7G4 clone parasites have been adapted well in huRBC-NSG mice after 3 times adaption infections (FIG. 5). Followed the mouse model study showed that adapted PfKF7G4 could undergo successive cycles of infection to form complex blood stage parasites, including mature gametocytes, which can develop oocysts and sporozoites in mosquito stage. The adapted PfKF7G4 parasites keep luciferase activity from blood ring stage to oocysts and sporozoites development in mosquito stage. It lays the foundation for establishing the luciferase-based antibody mediated *P. falciparum* oocyst inhibition assay in vivo.

Figure 6:
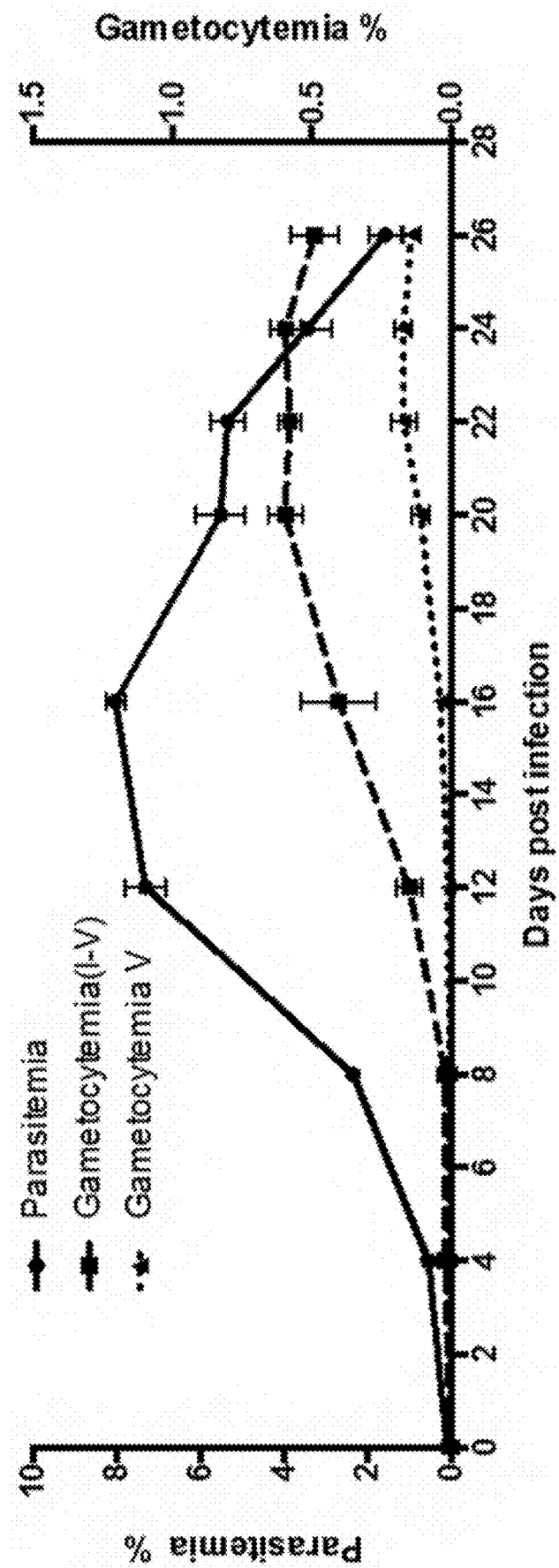
FIG. 6 shows *P. falciparum* gametocyte culture in vivo with mouse adapted PfKF7G4 parasite. Parasitemia and gametocytemia are shown as percentages of total erythrocytes found in mouse peripheral blood measured on Giemsa-stained thin smears during 26 days of infection. The left Y-Axis on the plots are percent (%) parasitemia and the right Y-Axis on the plots are percent (%) gametocytemia for different days post infection on the X-Axis. The error bars represent standard deviation from the mean of biological triplicate measurements.

To explore the feasibility of the NSG mouse model as an antibody mediated *P. falciparum* oocyst inhibition assay for mosquito stage, we developed the mode of gametocyte culture in vivo with huRBC-NSG mice based on preliminary experiments. Selected 4-times huRBC engrafted mice with more than 32% huRBC proportion in blood starting gametocyte culture by adapted PfKF7G4 parasite infection. Monitored the infection with parasitemia and gametocytemia by examination of Giemsa-stained thin blood smears of infected mouse tail blood at the time points showing on X-Axis in FIG. 6 until day 26 post infection. In these mice, the parasitemias reached levels of $0.11\pm0.026\%$ (n=3) 2 hours after initial infection of 1.25 million/mouse mixed stage mouse-adapted PfKF7G4 parasites on day 0. Mouse-adapted PfKF7G4 parasites grew rapidly in infected mice from day 4 to day 12 with routinely huRBC engraftment. Parasitemia levels reached to $7.317\pm0.482\%$ (n=3) in infected mouse blood on day 12 when gametocytes showed detectable by thin tail blood smears with decreasing huRBC engraftment. From day 16 to day 24, even the parasitemia showed going down gradually, but gametocytemia showed going up and more gametocytes matured to stage V gametocytes. Mature gametocyte numbers stay on relative stable levels from day 22 ($0.17\pm0.046\%$) to day 24 ($0.17\pm0.030\%$). The followed mosquito luciferase assay by gametocytes cultured in vivo confirmed gametocytes in infected huRBC-NSG mice on day 22 transmitted mosquitoes to form detectable luciferase expressing oocysts. The results demonstrate that mouse-adapted PfKF7G4 *P. falciparum* parasites can grow to form mature gametocytes and the peak phage period for mature gametocytes in this mode of gametocyte culture in vivo is between day 22 and day 24 post mouse infection (FIG. 6).

Figure 7:
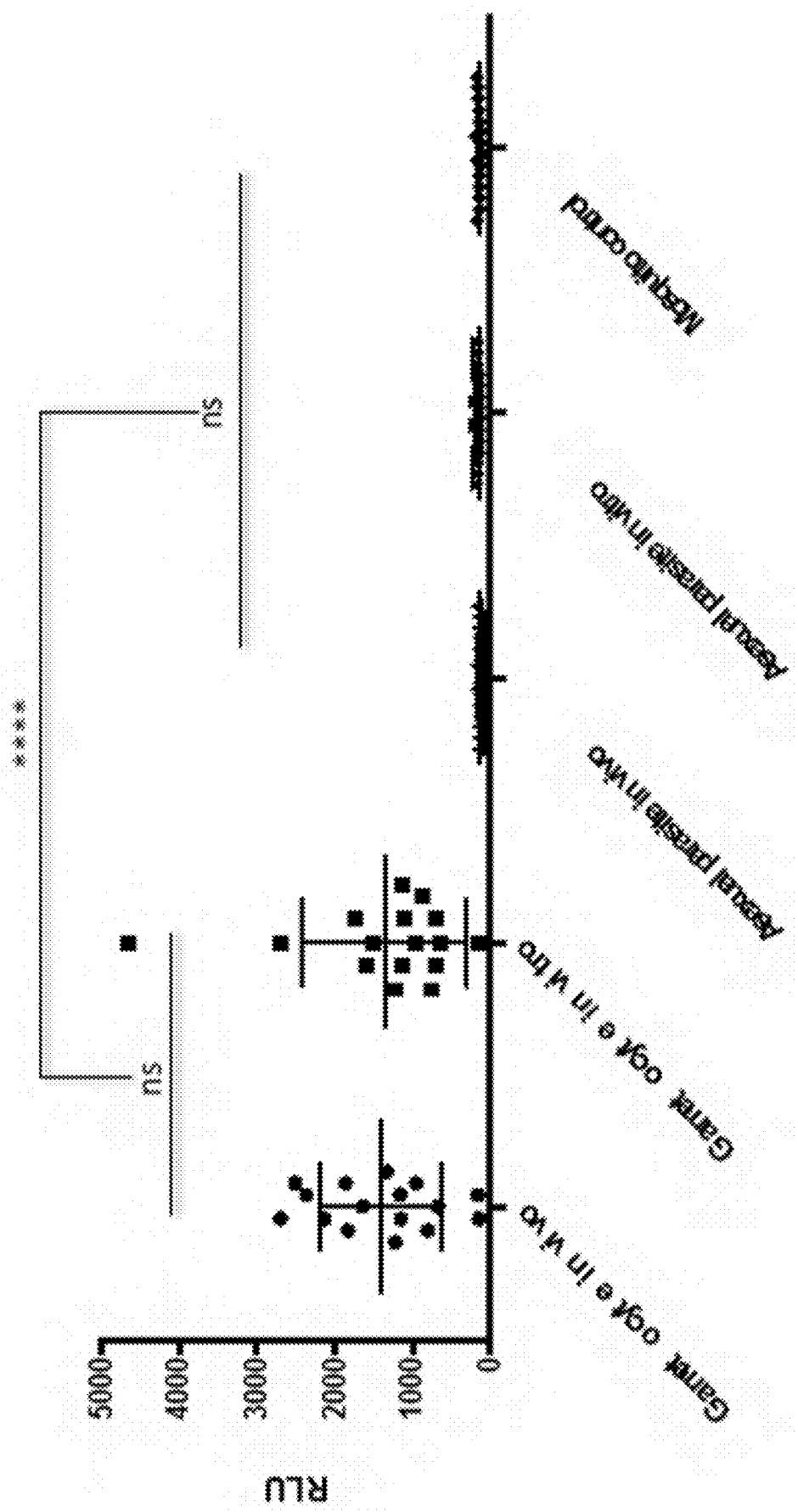
FIG. 7 shows the mosquito luciferase assay on day 8 post infection by gametocytes cultured in vivo and in vitro. RLU of mosquitoes (n=5) luciferase activity on day 8 post infection by gametocytes cultured in vivo and in vitro from five independent experiments each with 32 replicate samples. Statistical differences were determined by Kruskal-Wallis and Dunn's multiple comparison tests. The graph is shown as mean±SD.

Example 3—Mosquito Luciferase Assay on Day 8 Post Infection by PfKF7G4 Gametocytes Cultured In Vivo and In Vitro and the Strategy for Oocyst Inhibition In Vivo/In Vitro Based on PfKF7G4 Luciferase Assay To confirm the luciferase assay that can monitor the activation of oocyst development in mosquito stage and test if there is residual luciferase signal in day-8 mosquitoes coming from asexual parasites or gametocytes which were not developed into oocysts, we carried out mosquito luciferase assay on day 8 post infection by gametocytes cultured in vivo and in vitro comparing asexual parasite culture in vivo, in vitro and mosquitoes which only took human RBC in blood meal as mosquito control. The luciferase activity of five independent experiments was measured by combining 5 mosquitoes as one sample, 32 replicate samples for each independent experiment. The luciferase signal obtained from day-8 mosquitoes was showed as RLU of mean±SD (n=32) (FIG. 7). Statistical differences were determined by Kruskal-Wallis and Dunn's multiple comparison tests. Asexual group RLU in vivo and in vitro were $154.0\pm19.84$ and $153.4\pm20.96$ respectively, didn't show significant difference ($P>0.9999$) comparing with mosquito control group RLU $152.8\pm19.35$ while gametocyte group RLU in vivo and in vitro were $1420\pm779.7$ and $1358\pm1051$ respectively which showed extremely significant difference comparing with asexual groups and mosquito control group. The experimental results demonstrate that luciferase assay can be used to evaluate PfKF7G4 oocyst development in mosquito stage and there is no residual luciferase signal from asexual parasite to disturb the luciferase assay value from mosquitos on day 8 post infection.

Figure 8:
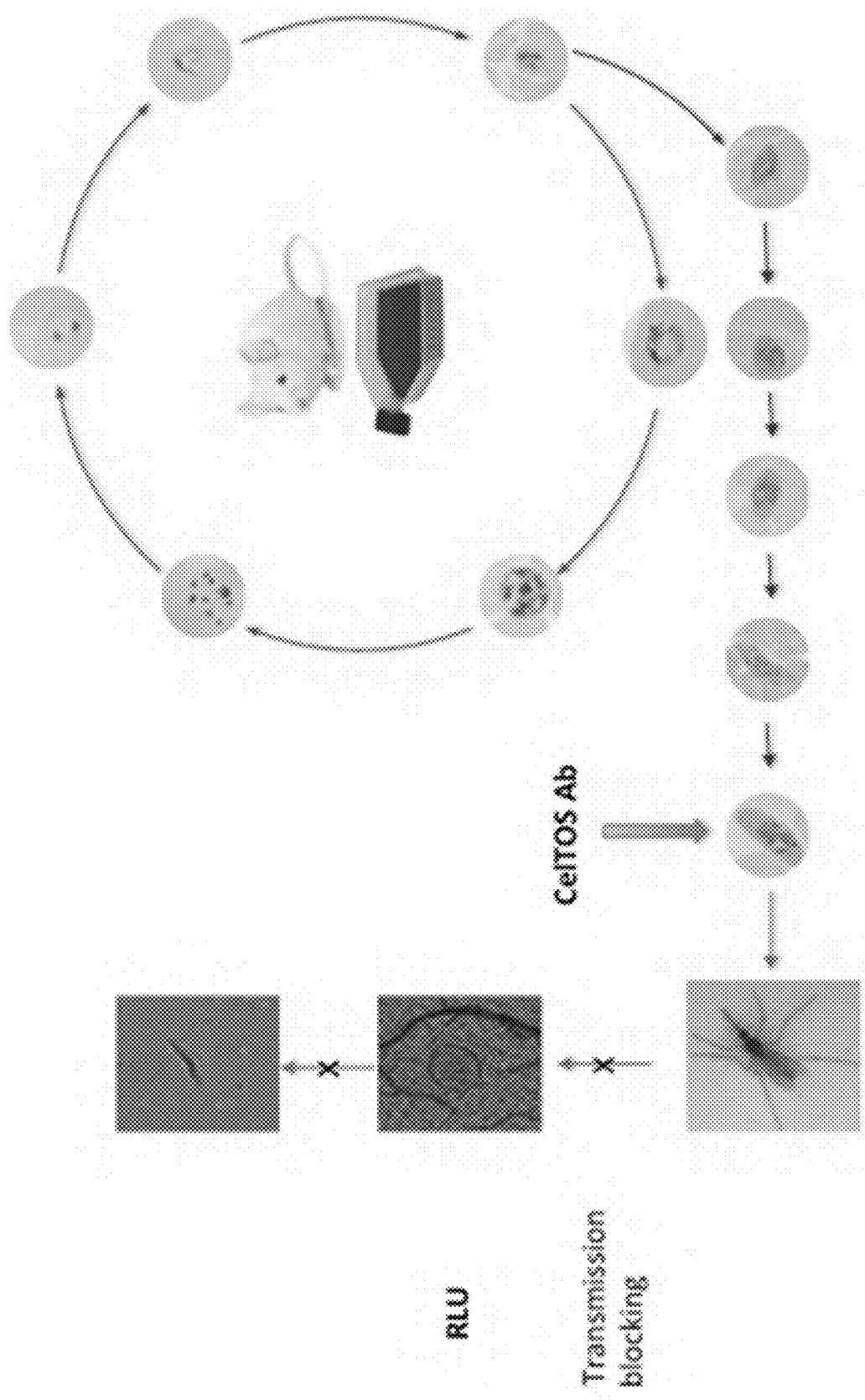
FIG. 8 shows the strategy for oocyst inhibition in vivo/in vitro based on PfKF7G4 luciferase assay. Luciferase reporter clone PfKF7G4 parasites are cultured in vivo and in vitro to formed mature infective gametocytes. Gametocytes cultured in vitro are mixed with fresh human blood and CelTOS antibody to be fed laboratory reared *A. stephensi* mosquitoes by SMFA while gametocytes cultured in vivo of huRBC-NSG mice are mixed with CelTOS antibody by intravenously injection to be fed mosquito directly. Both CelTOS antibody inhibiting ability in vivo and in vitro for parasites transmission and developing in mosquito stage can be assessed on luciferase activity of infected mosquitoes on day 8 post infection.

Luciferase transgenic *P. falciparum* parasite clone-PfKF7G4 is not only able to form mature gametocyte in vitro but also can cause successive cycles of infection in huRBC-NSG mice to form infective gametocytes in vivo. Experimental results showed both these kinds of gametocytes cultured in vivo and in vitro developed oocysts and sporozoites with luciferase activity in mosquito stage. Luciferase signal from oocyst is strong enough to be detected for even only one oocyst in the early stage of its development and there is no residual luciferase signal from asexual parasite to disturb the luciferase assay value from mosquitos on day 8 post infection. Gametocytes cultured in vitro can be mixed with test CelTOS antibody in mosquito feeding blood meal by SMFA and gametocytes cultured in huRBC-NSG mice can mixed with test CelTOS antibody by intravenously injection in vivo and feed mosquito directly by direct feeding assay (DFA). The method of measuring mosquito luciferase activity in 96-well plate is simpler, more sensitive and accurate than counting oocysts by dissecting mosquito. All these experimental results make it feasible to establish antibody mediated *P. falciparum* oocyst inhibition by using luciferase transgenic parasite PfKF7G4 in vitro and in vivo (FIG. 8).

Example 4—CelTOS Antibody-Mediated Oocyst Inhibition Assay In Vivo and In Vitro

Figure 9A:
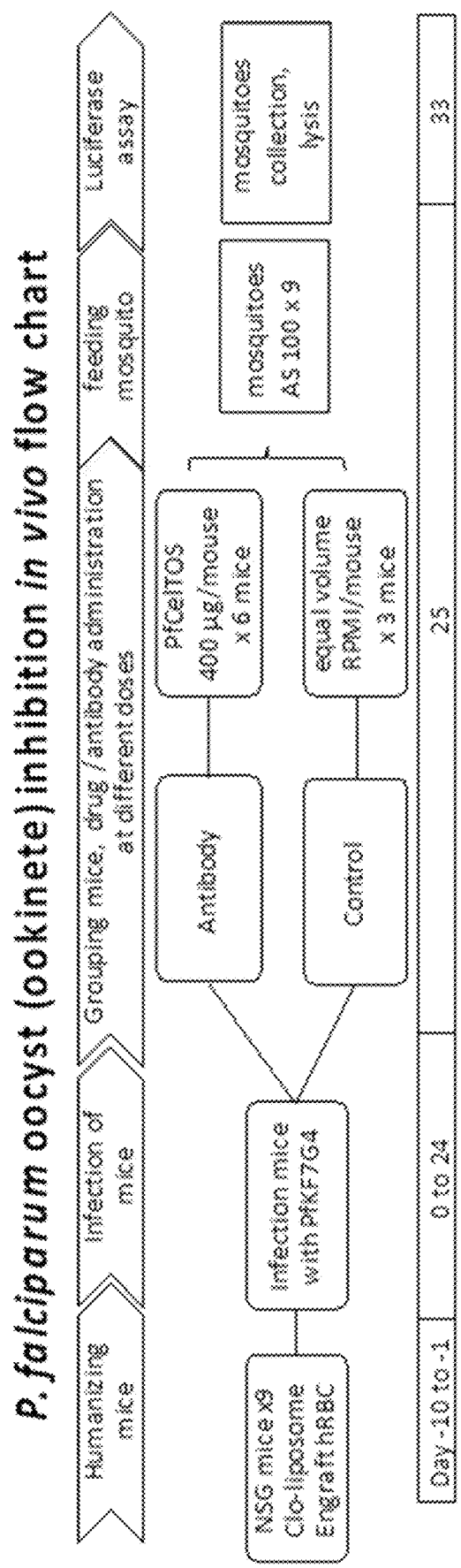
FIG. 9A and FIG. 9B show an experiment of antibody-mediated oocyst inhibition in vivo.
Figure 9B:
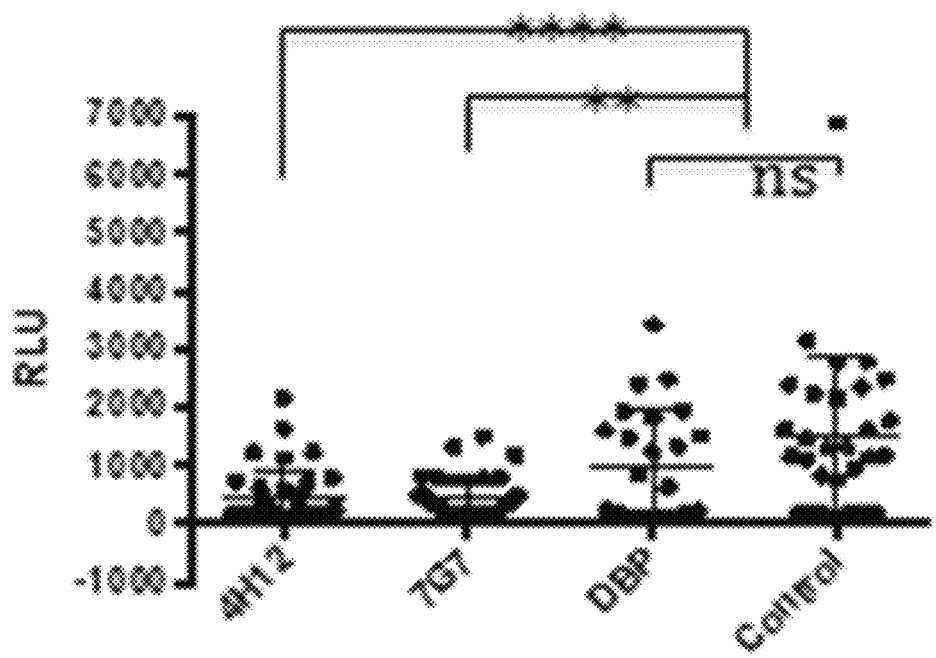

Starting with the engraftment of NSG mice with huRBC and treating the mice with clodronate lipsome 10 days before infection with *P. falciparum* PfKF7G4 parasites, CelTOS antibody-mediated oocyst inhibition assay in vivo including humanized mice preparation, mice infection by mouse-adapted parasite PfKF7G4 and gametocyte culture in vivo, antibody inhibition administration, mosquitoes feeding and mosquito-stage luciferase detection five continuous successive steps (FIG. 9A. After 4 cycles of huRBC engraftment in conjunction with clodronate liposome treatment, mice with huRBC level >32% were chosen for inhibition assay. Selected each mouse was infected with 25 µl huRBCs parasitized by mouse adapted PfKF7G4 at a mixed stage of 5% parasitemia. Continually cycled the infected mice with regular amount huRBC 150 ul/ea and clodronate liposome 100 ug/ea 11 days. Mouse infection was checked by Giemsa staining of thin blood films drawn from the tail vein. If parasitemia >5% and gametocytemia >0.1%, decreased the huRBC amount to 100 ul mixed with 100 ul AB human serum in the mouse cycling of humanization until the end of experiment. On day 22 post infection, gametocytaemia was checked by Giemsa staining of thin blood films drawn from the tail vein. Choose infected mice with stage V gametocytaemia between 0.07-0.18% to use for next experiments. Randomly grouping infected mice into 4 groups as *P. falciparum* CelTOS mAb 4H12 group, *P. vivax* CelTOS mAb 7G7 group, *P. vivax* DBP mAb 3A4 antibody control group and blank control group, 3 mice each group. 1 hour before feeding mosquitoes, antibody group mice were i.v. injected with antibody 400 ug in 200 ul RPMI each 25 g mouse (16 mg/kg dose), control group mice were i.v. injected with 200 ul RPMI/mouse. Post treatment of antibody and RPMI i.v. injection, mice were placed back in cage moving freely for 1 h, after which, mice were anesthetized and pots of 100 starved *A. stephensi* mosquitoes were allowed to feed on each infected mouse for 25 minutes by DFA. Euthanized mice with $CO_2$ after feeding mosquitoes. CelTOS mAb inhibitory activity was detected and analyzed by comparing CelTOS groups with control groups using luciferase assay on day 8 after mosquito feeding by pooling 5 mosquitoes to one sample. Statistical differences were determined for four independent experiments each with 60 replicates for group 4H12, 54 replicates for group 7G7, 24 replicates for group DBP and 54 replicates for group control by Kruskal-Wallis and Dunn's multiple comparison test. The graph was shown as means±SD of four separate experiments. Data analysis showed that the RLU values for group 4H12 with 442.5±486.2 (** $P<0.0001$) and 7G7 with 474.5±372.8 ( $P<0.01$) were significantly lower than those for DBP (1019±962.6) and control (1492±1374) groups. Mosquito luciferase assay on day 8 post infection demonstrated PfCelTOS mAb 4H12 and PvCelTOS mAb 7G7 were able to inhibit oocyst developing in mosquito from gametocytes cultured in vivo (FIG. 9B).

Figure 10:
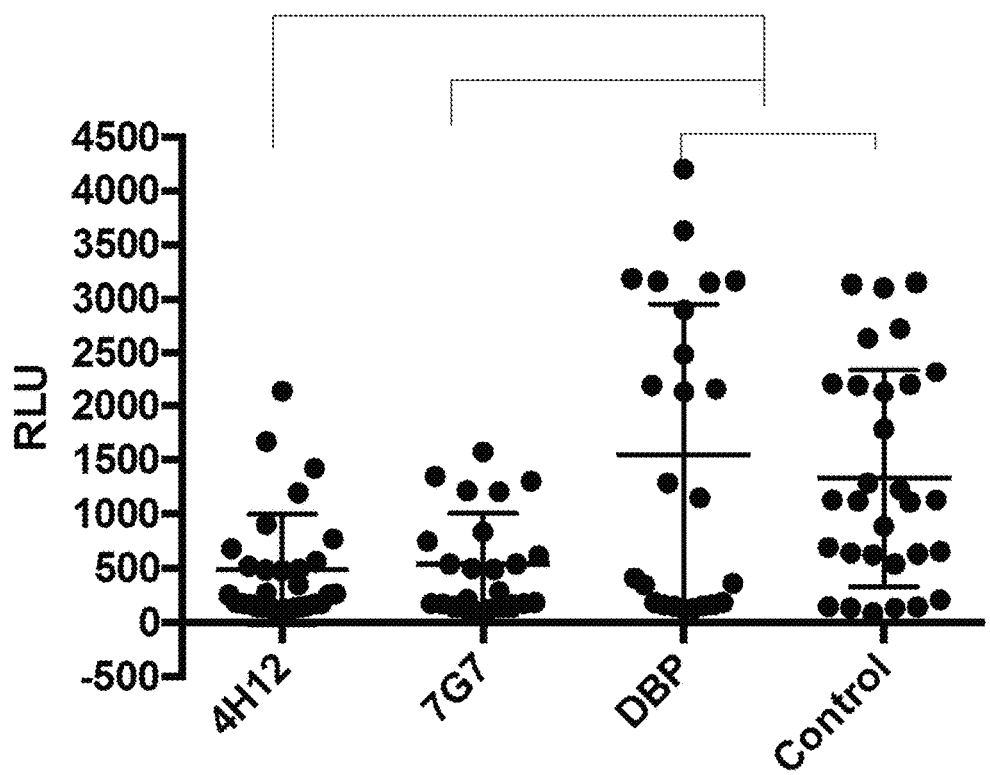
FIG. 10 shows an experiment of antibody-mediated *P. falciparum* oocyst inhibition in vitro. To confirm the results of CelTOS mAb inhibiting *P. falciparum* oocysts development from gametocytes in vivo, to mimic the experimental condition in vivo, we also set up four independent experiments for CelTOS mAb 4H12, 7G7 and antibody control DBP 3A4, negative blank control for gametocytes cultured in vitro. 400 pg mAb was added to gametocyte culture in 1 ml blood meal for 100 mosquitoes respectively 30 minutes prior to the mosquito feeding for SMFA. Mosquito RLU was measured by luciferase assay on day 8 post infection. RLU values are means±SD in graph. Compared with control groups PfCelTOS mAb 4H12 and PvCelTOS mAb 7G7 significantly inhibited oocyst developing in mosquito from gametocytes cultured in vitro.
Figure 11A:
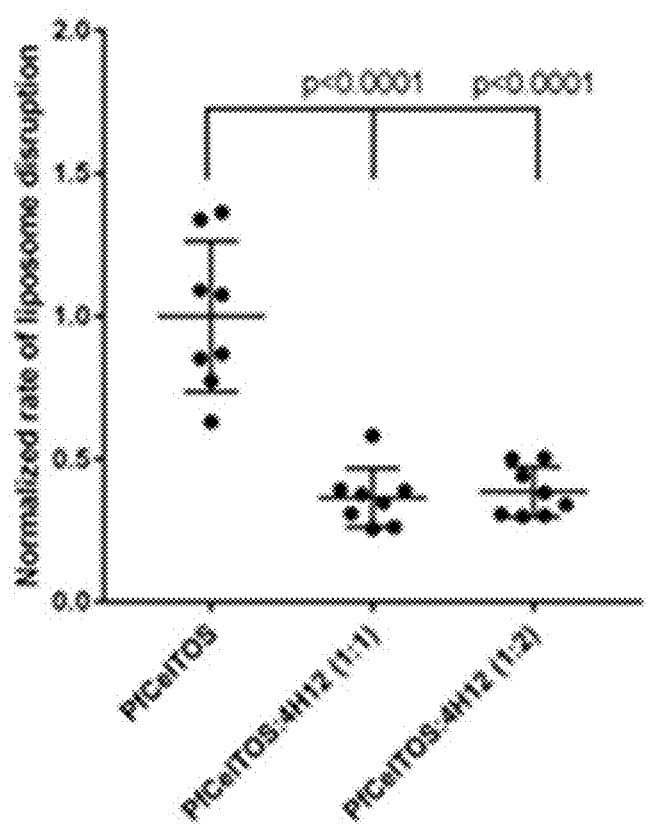
FIG. 11A, and FIG. 11B show the inhibition of CelTOS-mediated membrane disruption by antibodies. Two monoclonal antibodies: Pf4H12 and Pv7G7 were tested for their ability to inhibit CelTOS. The normalized rate of liposome disruption after treatment with CelTOS alone (set at 100%), or following treatments with CelTOS and increasing amounts of antibodies. The graphs show results from eight technical replicates shown as mean±s.e.m.
Figure 11B:
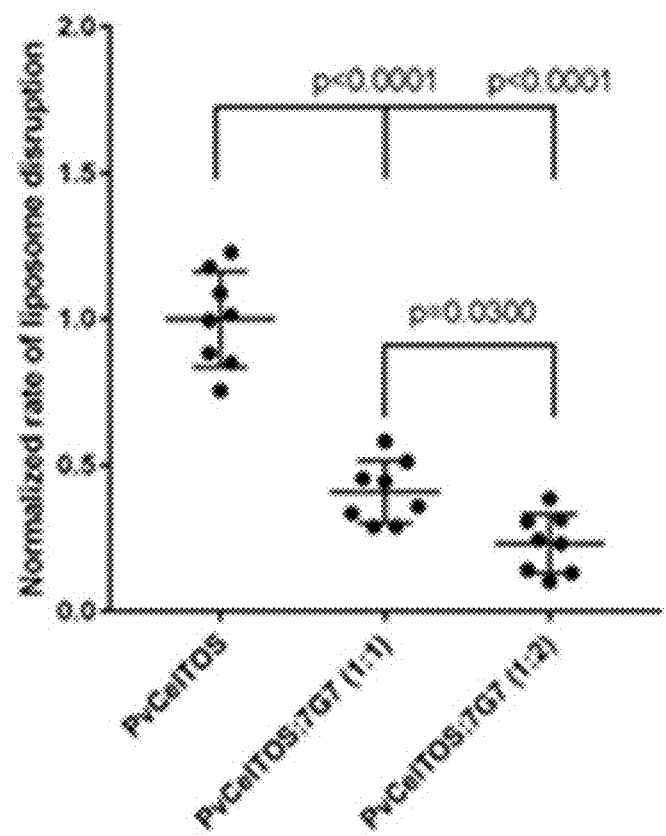
Figure 12A:
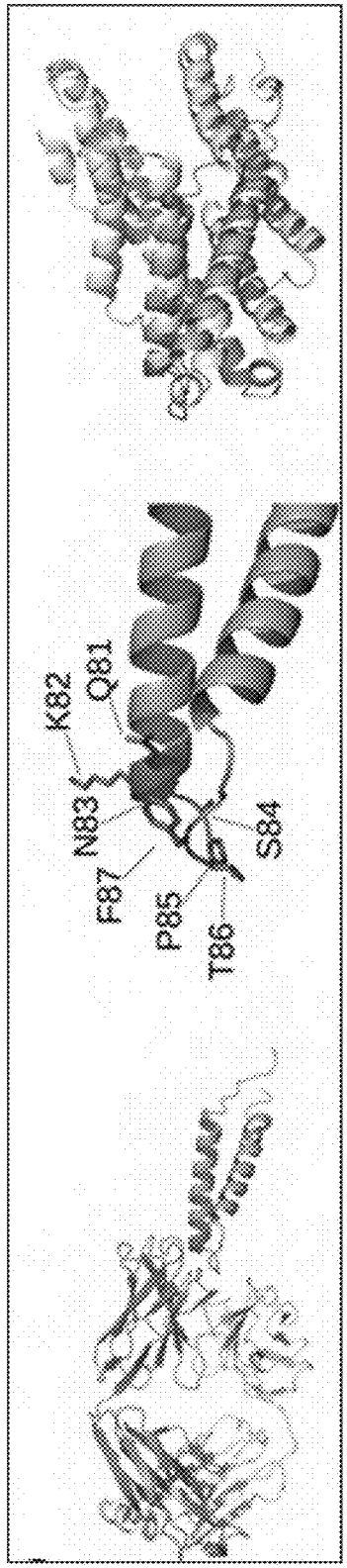
FIG. 12A, FIG. 12B and FIG. 12C show the crystal structures of the PfCelTOS/Pf4H12 Fab, PvCelTOS/Pv7G7 and PvCelTOS/Pv6C4 Fab complexes reveal neutralizing epitopes in CelTOS.
Figure 12B:
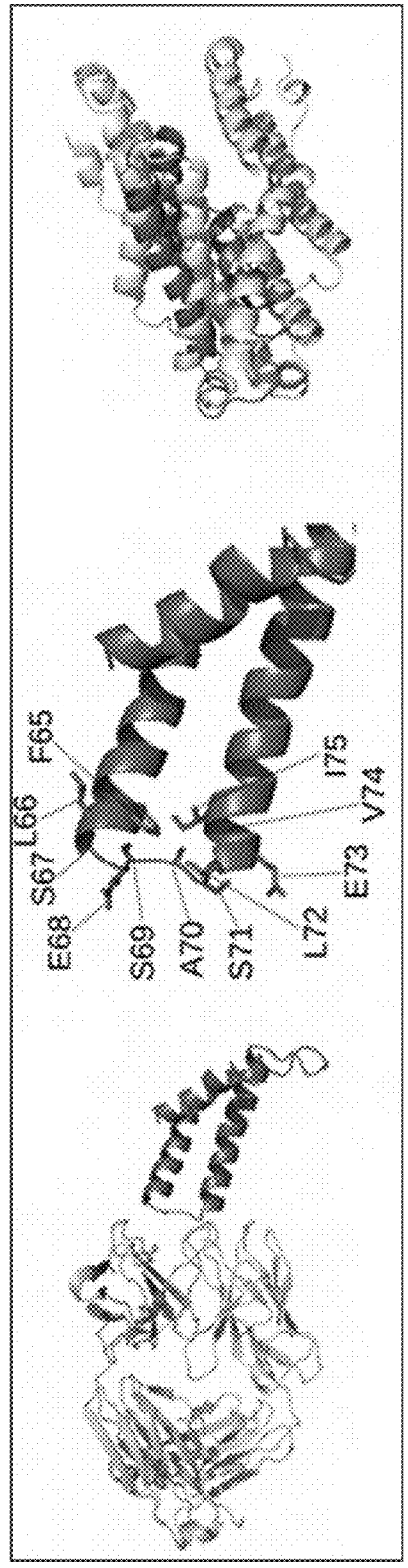
Figure 12C:
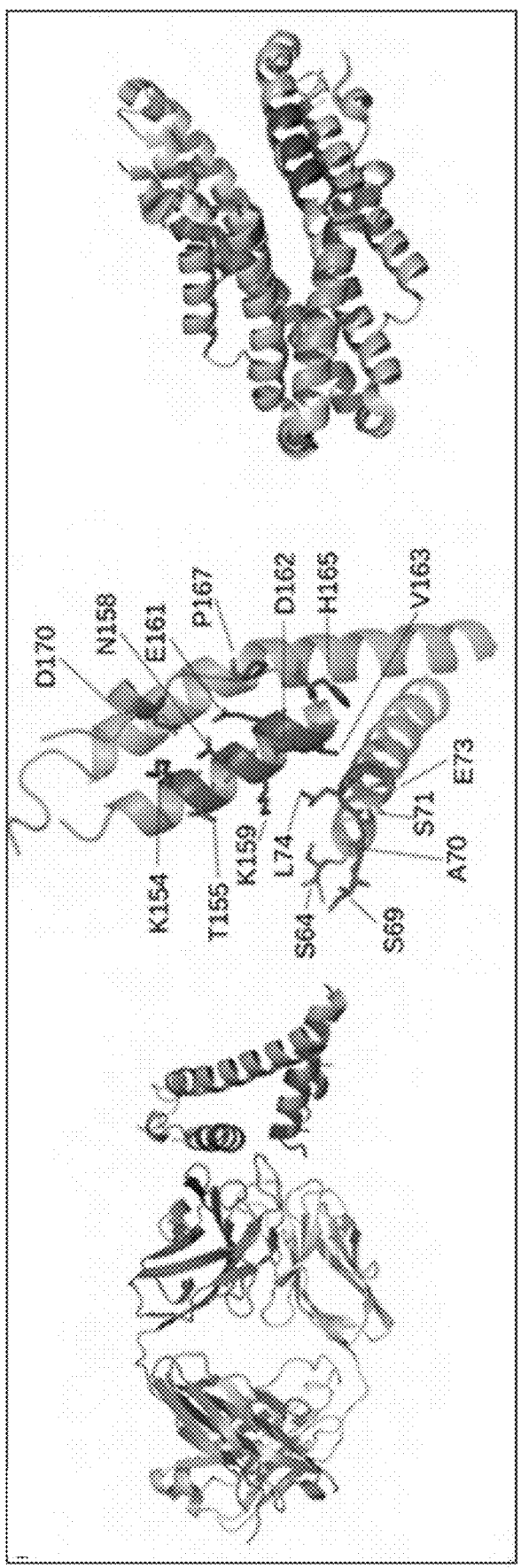

To further confirm the PfCelTOS mAb 4H12 and PvCelTOS mAb 7G7 functional inhibition for *P. falciparum* oocyst developing, CelTOS antibody-mediated oocyst inhibition experiment in vitro was carried out. Starting with asexual culture, PfKF7G4 was maintained according to the method stated in *P. falciparum* KF7 parasite culture above without antibiotics. Parasites were synchronized using two consecutive 16-hours apart 5% sorbitol treatments for generating 16-24 hours old parasites when the time point was confirmed by light microscopy. Continually cultured the parasites to 4-6% parasitemia at trophozoite stage, induced the parasites to form gametocytes by mFA media (containing 0.0039% fatty acid free BSA and 30 uM of palmitic acid/oleic acid) for 24 hours. Exchanged media daily by adding GlcNAc to a final concentration of 50 mM up to day 4 of gametocyte development. Checked gametocyte stages and exflagellations between days 14-17 of gametocyte cultures. Prepared feeding mosquitoes when stage V gametocytes were prevalent. Blood meal was prepared with 0.3% stage V gametocytemia in fresh human blood containing 50% human serum. CelTOS antibody and DBP control antibody blood meal contains 400 ug antibody/ml, control blood meal was added same volume PBS instead, incubate 30 minutes at 37° C., mixed 1 time at 15th minute. Using a temperature-controlled Hemotek membrane-feeding device (Discovery Workshops) to feed 100 starved 8 h 4 day-old female *A. stephensi* mosquitoes/ml blood meal by SMFA. In order to mimic the in vivo conditions, mosquito luciferase assay analysis as in vivo was accomplished on day 8 post mosquitoes feeding by pooling 5 mosquitoes to one sample. Four independent experiments samples were measured included 54 replicates for group 4H12, 24 replicates for group 7G7, 24 replicates for group DBP and 54 replicates for group control (FIG. 10). The graph was shown as RLU means±SD of four separate experiments. Mosquito RLU values of group 4H12, 7G7, DBP and control were found to be 488.2±507.8, 538.5±466.8, 1550±1408 and 1336±1005 respectively. Data analysis by Kruskal-Wallis and Dunn's multiple comparison test showed that the RLU values for 4H12 (** $P<0.01$) and 7G7 (* $P<0.05$) groups are significantly lower than those for DBP and control groups. Thus, the in vivo results on PfCelTOS mAb 4H12 and PvCelTOS mAb 7G7 inhibiting function for *P. falciparum* oocyst developing by mosquito luciferase assay was further validated with the in vitro experiments.

Figure 13A:
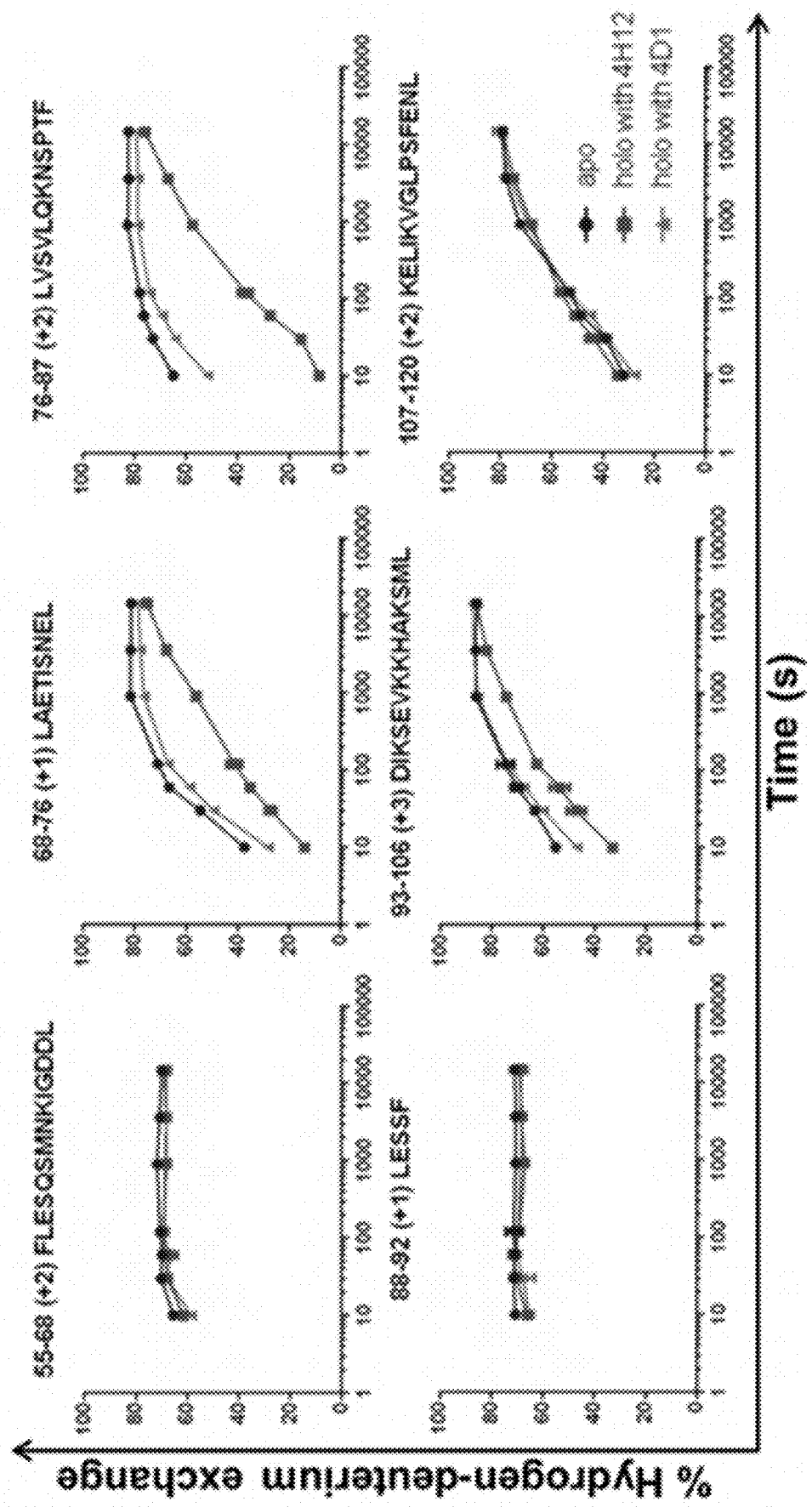
FIG. 13A, FIG. 13B and FIG. 13C depict the identification of epitopes in PfCelTOS by Hydrogen-deuterium exchange mass spectrometry.
Figure 13B:
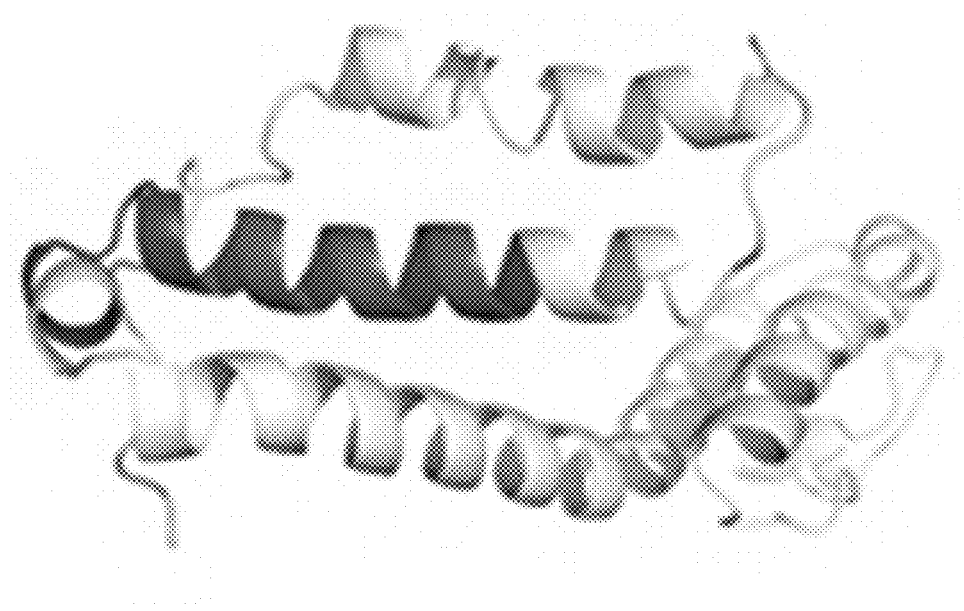
Figure 13C:
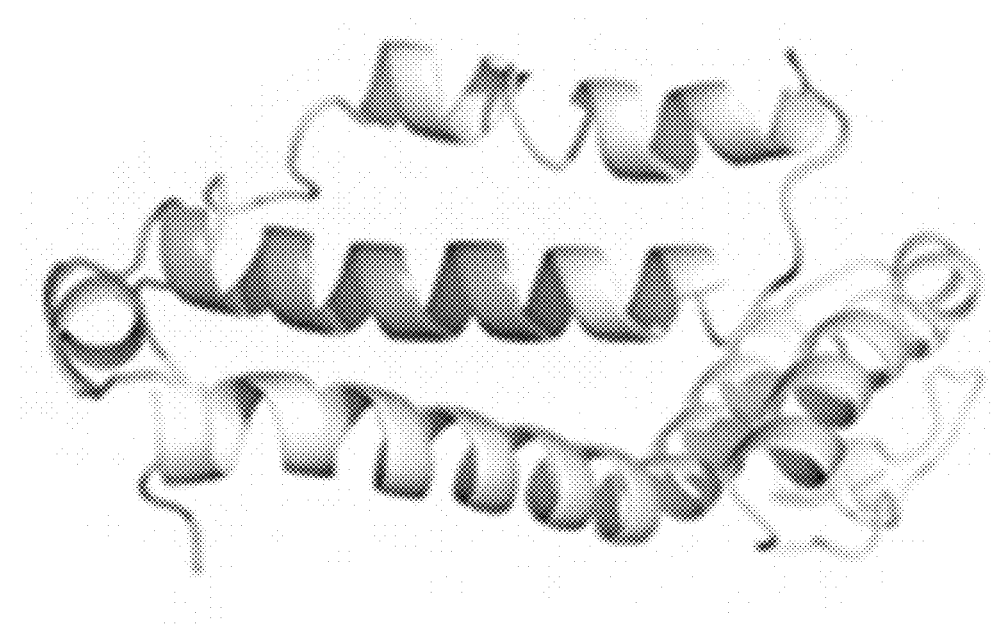
Figure 14A:
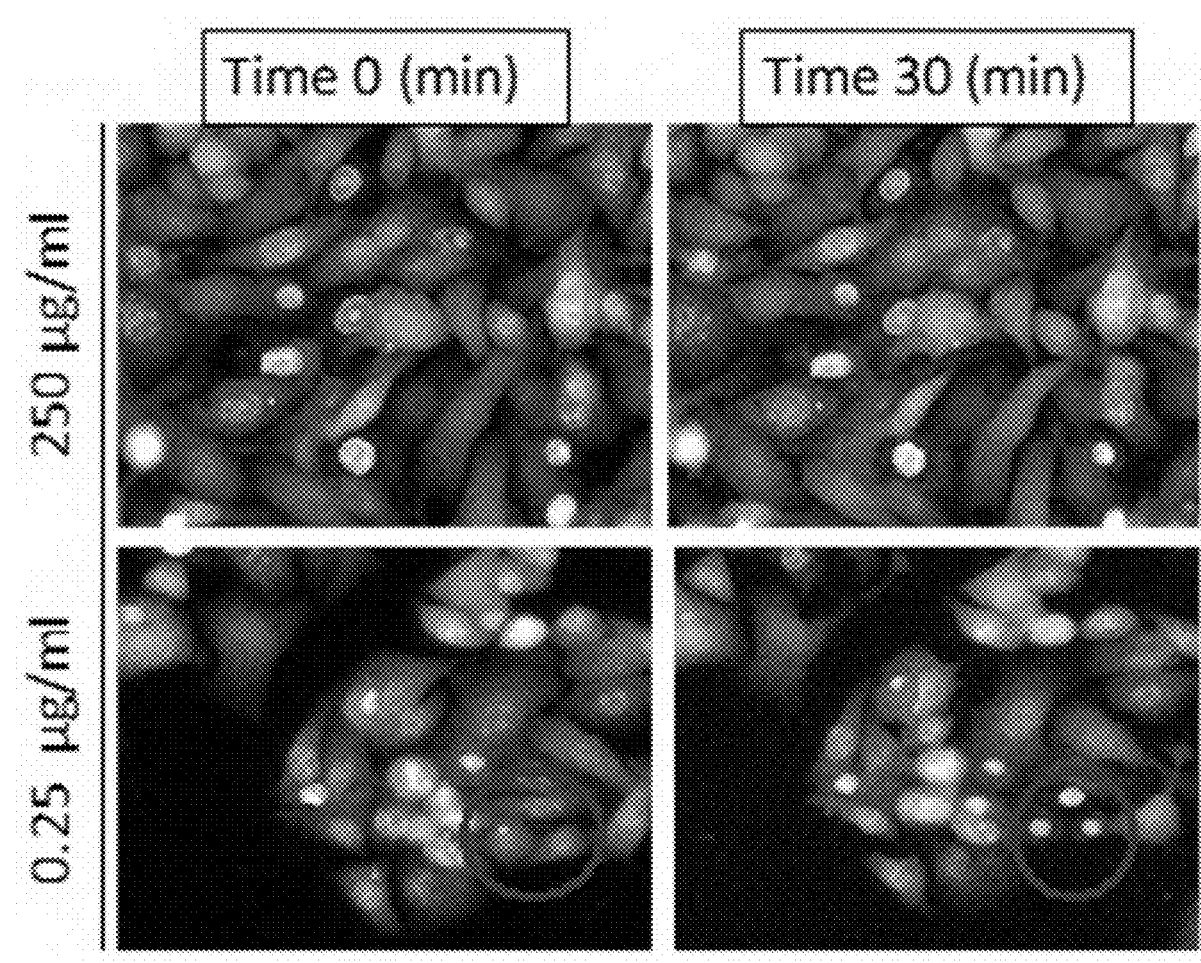
FIG. 14A, FIG. 14B, and FIG. 14C show increased concentrations of Ab 7G7 exhibited increased levels of inhibition of sporozoite cell traversal and infection of PHH until complete functional inhibition of sporozoites was achieved.
Figure 14B:
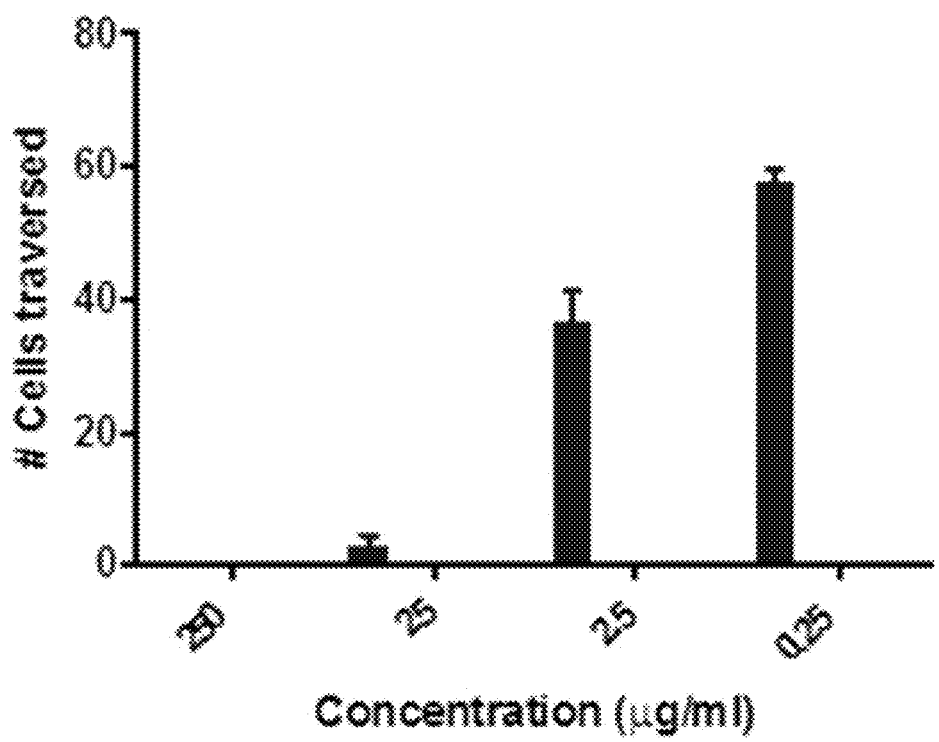
Figure 14C:
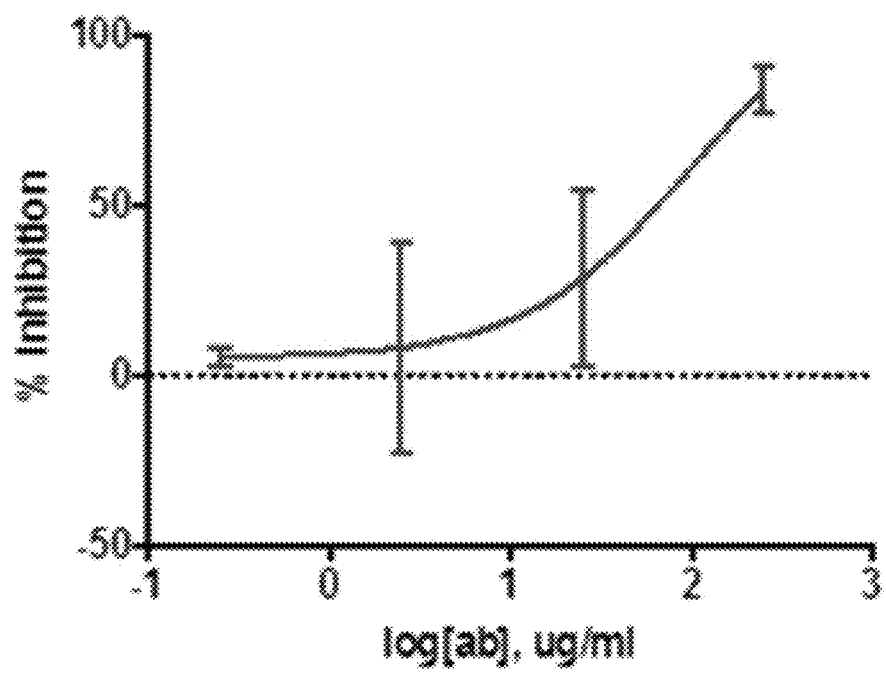
Figure 15:
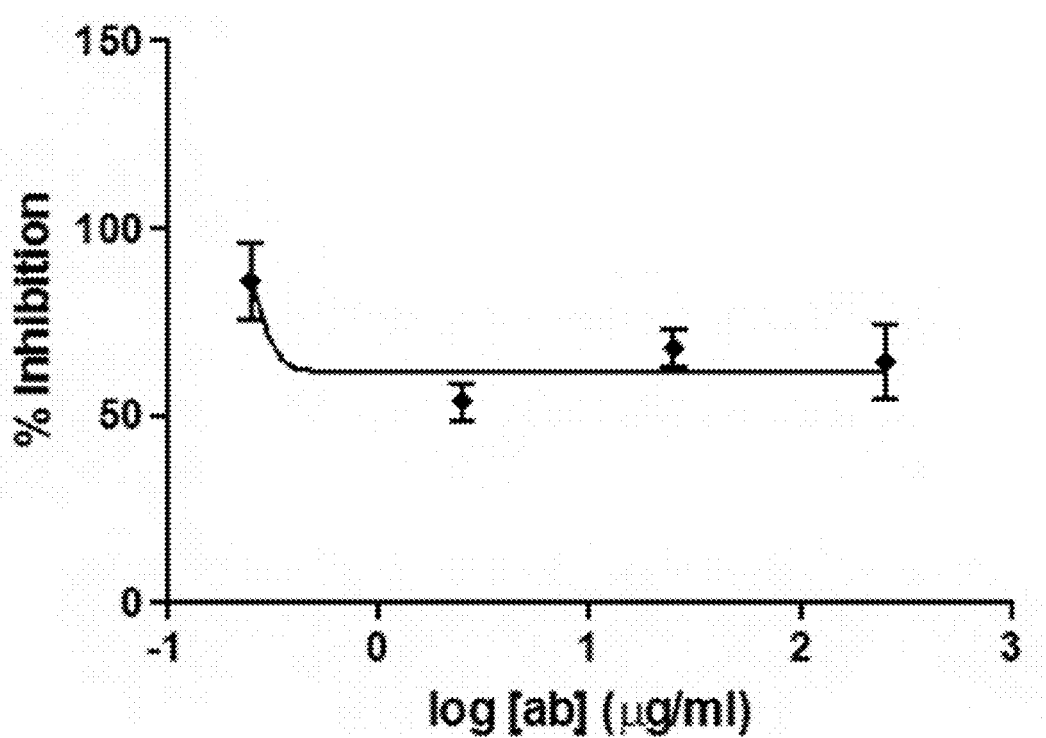
FIG. 15 shows all concentrations of AB 4H12 show inhibition (50-80%) of sporozoite PHH invasion.
Figure 16A:
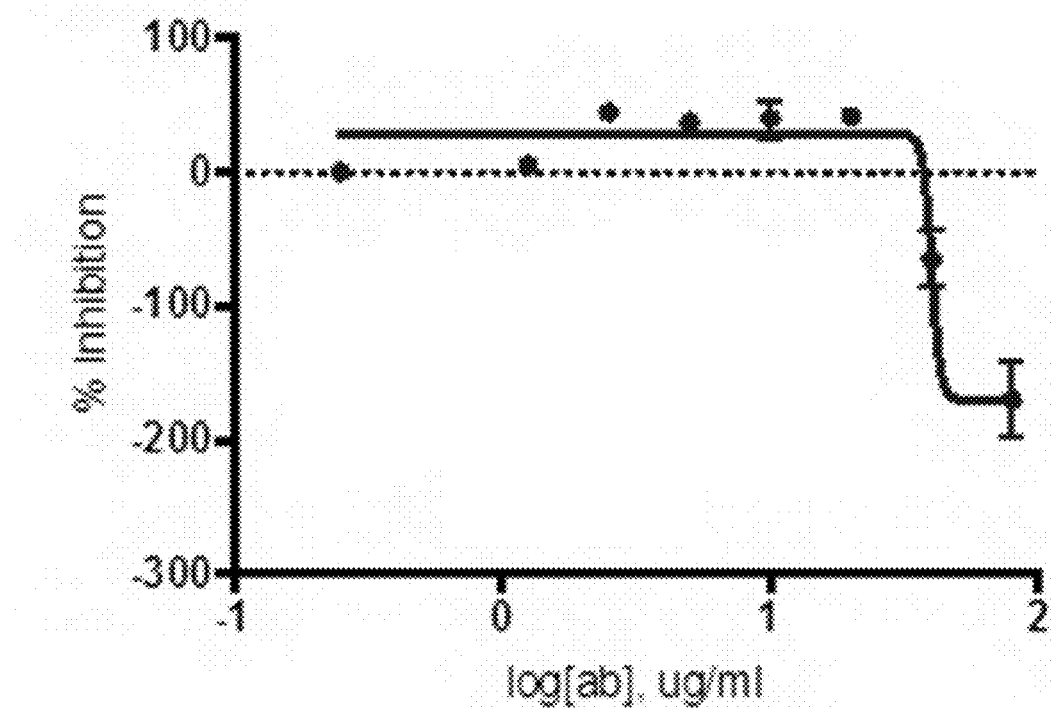
FIG. 16A, FIG. 16B, FIG. 16C, FIG. 16D and FIG. 16E show anti-4D1 celTOS cell traversal and PHH invasion.
Figure 16B:
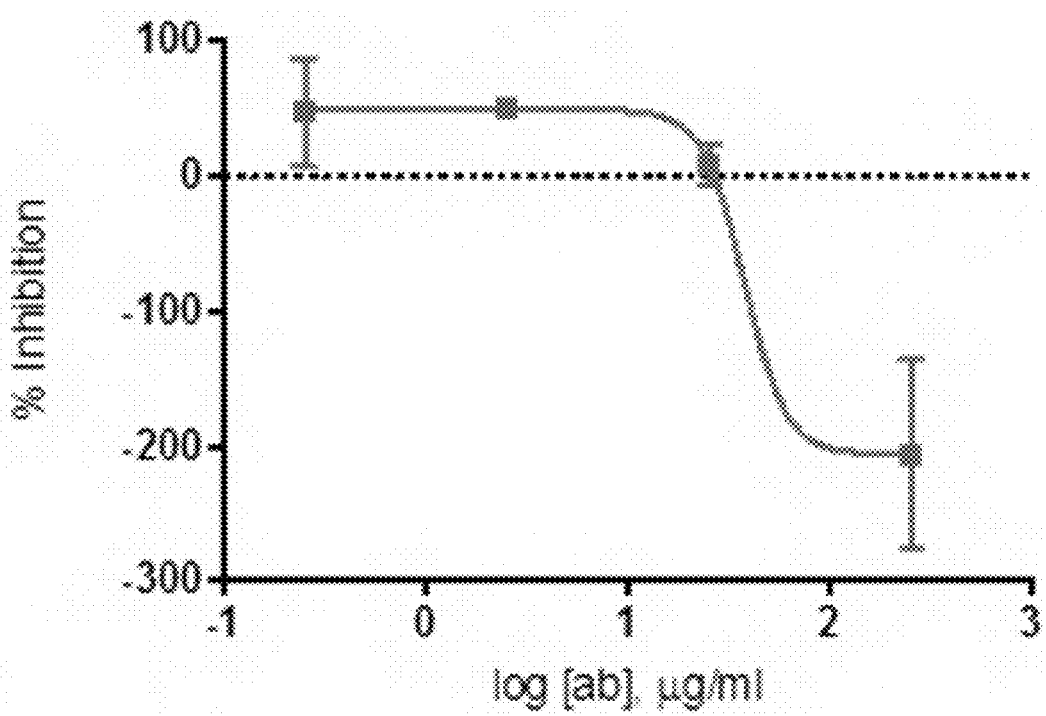
Figure 16C:
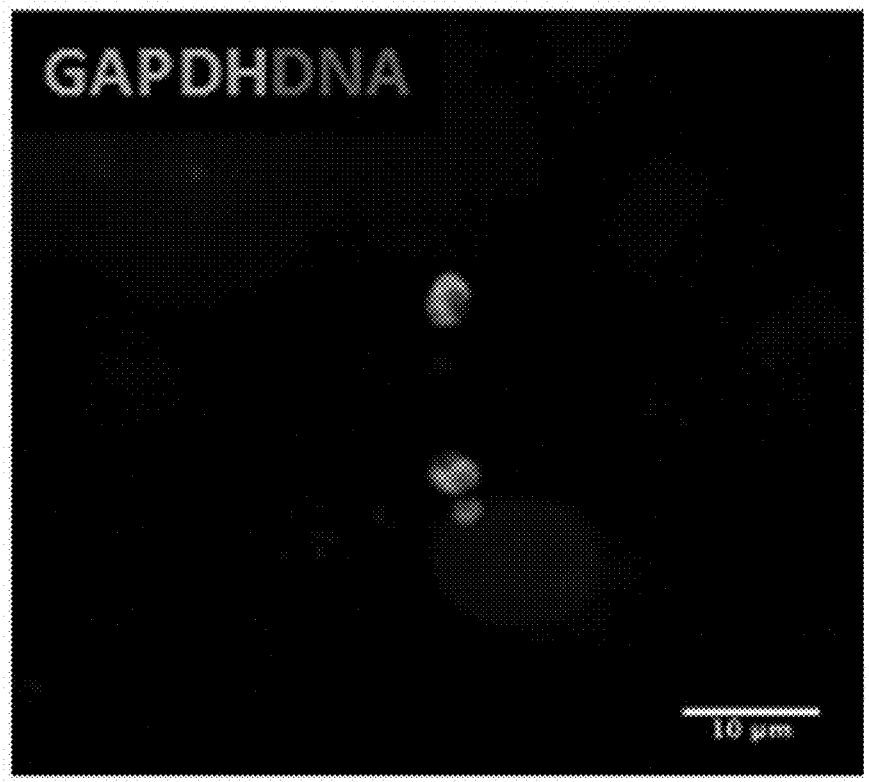
Figure 16D:
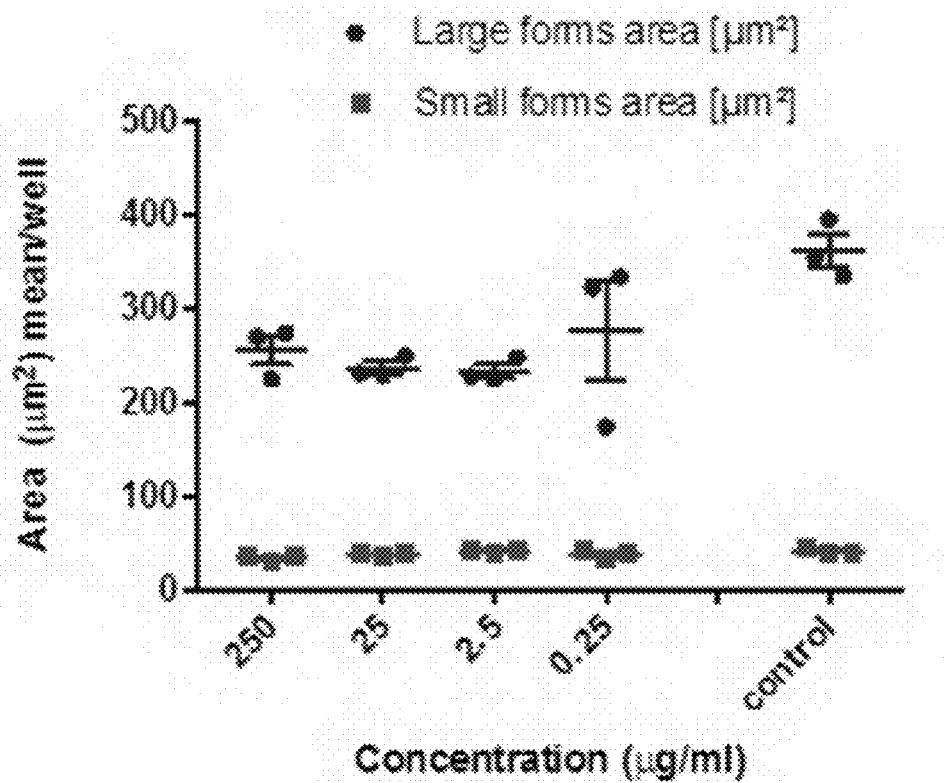
Figure 16E:
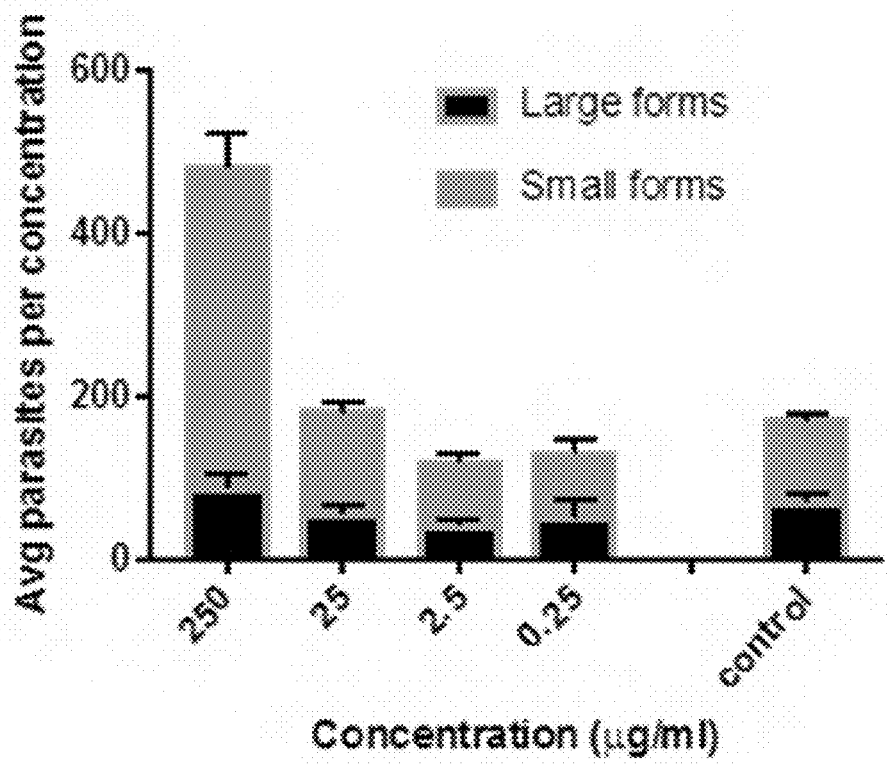

Example 5—Identification of Monoclonal Antibodies that Inhibit CelTOS-Mediated Membrane Disruption and Neutralizing Epitopes in CelTOS from the Crystal Structures of PfCelTOS/Pf4H12 Fab and PvCelTOS/Pv7G7 Fab Complexes We investigated the ability of the monoclonal antibodies Pf4H12, and Pv7G7 to inhibit CelTOS-mediated disruption of liposomes containing phosphatidic acid (PA liposomes). CelTOS was mixed with antibodies at molar ratios of 1:0.5, 1:1 and 1:2, incubated for one hour, and each mixture applied to PA liposomes. As expected, CelTOS alone disrupted membranes. Pf4H12 and Pv7G7 inhibited PfCelTOS- and PvCelTOS-mediated disruption of PA liposomes respectively (FIG. 11A and FIG. 11B).

Given that Pf4H12 and Pv7G7 antibodies inhibit PfCelTOS and PvCelTOS respectively we pursued the crystal structures of the antibody Fab fragment in complex with antigen. Crystal structures of these complexes will reveal the amino acid sequence of the epitope targeted by an antibody as well as how the epitope is presented in three dimensional space and recognized by the neutralizing antibody. We determined the crystal structures of the PfCelTOS/Pf4H12 Fab, PvCelTOS/Pv7G7 Fab and, PvCelTOS/Pv6C4 Fab complexes (FIG. 12, Table 3). These structures revealed neutralizing epitopes in CelTOS. Specifically, Pf4H12 targets the region on PfCelTOS between residues 81 and 87, while 7G7 targets the region on PvCelTOS between residues 65 and 75, while 6C4 targets region on PvCelTOS between residues 64-74, 154-159, and 161-170. Interestingly, the crystal structures show the complete structure of the antibody Fab fragment but only part of the antigen (FIG. 13). This was because we only observed electron density around the regions of PfCelTOS and PvCelTOS bound by the antibody. The missing electron density could be due to flexibility or disorder, suggesting that binding of neutralizing antibody results in vast changes in the structure of CelTOS compared to the structure previously reported for PvCelTOS (16).

Example 6—Identification of Neutralizing and Non-Neutralizing Epitopes in PfCelTOS by Hydrogen-Deuterium Exchange Mass Spectrometry Hydrogen deuterium exchange mass spectrometry (HDX-MS) was used in parallel with X-ray crystallography to determine epitopes in PfCelTOS (FIG. 13). In HDX-MS experiments it is expected that binding of antibodies to PfCelTOS will result in increased protection of the binding sites. HDX-MS confirmed the epitope in PfCelTOS targeted by Pf4H12 that had been identified from the crystal structures of PfCelTOS/Pf4H12 Fab complex. Incubation of PfCelTOS with Pf4H12 resulted in the protection of residues 68-87 in PfCelTOS, which is encompasses residues 81-87 mapped from the crystal structures (FIG. 13A and FIG. 13B top panel). Incubation of PfCelTOS with Pf4D1 showed some minimal reduction in exchange between regions 68-87 (FIG. 13B bottom panel, putative epitope shown in salmon).

are fundamental for oocyst inhibition experiments of *P. falciparum* transmission blocking study.

Immunodeficient NSG mouse (NOD.Cg-Prkdcscid Il2rgtm1Sug/JicTac) lacks functional B and T lymphocytes, doesn't retain residual NK cell function, is able to maintain high levels of engrafted huRBC by the injection of liposomal-clodronate formulations to deplete murine phagocytic

TABLE 3

Data collection, phasing and refinement statistics

|  | PfCelTOS/Pf4H12 complex | PvCelTOS/Pv7G7 complex | PvCelTOS/Pv6C4 complex |
| --- | --- | --- | --- |
| Data collection |  |  |  |
| Space group | P1 | C 1 2 1 | C 1 2 1 |
| Cell dimensions |  |  |  |
| a, b, c (Å) | 59.69, 59.73, 153.45 | 171.00, 89.00, 199.00 | 166.45 104.64 51.43 |
| α, β, γ (°) | 82.07, 82.20, 72.27 | 90, 105, 90 | 90 89.485 90 |
| Resolution (Å) | 56.6-2.7 (2.85-2.69) | 58.79-2.99 (3.45-2.99) | 19.65-2.5 (2.589-2.5) |
| $R_{sym}$ (%) | 9.4 (26.9) | 5.8 (73.7) |  |
| I/σI | 4.66 (1.43) | 22.23 (2.52) | 10.95 (1.06) |
| Completeness (%) | 98.0 (84.4) | 99.3 (99.7) | 99.67 (99.93) |
| Redundancy | 1.06 (1.085) | 3.7 (3.8) | 7.3 (6.5) |
| Refinement |  |  |  |
| Resolution (Å) | 56.6-2.7 | 58.79-3.15 | 19.65-2.5 |
| No. reflections | 53,301 | 50913 | 221903 |
| $R_{work}/R_{free}$ | 26.44/32.86 | 28.76/35.32 | 24.5/28.7 |
| No. atoms |  |  |  |
| Protein | 14,146 | 15232 | 4065 |
| Ligand/ion | 0 | 0 | 0 |
| Water | 215 | 0 | 189 |
| B-factors |  |  |  |
| Protein | 43.4 | 4 | 66.01 |
| Ligand/ion | N/A | N/A | N/A |
| Water | 31.5 | N/A | 57.94 |
| R.m.s. deviations |  |  |  |
| Bond lengths (Å) | 0.011 | 0.012 | 0.002 |
| Bond angles (°) | 1.53 | 1.593 | 0.52 |

Each data set was collected from a single crystal. Highest resolution shell is shown in parenthesis.

Discussion of Examples 1-6

To identify CelTOS antibodies that neutralize malaria parasites we focused on targeting malaria transmission. We chose to first examine the ability of CelTOS antibodies in neutralizing malaria transmission because a transmission blocking vaccine would be invaluable for malaria control and novel model systems for studying malaria transmission are needed. Also, since CelTOS has conserved role in mammalian and mosquito cells (15, 16), we expect that CelTOS antibodies that neutralize malaria parasites during the transmission stage will also inhibit the host stage. Towards a model for malaria transmission, we note that the luciferase expressing transgenic *P. falciparum* 3D7 parasite doesn't show as high rate of gametocyte production as the parental NF54 strain in gametogenesis culture, and mosquito infectivity is not stable over time (22). We selected the wild type *P. falciparum* on NF54 back ground in field isolates, cloned out the high gametogenesis parasite clone PfKF7. Followed experiments confirmed the PfKF7 kept the advantage of stable parasite gametogenesis, especially the transgenic parasite clone PfKF7G4 could be adapted in huRBC-NSG mice after serial passages to proliferate well in blood stage which led to form infective mature gametocytes in vivo for successfully transmitting in mosquitos to produce stable high luciferase expressing mid gut oocysts that those cells, supports *P. falciparum* blood-stage infection (23, 24) that have been used to test anti-malarial drugs targeting asexual parasites (25, 26), to address the biology of *P. falciparum* sexual stages in vivo (27). We developed *P. falciparum*-humanized NSG mouse model to test the ability of epitope-specific CelTOS monoclonal antibodies (mAbs) to block transmission of *P. falciparum* sexual blood stages to mosquito stage oocyst in vivo to meet requirement of transmission-blocking vaccine development.

Parasites growing and lifetime in vivo is related to parasite number of starting inoculation intravenously and huRBC percentage in huRBC-NSG mouse circulation. After 3-time engraftment, huRBC can be enriched up to 25% in mouse, supported adapted PfKF7G4 parasites growing with starting inoculation of 0.3 million mixed-stage parasites. Higher parasites infecting 3-time huRBC-NSG mice will lead to short period of parasite growing and finally cannot reach to high parasitemia in mouse blood due to later engrafted huRBC cannot meet the parasites fast growing in larger scale. To acquire high parasitemia in huRBC-NSG mice in shorter time, infecting the more times engraftment-cycled mice with more parasites initial inoculation is necessary as the method of gametocyte culture in vivo stated above.

Although mouse-adapted PfKF7G4 can be cultured in vivo and matured to infective gametocytes infecting mosquito successfully, the prevalence of infection for mosquitoes is still at the low level (about 25%). Oocysts density of infected mosquitoes is at the range of 1-5 oocysts/midgut. Majority of infected mosquitoes only have one oocysts found in midgut, this is the reason that we pooled 5 mosquitoes to one sample for luciferase assay. The mosquito luciferase assay is so sensitive that it can test difference between one large-developed oocyst and one small-inhibited oocyst by RLU. To mimic mosquito infection condition from mouse model by DFA, we set up and selected the same prevalence of infection mosquitoes infected by SMFA in vitro for transmission blocking inhibition validation experiment with pooled 5 mosquitos as one test sample so that the experimental results in vivo and in vitro are comparable.

Developing TBV has been included in malaria control strategy. Continued success in the global malaria elimination campaign will require development effective vaccines to prevent malaria transmission (28-32). CelTOS has emerged as a leading TBV candidate (16, 33, 34). We investigated epitope-specific CelTOS monoclonal antibodies functional inhibition of Pf4H12 and Pv7G7 to block transmission of *P. falciparum* clone PfKF7G4 using both in vitro with SMFA and in vivo with a *P. falciparum*-humanized mouse model by DFA. Here both of *P. falciparum* and *P. vivax* CelTOS mAbs were effective in blocking transmission. CelTOS has conserved critical function in both *P. falciparum* and *P. vivax*. The high-sequence similarity between Pf and PvCelTOS suggest that CelTOS may elicit cross-species protection. Both *P. falciparum* (Pf) and *P. vivax* (Pv) CelTOS demonstrated significant binding to phosphatidic acid (PA) (16). Pv CelTOS mAb 7G7 showed significant inhibition for *P. falciparum* oocyst in our experiments confirmed CelTOS cross-species protective. In summary, we have identified CelTOS monoclonal antibodies that target malaria parasites.

Towards elucidating the mechanism of malaria parasite neutralization by CelTOS antibodies, reported here within is the first identification of neutralizing and non-neutralizing epitopes in PfCelTOS and PvCelTOS. In addition to identifying the amino acid residues in the epitopes, we also provide the three-dimensional structure of the epitope. The crystal structures of the PfCelTOS/Pf4H12 Fab, PvCelTOS/Pv7G7 Fab and PvCelTSO/Pv6C4 complexes begin to inform the mechanism of antibody-mediated inhibition of CelTOS. In the PfCelTOS/Pf4H12 Fab and PvCelTOS/Pv7G7 Fab complexes we observed electron density for only the two helices of the CelTOS monomer that contain residues engaged by the antibody, whereas the previously reported crystal structure of PvCelTOS was a dimer (16). This suggests that the neutralizing antibodies prevent the dimerization of CelTOS, and that dimerization may be an important step in the mechanism of CelTOS. Alternatively, it is also possible that the crystal structures of the antigen/antibody complexes capture CelTOS in a new state where it is flexible and dynamic. In this case, the neutralizing antibodies stabilize a region of the flexible CelTOS state which results in observing electron density for only the stable region around the epitope.

Interestingly, the observation that crystal structures of antibodies in complex with CelTOS capture new conformational states of CelTOS suggests a strategy for elucidating the mechanism of CelTOS. The biophysical mechanism by which CelTOS disrupts membranes by pore-formation is largely unknown. Pursuing crystal structures of CelTOS/antibody complexes may reveal new states of CelTOS and suggest how the CelTOS dimer, in the pre-pore solution state, transitions to a higher oligomeric pore-state within membranes. It is feasible that the pre-pore dimer comes apart to form a monomer which inserts and oligomerizes in membranes to form a pore. This would suggest that the neutralizing antibodies, Pf4H12 and Pv7G7, lock CelTOS in the monomer state and prevents it from inserting and organizing in membranes.

These examples provide insights into the mechanism of antibody-mediated neutralization of malaria parasites by CelTOS antibodies. The ability of epitope-specific CelTOS monoclonal antibodies (mAbs) to block transmission of *P. falciparum* sexual blood stages to mosquito stage oocyst in vitro and in vivo was investigated. The presence of CelTOS mAb significantly inhibited oocyst development in mosquitoes both in vivo and in vitro assays. Importantly, the experimental results with an innovative in vivo humanized mouse model confirmed that circulating anti-CelTOS antibody effectively inhibits *P. falciparum* ookinete development to oocyst in mosquitoes. These results support the development of CelTOS as a transmission blocking vaccine. The crystal structures of the PfCelTOS/Pf4H12Fab, PvCelTOS/Pv7G7Fab and PvCelTOS/Pv6C4 Fab complexes reveal the structural basis for CelTOS-antibody interaction. Finally, identifying neutralizing and non-neutralizing epitopes in CelTOS informs the structural vaccinology of CelTOS towards the development of a transmission- and infection-blocking malaria vaccine.

Materials and Methods of Examples 1-6

STAR Methods:

piggyBac plasmid (35) pL-BACII-bEDMH-Luc construction and helper plasmid. Using a pair of oligonucleotide primers with Stu1 sites Luc F: 5'-cagctgATGGAAGACGCCAAAAACATAAAGAAA-3' and PbDT3Utr R: 5'-cagctgTACCCTGAAGAAGAAAAGTCCGATGATG-3', Luciferase and PbDHFR3' UTR expression cassette was amplified from genome DNA of 3D7 *P. falciparum* parasites expressing firefly luciferase. The PCR product was then cloned into pGEM-T Easy vector (Promega) and sub-cloned into Stu1 site of mCherry-hDHFR piggyBac vector pL-BacII-bEDMH to obtain pL-BACII-bEDMH-Luc plasmid. piggyBac helper plasmid pDCTH with a dual promoter for transposase expression was used for transfections from previously reported (36).

*Plasmodium falciparum* KF7 Parasite Culture

*P. falciparum* KF7 (PfKF7) is the cloned line from NF54 parasites obtained from Dr. Kappe's lab of Seattle Biomedical Research Institute. We developed the luciferase transgenic parasite in PfKF7, since gametocyte production is more efficient and booming in this parasite line. Asexual PfKF7 parasites were cultured and maintained in human erythrocytes O+ (Interstate Blood Bank) by standard protocols (37, 38) at 5% hematocrit in KD medical RPMI1640 solution w/L-Glutamine containing 25 mM HEPES, 50 mg/L Hypoxanthine, adding 10% heat-inactivated human serum AB (Interstate Blood Bank), 0.1875% sodium bicarbonate (ThermoFisher) and 10 mg/L gentamicin (Invitrogen). Parasite cultures were monitor by Giemsa staining of thin blood smear and maintained at <2% parasitemia at all times and incubated under standard incubator at 37° C. with mixture gas of 5% 02, 5% CO2, and 90% N2. Cultures were routinely monitored for *mycoplasma* contamination by PCR (Takara) and shown to be *mycoplasma* free.

Transfection, Drug Selection and Parasite Cloning

Transfections were performed using plasmid-loaded human O+ red blood cells as described previously (39, 40). Briefly, mature blood-stage parasites were purified on a MACS magnetic column (Miltenyi Biotec) and 3 million purified parasites were added to erythrocytes loaded with 100 ug of transposon piggyBac plasmid-pL-BACII-bEDMH-Luc and 50 ug of the transposase plasmid-pDCTH by electroporation (BioRad Gene Pulser XCell+CE Module, exponential protocol, set at V=310, C=950, R=infinity, mm=2) to start a 5 ml parasite culture. Monitoring the cultures daily, once the parasitemia reached ~1%, placed culture on positive selection drug WR with final concentration of 5 nM in culture medium for 5 days. Waited and let the parasitemia came back to ~1% (2-3 weeks), then did drug selection one more time for 3 days. When parasitemia came back again, cloned out the culture and frozen it down for DNA and −80° C./liquid N2 storage. Individual transfected parasite clones were obtained by limiting dilution of parasites post drug selection. Genotypic analysis of genome-integrated parasite clones was performed by thermal asymmetric interlaced PCR (TAIL-PCR).

huRBC-NSG Mouse Models of *P. falciparum* Infection in Blood Stage

We utilized 10-week female NSG mice (25 g) for *P. falciparum* infection in blood stage. Each experimental NSG mouse was i.v. injected 150 ul O+ human RBC mixed with 50 ul heat-inactivated human serum AB every 3 days while 100 ug clodronate liposomes in 400 ul RPMI medium was i.p. injected in the same time. Using APC anti-human CD235a (Glycophorin A) antibody immunofluorescent staining to detect the level of huRBC in mouse circulation by flow cytometry (FC) analysis. After 3-4 cycles of human erythrocyte engraftment in conjunction with clodronate liposome treatment, NSG mice have been shown to support high level engraftment of huRBC, the proportion of huRBC should be more than 25% in mouse blood circulation before parasite infection, continually cycled huRBC engraftment and clodronate liposome treatment until the end of experiment.

PfKF7G4 Parasite Adaptation Experiment

We first intravenously infected huRBC-NSG mice (huRBC-engrafted and clodronate liposome treated NSG mice after 3 cycles) with 100 ul 3% parasitemia iRBC of PfKF7G4 culture in vitro. Infected mouse blood was cultured in vitro on day 8 post infection. huRBC-NSG mice secondly was infected with 100 ul 0.3% parasitemia iRBC of parasites have been adapted in mouse last time cultured in vitro and so on for third adaption but using 10 ul 0.3% parasitemia iRBC of parasites adapted in mouse second time on day 18 cultured in vitro.

Protein Expression and Purification of CelTOS for Immunization and Assays

PfCelTOS and PvCelTOS constructs were expressed and purified as previously described (16).

Immunization of Mice with PfCelTOS or PvCelTOS

Balb/c mice were immunized with 5 pg of sterile PfCelTOS or PvCelTOS in PBS buffer at the Washington University Hybridoma Center. Immunization boosts were administered via the intravenous route on days 12 and 24, and intraperitoneally on day 42. ELISA confirmed reactivity of polysera from mice to the CelTOS antigen. Briefly, ELISA was performed with 1 mg/ml of antigen probed with a 10-fold dilution series of polysera. The spleens from mice sacrificed on day 47 were collected for the generation of monoclonal antibodies.

Generating Mouse Monoclonal Antibodies Against PfCelTOS and PvCelTOS

Spleens from mice with the highest reactivity to PfCelTOS or PvCelTOS were used to generate monoclonal antibodies. Polyclonal lines were obtained by fusing splenocytes with myeloma cells. The reactivity of the polyclonal cell lines to PfCelTOS or PvCelTOS was examined by ELISA using supernatant from polyclonal cells lines to probe plates coated with 1 mg/ml of antigen. Polyclonal cells lines with the highest reactivity to antigen were subcloned to produce monoclonal Hybridoma cell lines. Specifically, polyclonal cell lines were plated at limited dilution of 100 cells/well, 10 cells/well and 1 cell/well, grown to confluency, and tested by ELISA for reactivity to the antigen. Two additional rounds of subcloning on wells plated at 1 cell/well for each cell line was done to obtain the Hybridoma cell lines declared monoclonal. The Hybridoma lines were isotyped and put into production flasks (Cell line 1000 flasks, ThermoFisher Scientific) to express monoclonal antibodies.

Antibody Sequencing

RNA was isolated from the Hybridoma cell lines of each monoclonal antibody using the TRIzol RNA extraction kit (ThermoFisher Scientific). cDNA was synthesized from the RNA with SuperScript III reverse transcriptase and random hexamers (ThermoFisher Scientific). Amplification of the Ig gene of each monoclonal Hybridoma cell line was performed, and the amplicon sequenced as described (41) with complementary sequencing of missing termini using sequence specific primers.

Purification of Monoclonal IgG, Against PfCelTOS and PvCelTOS, and Fab Generation.

Monoclonal antibodies were purified from Hybridoma cells lines by Protein A antibody affinity chromatography. Briefly, Hybridoma supernatant is diluted 1:1.5 with IgG binding buffer and passed over Protein A resin. The resin is washed with three column volumes. Finally, IgG is eluted with elution buffer and buffer exchanged into PBS using protein concentrators. To generate Fab fragments, the IgG is cleaved with papain and purified with Protein A resin as previously described (11).

Standard Membrane Feeding Assay (SMFA)

The ability of epitope-specific CelTOS monoclonal antibodies (mAbs) to block transmission of *P. falciparum* sexual blood stages to mosquito stage oocyst in vitro was investigated with SMFA (42-45). Briefly, for blood meal preparation, *P. falciparum* PfKF7G4 gametocyte cultures were combined with fresh human erythrocytes and serum to a final gametocyte concentration of 0.3%, and 50% of red blood cells in human serum. Monoclonal antibodies were added to blood meals at a final concentration of 400 ug/ml and same volume PBS for the control, 30 minutes at 37° C. incubation. The prepared blood meal maintained at 37° C. was pipetted into warmed hemotek blood meal reservoir then the cultures were fed to female *Anopheles stephensi* (*A. stephensi*) mosquitoes for 30 minutes at room temperature. Mosquitoes were kept in environmental chamber set at 26° C. and 80% relative humidity supplied with sugar and water ad libitum. Mosquito were collected 8 days after feeding for mosquito luciferase assay.

Mosquito Luciferase Assay

Pooled 5 mosquitoes in 100 ul Passive Lysis Buffer (PLB, Promega, Cat. No. E1941) as one sample in an eppendorf tube on ice. Frozen samples at −80° C. for 2 hours, homogenized sample at RT. Took 50 ul supernatant after centrifuge at 12000 g for 2 min into siliconized polypropylene luminometer tube. Added 100 ul Luciferase Assay Reagent (LAR, Promega, Cat. No. E1483), read each sample Relative Luminescence Units (RLU) immediately with FB12 Single Tube Luminometer (Titertek-Berthold), performed a 2-second premeasurement delay, followed by a 10-second measurement period for each reporter assay, or 50 ul supernatant of mosquito homogenization+100 ul Steady-Glo Luciferase Assay Reagent (SGLAR Promega E25100)/well of 96-well solid white plates for top reads plate (Corning Costar® plate, Cat. No. 3917), read with 96-well plate reader (SpectraMax L Luminescence Microplate Reader, Molecular Device) following the program of Integration time 5", PMT Autorange, Target wave 570 nm. We used Prism (GraphPad) software to do statistical analyses of experiment and inhibition assay results. Each data set was computed with column statistic analysis methods to compare difference between experimental and control groups by using Prism Kruskal-Wallis test with Dunn's multiple comparisons, P value 0.05 was considered significant. *$P \leq 0.05$,  $P \leq 0.01$, *$P \leq 0.001$, ****$P \leq 0.0001$, "ns" for not significance.

Assay to Probe Antibody Inhibition of CelTOS-Mediated Membrane Disruption

Purified PfCelTOS, PvCelTOS and monoclonal antibodies Pf4H12, Pf4D1, Pv7G7 and Pv6C4 were further purified by gel filtration using a Superdex 200 10/300 GL column (GE Healthcare Life Sciences) into buffer composed of 10 mM HEPES pH 7.4 and 150 mM KCl. CelTOS was incubated with antibodies at various molar ratios for one hour. The activity of CelTOS alone, or in combination with antibodies, was determined using the liposome disruption assay for CelTOS previously described (16). Specifically, liposomes composed of phosphatidic acid and containing carboxyfluorescein, were incubated with CelTOS alone or together with antibodies. The extent of membrane disruption was determined by monitoring the fluorescence resulting from the release of carboxyfluorescein from disrupted liposomes.

Crystallization of CelTOS/Antibody Complexes, Data Collection, and Structural Studies CelTOS was incubated with the Fab fragments of monoclonal antibodies at a ratio of 1.5:1 for 30 min at room temperature to allow for formation of CelTOS/Antibody complexes. PfCelTOS/Pf4H12 Fab, PvCelTOS/Pv7G7 Fab and PvCelTOS/Pv6C4 Fab complexes were purified by gel filtration chromatography using a Superdex 200 10/300 GL column (GE Healthcare Life Sciences). Crystals of the PfCelTOS/Pf4H12 Fab complex were grown at 17° C. by hanging-drop vapor diffusion after mixing 1 µl of protein at 13 mg/ml with 1 µl of reservoir containing 0.2 M Lithium acetate and 21% PEG 3350. 25% ethylene glycol was used as cryoprotectant for crystals cryo-cooling. Crystals of PvCelTOS/Pv7G7 Fab complex were grown at 17° C. by hanging-drop vapor diffusion after mixing 1 µl of protein at 20 mg/ml with 1 µl of reservoir containing 0.125M di-sodium hydrogen phosphate 17% Peg 3350. 30% Ethylene Glycol was used for the cryo conditions. X-ray diffraction data from the CelTOS/Antibody complexes was collected at beamline 4.2.2 of the Advanced Light Source (ALS) and processed with XDS (46). The PfCelTOS/Pf4H12 Fab, PvCelTOS/Pv7G7 Fab and PvCelTOS/Pv6C4 Fab complex structures were solved by molecular replacement with PHASER (47). The homology models used were PvCelTOS and modeled IgG domain, based on the antibody sequence and the PIGS server (48). Iterative model building in COOT (49) and refinement in PHENIX (50) led to the current models for PfCelTOS/4H12 (Rfactor/Rfree of 26.4%/32.8%), PvCelTOS/6C4 (Rfactor/Rfree of 24%/29%) and PvCelTOS/7G7 (Rfactor/Rfree of 28.76%/35.32%) Data collection and refinement statistics are shown in Table 2. Epitopes where identified by determining the interface between the antibody and antigen using PDBePISA (51).

Epitope Mapping by Hydrogen-Deuterium Exchange Mass Spectrometry (HDX-MS)

Holo-state samples were prepared by incubating PfCelTOS or PvCelTOS monoclonal antibodies in PBS for 30 minutes at 25° C. The apo state samples were PfCelTOS PvCelTOS in PBS. Continuous hydrogen-deuterium exchange on the holo- and apo-state samples were performed at various time points as described (13, 52).

Example 7—Liver Stage Neutralization by the CelTOS Antibodies

Methods of Example 7

Cell traversal assay: The live cell traversal assay is performed using a HC-04 hepatoma line cultured under standard cell culture conditions and seeded at 4,000 cells per well (200 cells/pL) in a 384-well (Corning Biocoat) plate. Cells are incubated overnight to allow for complete attachment then stained with CellTracker™ Green (1 pg/ml) and Hoechst (10 pg/ml) for 30 minutes at 37° C. Cells are washed twice with incomplete HC-04 media. Serum samples are exposed to freshly dissected sporozoites for 30 minutes at room temperature then 2,500 sporozoites at a concentration of 125 sporozoites/µL are added to the HC-04 cells. The plate is spun down for 5 minutes at 200 g. Cell traversal events are captured using live-cell time-lapse imaging at 1 frame/2 minutes (20× objective) in well centers for a total time of 30 minutes. Imaging analysis can be performed on Operetta system or manually using ImageJ to compare first and last frames for hepatocyte lysis.

PHH invasion: Cryopreserved primary human hepatocyte lots and hepatocyte culture medium (HCM) (InVitroGro™ CP Medium) from Bioreclamation IVT, Inc (Baltimore, MD, U.S.A.) have been used in previous *Plasmodium vivax* liver stage studies (Maher, Roth manuscript in prep). Bioreclamation IVT, Inc offers highly viable and biologically functional cryopreserved hepatocytes from multiple species including rhesus monkey hepatocytes. In brief, cryopreserved hepatocytes are thawed following manufacturer's protocols and suspended in the hepatocyte culture medium supplemented with 1% penicillin-streptomycin antibiotic solution. The in vitro liver model, MWD, is coated with 3.81 mg/ml rat tail collagen I (BD™, Waltham, MA, U.S.A.) diluted in 0.02M acetic acid and incubated at 37° C. overnight to ensure absorption. A vial of cryopreserved hepatocytes (5-9 million hepatocytes per vial) will be thawed and seeded at 18,000 live hepatocyte cells per well at a concentration of 900 cells/pL in HCM. Static hepatocyte cultures will be subjected to alternate day media changes (50% volume) supplemented with antibiotic cocktail. Final *Plasmodium* sporozoite inoculations will be determined experimentally, however, statistically relevant infection rates have been identified with *P. vivax* at MOIs of 5,000, 10,000 and 20,000 sporozoites per well. For serum exposure, sporozoites will be incubated with serial diluted serum in HCM at 2-fold iterations (6 dilutions in duplicates) for 30 minutes at room temperature. As a control, sporozoites will be exposed to pre-immune serum diluted in HCM and held at room temperature for 30 min. After incubation, 5,000 to 20,000 sporozoites from each condition will be added into MWDs, spun down for 5 minutes at 200 g, and allowed to invade overnight before washing with complete HCM. At 4 and 8 days post infection, MWDs will be fixed with % PFA for 10 minutes at room temperature and washed twice with PBS. Wells will be stained and imaged following previously determined USF protocols.

Results of Sporozoite Functional Assays:

These results provide clear evidence of anti-CelTOS functional inhibition of *Plasmodium falciparum* and/or *Plasmodium vivax* sporozoites as observed by in vitro assays for cell traversal and hepatocyte infection.

Anti-celTOS 7G7

Increased concentrations of Ab 7G7 exhibited increased levels of inhibition of sporozoite cell traversal and infection of PHH until complete functional inhibition of sporozoites was achieved (FIG. 14).

Anti-celtTOS 4H12

Increased concentrations of Ab 4H12 exhibited increased levels of inhibition of sporozoite cell traversal and infection of PHH until complete functional inhibition of sporozoites was achieved (FIG. 15).

Anti-celTOS 4D1

Increased concentrations of AB 4D1 exhibited increased inhibition of inhibition of *P. falciparum* and *P. vivax* sporozoite cell traversal and infection of PHH until complete functional inhibition of sporozoites was achieved (FIG. 16A). A dramatic increase of infected PHH resulted from high concentrations of 4D1 anti-CelTOS functional inhibition by trapping *P. vivax* sporozoites inside PHH. Importantly, development to LS traversal-arrested sporozoites was significantly stunted even at low concentrations (FIG. 16B-D).

REFERENCES

1. Huang Y M, Shi L W, She R, Bai J, Jiao S Y, Guo Y. Domestic trends in malaria research and development in China and its global influence. Infect Dis Poverty. 2017; 6(1):4. doi: 10.1186/s40249-016-0222-x. PubMed PMID: 28069075; PMCID: PMC5223349.
2. Tanner M, Greenwood B, Whitty C J, Ansah E K, Price R N, Dondorp A M, von Seidlein L, Baird J K, Beeson J G, Fowkes F J, Hemingway J, Marsh K, Osier F. Malaria eradication and elimination: views on how to translate a vision into reality. BMC Med. 2015; 13:167. doi: 10.1186/s12916-015-0384-6. PubMed PMID: 26208740; PMCID: PMC4514994.
3. WHO. World Malaria Report 2016. Geneva, Switzerland: World Health Organization; 2016. p. 1-186.
4. Wellems T E, Hayton K, Fairhurst R M. The impact of malaria parasitism: from corpuscles to communities. J Clin Invest. 2009; 119(9):2496-505. doi: 10.1172/JCI38307. PubMed PMID: 19729847; PMCID: PMC2735907.
5. Dondorp A M, Fairhurst R M, Slutsker L, Macarthur J R, Breman J G, Guerin P J, Wellems T E, Ringwald P, Newman R D, Plowe C V. The threat of artemisinin-resistant malaria. N Engl J Med. 2011; 365(12):1073-5. doi: 10.1056/NEJMp1108322. PubMed PMID: 21992120; PMCID: PMC3733336.
6. Pantaleo A, Pau M C, Chien H D, Turrini F. Artemisinin resistance, some facts and opinions. J Infect Dev Ctries. 2015; 9(6):597-9. doi: 10.3855/jidc.7015. PubMed PMID: 26142668.
7. Hall B F, Fauci A S. Malaria control, elimination, and eradication: the role of the evolving biomedical research agenda. J Infect Dis. 2009; 200(11):1639-43. doi: 10.1086/646611. PubMed PMID: 19877843.
8. Crompton P D, Pierce S K, Miller L H. Advances and challenges in malaria vaccine development. J Clin Invest. 2010; 120(12):4168-78. Epub 2010/12/03. doi: 10.1172/JCI44423. PubMed PMID: 21123952; PMCID: 2994342.
9. Lyke K E, Ishizuka A S, Berry A A, Chakravarty S, DeZure A, Enama M E, James E R, Billingsley P F, Gunasekera A, Manoj A, Li M, Ruben A J, Li T, Eappen A G, Stafford R E, Kc N, Murshedkar T, Mendoza F H, Gordon I J, Zephir K L, Holman L A, Plummer S H, Hendel C S, Novik L, Costner P J, Saunders J G, Berkowitz N M, Flynn B J, Nason M C, Garver L S, Laurens M B, Plowe C V, Richie T L, Graham B S, Roederer M, Sim B K, Ledgerwood J E, Hoffman S L, Seder R A. Attenuated PfSPZ Vaccine induces strain-transcending T cells and durable protection against heterologous controlled human malaria infection. Proc Natl Acad Sci USA. 2017; 114(10):2711-6. Epub 2017/02/21. doi: 10.1073/pnas.1615324114. PubMed PMID: 28223498.
10. Dormitzer P R, Grandi G, Rappuoli R. Structural vaccinology starts to deliver. Nat Rev Microbiol. 2012; 10(12):807-13. doi: 10.1038/nrmicro2893. PubMed PMID: 23154260.
11. Chen E, Paing M M, Salinas N, Sim B K, Tolia N H. Structural and functional basis for inhibition of erythrocyte invasion by antibodies that target *Plasmodium falciparum* EBA-175. PLoS Pathog. 2013; 9(5):e1003390. doi: 10.1371/journal.ppat.1003390. PubMed PMID: 23717209; PMCID: PMC3662668.
12. Chen E, Salinas N D, Ntumngia F B, Adams J H, Tolia N H. Structural analysis of the synthetic Duffy Binding Protein (DBP) antigen DEKnull relevant for *Plasmodium vivax* malaria vaccine design. PLoS Negl Trop Dis. 2015; 9(3):e0003644. doi: 10.1371/journal.pntd.0003644. PubMed PMID: 25793371; PMCID: PMC4368114.
13. Chen E, Salinas N D, Huang Y, Ntumngia F, Plasencia M D, Gross M L, Adams J H, Tolia N H. Broadly neutralizing epitopes in the *Plasmodium vivax* vaccine candidate Duffy Binding Protein. Proc Natl Acad Sci USA. 2016; 113(22):6277-82. doi: 10.1073/pnas.1600488113. PubMed PMID: 27194724; PMCID: PMC4896725.
14. Correia B E, Bates J T, Loomis R J, Baneyx G, Carrico C, Jardine J G, Rupert P, Correnti C, Kalyuzhniy O, Vittal V, Connell M J, Stevens E, Schroeter A, Chen M, Macpherson S, Serra A M, Adachi Y, Holmes M A, Li Y, Klevit R E, Graham B S, Wyatt R T, Baker D, Strong R K, Crowe J E, Johnson P R, Schief W R. Proof of principle for epitope-focused vaccine design. Nature. 2014; 507(7491):201-6. doi: 10.1038/nature12966. PubMed PMID: 24499818; PMCID: PMC4260937.
15. Kariu T, Ishino T, Yano K, Chinzei Y, Yuda M. CelTOS, a novel malarial protein that mediates transmission to mosquito and vertebrate hosts. Mol Microbiol. 2006; 59:1369-79. Epub 02/14. doi: 10.1111/j.1365-2958.2005.05024.x. PubMed PMID: 16468982.
16. Jimah J R, Salinas N D, Sala-Rabanal M, Jones N G, Sibley L D, Nichols C G, Schlesinger P H, Tolia N H. Malaria parasite CelTOS targets the inner leaflet of cell membranes for pore-dependent disruption. Elife. 2016; 5. Epub 2016/12/01. doi: 10.7554/eLife.20621. PubMed PMID: 27906127; PMCID: PMC5132341.
17. Bergmann-Leitner E S, Legler P M, Savranskaya T, Ockenhouse C F, Angov E. Cellular and humoral immune effector mechanisms required for sterile protection against sporozoite challenge induced with the novel malaria vaccine candidate CelTOS. Vaccine. 2011; 29(35):5940-9. doi: 10.1016/j.vaccine.2011.06.053. PubMed PMID: 21722682.
18. Espinosa D A, Vega-Rodriguez J, Flores-Garcia Y, Noe A R, Munoz C, Coleman R, Bruck T, Haney K, Stevens A, Retallack D, Allen J, Vedvick T S, Fox C B, Reed S G, Howard R F, Salman A M, Janse C J, Khan S M, Zavala F, Gutierrez G M. The *Plasmodium falciparum* Cell-Traversal Protein for Ookinetes and Sporozoites as a Candidate for Preerythrocytic and Transmission-Blocking Vaccines. Infect Immun. 2017; 85(2). Epub 2017/01/26. doi: 10.1128/IAI.00498-16. PubMed PMID: 27895131; PMCID: PMC5278177.

19. Bergmann-Leitner E S, Mease R M, De La Vega P, Savranskaya T, Polhemus M, Ockenhouse C, Angov E. Immunization with pre-erythrocytic antigen CelTOS from *Plasmodium falciparum* elicits cross-species protection against heterologous challenge with *Plasmodium berghei*. PLoS One. 2010; 5:0012294. doi: 10.1371/journal.pone.

20. Rodrigues-da-Silva R N, Soares I F, Lopez-Camacho C, Martins da Silva J H, Perce-da-Silva D S, Teva A, Ramos Franco A M, Pinheiro F G, Chaves L B, Pratt-Riccio L R, Reyes-Sandoval A, Banic D M, Lima-Junior J D. *Plasmodium vivax* Cell-Traversal Protein for Ookinetes and Sporozoites: Naturally Acquired Humoral Immune Response and B-Cell Epitope Mapping in Brazilian Amazon Inhabitants. Front Immunol. 2017; 8:77. Epub 2017/02/07. doi: 10.3389/fimmu.2017.00077. PubMed PMID: 28223984; PMCID: PMC5293784.

21. Bitencourt Chaves L, Perce-da-Silva D S, Rodrigues-da-Silva R N, Martins da Silva J H, Cassiano G C, Machado R L, Pratt-Riccio L R, Banic D M, Lima-Junior J D. *Plasmodium vivax* Cell Traversal Protein for Ookinetes and Sporozoites (PvCelTOS) gene sequence and potential epitopes are highly conserved among isolates from different regions of Brazilian Amazon. PLoS Negl Trop Dis. 2017; 11(2):e0005344. Epub 2017/02/03. doi: 10.1371/journal.pntd.0005344. PubMed PMID: 28158176; PMCID: PMC5310920.

22. Vaughan A M, Mikolajczak S A, Camargo N, Lakshmanan V, Kennedy M, Lindner S E, Miller J L, Hume J C, Kappe S H. A transgenic *Plasmodium falciparum* NF54 strain that expresses GFP-luciferase throughout the parasite life cycle. Mol Biochem Parasitol. 2012; 186(2): 143-7. doi: 10.1016/j.molbiopara.2012.10.004. PubMed PMID: 23107927.

23. Arnold L, Tyagi R K, Meija P, Swetman C, Gleeson J, Perignon J L, Druilhe P. Further improvements of the *P. falciparum* humanized mouse model. PLoS One. 2011; 6(3):e18045. doi: 10.1371/journal.pone.0018045. PubMed PMID: 21483851; PMCID: PMC3069031.

24. Ito M, Hiramatsu H, Kobayashi K, Suzue K, Kawahata M, Hioki K, Ueyama Y, Koyanagi Y, Sugamura K, Tsuji K, Heike T, Nakahata T. NOD/SCID/gamma(c)(null) mouse: an excellent recipient mouse model for engraftment of human cells. Blood. 2002; 100(9):3175-82. doi: 10.1182/blood-2001-12-0207. PubMed PMID: 12384415.

25. Vaughan A M, Kappe S H, Ploss A, Mikolajczak S A. Development of humanized mouse models to study human malaria parasite infection. Future Microbiol. 2012; 7(5):657-65. doi: 10.2217/fmb.12.27. PubMed PMID: 22568719; PMCID: PMC3848604.

26. Moreno A, Perignon J L, Morosan S, Mazier D, Benito A. *Plasmodium falciparum*-infected mice: more than a tour de force. Trends Parasitol. 2007; 23(6):254-9. doi: 10.1016/j.pt.2007.04.004. PubMed PMID: 17434343.

27. Duffier Y, Lorthiois A, Cistero P, Dupuy F, Jouvion G, Fiette L, Mazier D, Mayor A, Lavazec C, Moreno Sabater A. A humanized mouse model for sequestration of *Plasmodium falciparum* sexual stages and in vivo evaluation of gametocytidal drugs. Sci Rep. 2016; 6:35025. doi: 10.1038/srep35025. PubMed PMID: 27731362; PMCID: PMC5059736.

28. Zheng W, Liu F, He Y, Liu Q, Humphreys G B, Tsuboi T, Fan Q, Luo E, Cao Y, Cui L. Functional characterization of *Plasmodium berghei* PSOP25 during ookinete development and as a malaria transmission-blocking vaccine candidate. Parasit Vectors. 2017; 10(1):8. doi: 10.1186/s13071-016-1932-4. PubMed PMID: 28057055; PMCID: PMC5217559.

29. Theisen M, Jore M M, Sauerwein R. Towards clinical development of a Pfs48/45-based transmission blocking malaria vaccine. Expert Rev Vaccines. 2017; 16(4):329-36. doi: 10.1080/14760584.2017.1276833. PubMed PMID: 28043178.

30. Talaat K R, Ellis R D, Hurd J, Hentrich A, Gabriel E, Hynes N A, Rausch K M, Zhu D, Muratova O, Herrera R, Anderson C, Jones D, Aebig J, Brockley S, MacDonald N J, Wang X, Fay M P, Healy S A, Durbin A P, Narum D L, Wu Y, Duffy P E. Safety and Immunogenicity of Pfs25-EPA/Alhydrogel®, a Transmission Blocking Vaccine against *Plasmodium falciparum*: An Open Label Study in Malaria Naive Adults. PLoS One. 2016; 11(10): e0163144. doi: 10.1371/journal.pone.0163144. PubMed PMID: 27749907; PMCID: PMC5066979.

31. Lee S M, Wu C K, Plieskatt J, McAdams D H, Miura K, Ockenhouse C, King C R. Assessment of Pfs25 expressed from multiple soluble expression platforms for use as transmission-blocking vaccine candidates. Malar J. 2016; 15(1):405. doi: 10.1186/s12936-016-1464-6. PubMed PMID: 27515826; PMCID: PMC4982271.

32. Juliano J J, Parobek C M, Brazeau N F, Ngasala B, Randrianarivelojosia M, Lon C, Mwandagalirwa K, Tshefu A, Dhar R, Das B K, Hoffman I, Martinson F, Martensson A, Saunders D L, Kumar N, Meshnick S R. Pooled Amplicon Deep Sequencing of Candidate *Plasmodium falciparum* Transmission-Blocking Vaccine Antigens. Am J Trop Med Hyg. 2016; 94(1):143-6. doi: 10.4269/ajtmh.15-0571. PubMed PMID: 26503281; PMCID: PMC4710419.

33. Anum D, Kusi K A, Ganeshan H, Hollingdale M R, Ofori M F, Koram K A, Gyan B A, Adu-Amankwah S, Badji E, Huang J, Belmonte M, Banania G J, Kwofie T B, Villasante E, Dodoo D, Sedegah M. Measuring naturally acquired ex vivo IFN-gamma responses to *Plasmodium falciparum* cell-traversal protein for ookinetes and sporozoites (CelTOS) in Ghanaian adults. Malar J. 2015; 14:20. doi: 10.1186/s12936-014-0539-5. PubMed PMID: 25604473; PMCID: PMC4308902.

34. Ferraro B, Talbott K T, Balakrishnan A, Cisper N, Morrow M P, Hutnick N A, Myles D J, Shedlock D J, Obeng-Adjei N, Yan J, Kayatani A K, Richie N, Cabrera W, Shiver R, Khan A S, Brown A S, Yang M, Wille-Reece U, Birkett A J, Sardesai N Y, Weiner D B. Inducing humoral and cellular responses to multiple sporozoite and liver-stage malaria antigens using exogenous plasmid DNA. Infect Immun. 2013; 81(10):3709-20. doi: 10.1128/IAI.00180-13. PubMed PMID: 23897618; PMCID: PMC3811783.

35. Balu B, Shoue D A, Fraser M J, Jr., Adams J H. High-efficiency transformation of *Plasmodium falciparum* by the lepidopteran transposable element piggyBac. Proc Natl Acad Sci USA. 2005; 102(45):16391-6. doi: 10.1073/pnas.0504679102. PubMed PMID: 16260745; PMCID: PMC1275597.

36. Balu B, Adams J H. Functional genomics of *Plasmodium falciparum* through transposon-mediated mutagenesis.

36. Cell Microbiol. 2006; 8(10):1529-36. doi: 10.1111/j.1462-5822.2006.00776.x. PubMed PMID: 16984409.
37. Campbell J R. In vitro culture of *Plasmodium falciparum*. J Parasitol. 1984; 70(6):966. PubMed PMID: 6396396.
38. Chavalitshewinkoon P, Wilairat P. A simple technique for large scale in vitro culture of *Plasmodium falciparum*. Southeast Asian J Trop Med Public Health. 1991; 22(4): 544-7. PubMed PMID: 1820642.
39. Balu B, Singh N, Maher S P, Adams J H. A genetic screen for attenuated growth identifies genes crucial for intraerythrocytic development of *Plasmodium falciparum*. PLoS One. 2010; 5(10):e13282. doi: 10.1371/journal.pone.0013282. PubMed PMID: 20949012; PMCID: PMC2952599.
40. Balu B, Chauhan C, Maher S P, Shoue D A, Kissinger J C, Fraser M J, Jr., Adams J H. piggyBac is an effective tool for functional analysis of the *Plasmodium falciparum* genome. BMC Microbiol. 2009; 9:83. doi: 10.1186/1471-2180-9-83. PubMed PMID: 19422698; PMCID: PMC2686711.
41. Tiller T, Busse C E, Wardemann H. Cloning and expression of murine Ig genes from single B cells. J Immunol Methods. 2009; 350(1-2):183-93. Epub 2009/08/27. doi: 10.1016/j.jim.2009.08.009. PubMed PMID: 19716372.
42. Miura K, Swihart B J, Deng B, Zhou L, Pham T P, Diouf A, Burton T, Fay M P, Long C A. Transmission-blocking activity is determined by transmission-reducing activity and number of control oocysts in *Plasmodium falciparum* standard membrane-feeding assay. Vaccine. 2016; 34(35): 4145-51. doi: 10.1016/j.vaccine.2016.06.066. PubMed PMID: 27372156; PMCID: PMC4958521.
43. Miura K, Takashima E, Deng B, Tullo G, Diouf A, Moretz S E, Nikolaeva D, Diakite M, Fairhurst R M, Fay M P, Long C A, Tsuboi T. Functional comparison of *Plasmodium falciparum* transmission-blocking vaccine candidates by the standard membrane-feeding assay. Infect Immun. 2013; 81(12):4377-82. doi: 10.1128/IAI.01056-13. PubMed PMID: 24042109; PMCID: PMC3838000.
44. Churcher T S, Blagborough A M, Delves M, Ramakrishnan C, Kapulu M C, Williams A R, Biswas S, Da D F, Cohuet A, Sinden R E. Measuring the blockade of malaria transmission—an analysis of the Standard Membrane Feeding Assay. Int J Parasitol. 2012; 42(11): 1037-44. doi: 10.1016/j.ijpara.2012.09.002. PubMed PMID: 23023048.
45. van der Kolk M, De Vlas S J, Saul A, van de Vegte-Bolmer M, Eling W M, Sauerwein R W. Evaluation of the standard membrane feeding assay (SMFA) for the determination of malaria transmission-reducing activity using empirical data. Parasitology. 2005; 130(Pt 1):13-22. PubMed PMID: 15700753.
46. Kabsch W. Xds. Acta Crystallogr D Biol Crystallogr. 2010; 66(Pt 2):125-32. Epub 2010/02/04. doi: 10.1107/S0907444909047337. PubMed PMID: 20124692; PMCID: 2815665.
47. McCoy A J, Grosse-Kunstleve R W, Adams P D, Winn M D, Storoni L C, Read R J. Phaser crystallographic software. J Appl Crystallogr. 2007; 40(Pt 4):658-74. Epub 2007/08/01. doi: 10.1107/S0021889807021206. PubMed PMID: 19461840; PMCID: 2483472.
48. Marcatili P, Rosi A, Tramontano A. PIGS: automatic prediction of antibody structures. Bioinformatics. 2008; 24(17):1953-4. doi: 10.1093/bioinformatics/btn341. PubMed PMID: 18641403.
49. Emsley P, Cowtan K. Coot: model-building tools for molecular graphics. Acta Crystallogr D Biol Crystallogr. 2004; 60(Pt 12 Pt 1):2126-32. PubMed PMID: 15572765.
50. Adams P D, Grosse-Kunstleve R W, Hung L W, Ioerger TR, McCoy A J, Moriarty N W, Read R J, Sacchettini J C, Sauter N K, Terwilliger T C. PHENIX: building new software for automated crystallographic structure determination. Acta Crystallogr D Biol Crystallogr. 2002; 58(Pt 11):1948-54. PubMed PMID: 12393927.
51. Krissinel E, Henrick K. Inference of macromolecular assemblies from crystalline state. J Mol Biol. 2007; 372(3):774-97. Epub 2007/08/08. doi: 10.1016/j.jmb.2007.05.022. PubMed PMID: 17681537.
52. Yan Y, Grant G A, Gross M L. Hydrogen-Deuterium Exchange Mass Spectrometry Reveals Unique Conformational and Chemical Transformations Occurring upon [4Fe-4S] Cluster Binding in the Type 2 L-Serine Dehydratase from *Legionella pneumophila*. Biochemistry. 2015; 54(34):5322-8. doi: 10.1021/acs.biochem.5b00761. PubMed PMID: 26266572.

What is claimed is:

1. An antibody, wherein the antibody comprises (a) a heavy chain comprising a CDR1 comprising the amino acid sequence GYSFTDYN (amino acids 24-31 of SEQ ID NO: 79), a CDR2 comprising the amino acid sequence IDPYNGGT (amino acids 49-56 of SEQ ID NO: 79), and a CDR3 comprising the amino acid sequence ARGYYYGNPLHFDV (amino acids 96-108 of SEQ ID NO: 79); and (b) a light chain comprising a CDR1 comprising the amino acid sequence SSVSY (amino acids 26-31 of SEQ ID NO: 80), a CDR2 comprising the amino acid sequence DTS (amino acids 49-51 of SEQ ID NO: 80), and a CDR3 comprising the amino acid sequence QQWISYPAT (amino acids 88-96 of SEQ ID NO: 80).

2. The antibody of claim 1, wherein the antibody is selected from the group consisting of a single-chain antibody, an antibody fragment, and a humanized antibody.

3. A pharmaceutical composition comprising the antibody of claim 1 and a diluent, an excipient or a carrier.

4. The antibody of claim 1, wherein the heavy chain variable region comprises the amino acid sequence set forth in SEQ ID NO: 79 and the light chain variable region comprises the amino acid sequence set forth in SEQ ID NO: 80.

5. A method of treating a *Plasmodium* infection in a human subject in need thereof, comprising, administering an effective amount of a composition comprising the antibody of claim 4 to the subject, wherein the *Plasmodium* infection is a *Plasmodium vivax* infection or a *Plasmodium falciparum* infection.

6. The method of claim 5, wherein the effective amount of the antibody reduces or eliminates the traversal of infective sporozoites through cells required for infection of liver cells and thus protects against infections and/or reduces the severity of the disease.

7. The method of claim 5, further comprising administering an antiparasitic agent.

* * * * *